US010975384B2

(12) United States Patent
Zhu et al.

(10) Patent No.: US 10,975,384 B2

(45) Date of Patent: Apr. 13, 2021

(54) PYL9 AND USES THEREOF

(71) Applicant: PURDUE RESEARCH FOUNDATION, West Lafayette, IN (US)

(72) Inventors: Jian-Kang Zhu, Newport Coast, CA (US); Zhulong Chan, Wuhan (CN); Ray Bressan, West Lafayette, IN (US); Yang Zhao, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 15/773,215

(22) PCT Filed: Nov. 17, 2016

(86) PCT No.: PCT/US2016/062468

§ 371 (c)(1),
(2) Date: May 3, 2018

(87) PCT Pub. No.: WO2017/087633

PCT Pub. Date: May 26, 2017

(65) Prior Publication Data

US 2018/0320194 A1 Nov. 8, 2018

Related U.S. Application Data

(60) Provisional application No. 62/257,027, filed on Nov. 18, 2015.

(51) Int. Cl.

*C12N 15/82* (2006.01)
*C07K 14/415* (2006.01)

(52) U.S. Cl.

CPC ........ *C12N 15/8273* (2013.01); *C07K 14/415* (2013.01); *C12N 15/8201* (2013.01); *C12N 15/8266* (2013.01); *C12N 15/8293* (2013.01)

(58) Field of Classification Search

None

See application file for complete search history.

(56) References Cited

U.S. PATENT DOCUMENTS

| | | | | |
|---|---|---|---|---|
| 2006/0150283 A1 | 7/2006 | Alexandrov et al. | | |
| 2010/0216643 A1* | 8/2010 | Cutler | C12N 9/16 504/242 | |
| 2012/0011615 A1 | 1/2012 | Han et al. | | |
| 2014/0259226 A1* | 9/2014 | Cutler | C12N 15/8273 800/298 | |
| 2015/0074844 A1 | 3/2015 | Zhu et al. | | |

FOREIGN PATENT DOCUMENTS

WO WO 2014/184193 11/2014

OTHER PUBLICATIONS

Ma, et al. (Science 324.5930 (2009): 1064-1068). (Year: 2009).*

Geiger et al. (Sci. Signal. 4.173 (2011): ra32-ra32). (Year: 2011).*

Li, et al. (International journal of molecular sciences 15.5 (2014): 8473-8490). (Year: 2014).*

GenBank Accession NM_100018, dated Oct. 22, 2014. (Year: 2014).*

GenBank Accession NM 124610, submitted Jan. 22, 2014. (Year: 2014).*

Yamaguchi-Shinozaki et al. (Molecular and General Genetics MGG 236.2-3 (1993): 331-340). (Year: 1993).*

Kasuga et al. (Plant and Cell Physiology 45.3 (2004): 346-350). (Year: 2004).*

Kocheva et al. (General Appl Plant Physiol 35 (2009): 127-133). (Year: 2009).*

Jaradat, et al. (BMC Plant Biology 13.1 (2013): 192, p. 2, left col. ¶ 3). (Year: 2013).*

Antoni, R. et al. (2013) Pyrabactin RESISTANCE1-LIKE8 plays an important role for the regulation of abscisic acid signaling in root[1[C][W][OA]], *Plant Physiol*, 161(2):931-941.

Balazadeh, S. et al., (2011) ORS1, an H2O2-responsive NAC transcription factor, controls senescence in *Arabidopsis thaliana*. Mol Plant, 4(2):346-360.

Bhaskara, G.B. et al. (2012) Unique drought resistance functions of the highly ABA-induced Glade a protein phosphatase 2Cs. *Plant Physiol*, 160(1):379-395.

Buchanan-Wollaston, V. et al. (2005) Comparative transcriptome analysis reveals significant differences in gene expression and signalling pathways between developmental and dark/starvation-induced senescence in *Arabidopsis. Plant J*, 42(4):567-585.

Cao, M. et al. (2013) An ABA-mimicking ligand that reduces water loss and promotes drought resistance in plants. *Cell Res*, 23(8):1043-1054.

Chattopadhyay, S. et al. (1998) Arabidopsis bZIP protein HY5 directly interacts with light-responsive promoters in mediating light control of gene expression. *Plant Cell*, 10(5):673-683.

Chen, L.Q. et al. (2012) Sucrose efflux mediated by SWEET proteins as a key step for phloem transport. *Science*, 335(6065):207-211.

Feng, C.Z. et al. (2014) Arabidopsis RAV1 transcription factor, phosphorylated by SnRK2 kinases, regulates the expression of ABI3, ABI4, and ABI5 during seed germination and early seedling development. *Plant J*, 80(4):654-668.

Fujii, H. et al. (2009) *Arabidopsis* mutant deficient in 3 abscisic acid-activated protein kinases reveals critical roles in growth, reproduction, and stress. *Proc Natl Acad Sci USA*, 106(20):8380-8385.

Fujii, H. et al. (2009) In vitro reconstitution of an abscisic acid signalling pathway. *Nature*, 462(7273): 660-664.

Furihata, T. et al. (2006) Abscisic acid-dependent multisite phosphorylation regulates the activity of a transcription activator AREB1. *Proc Natl Acad Sci USA*, 103(6):1988-1993.

(Continued)

*Primary Examiner* — Charles Logsdon

(74) *Attorney, Agent, or Firm* — Marianne Fuierer; Olive Law Group, PLLC

(57) ABSTRACT

The present invention provides for transgenic plants and methods of producing such transgenic plants, wherein the transgenic plants express an increased amounts of PYL9 to interact with abscisic acid (ABA) thereby activating enhanced drought resistance and leaf senescence relative to control or wild-type plants.

9 Claims, 18 Drawing Sheets

Specification includes a Sequence Listing.

(56) References Cited

OTHER PUBLICATIONS

Gan, S. et al. (1995) Inhibition of leaf senescence by autoregulated production of cytokinin. *Science*, 270(5244):1986-1988.
González-Grandío, E. et al. (2013) BRANCHED1 promotes axillary bud dormancy in response to shade in *Arabidopsis. Plant Cell*, 25(3):834-850.
Guo, Y. et al. (2006) AtNAP, a NAC family transcription factor, has an important role in leaf senescence. *Plant J*, 46(4):601-612.
Hao, Q. et al. (2011) The molecular basis of ABA-independent inhibition of PP2Cs by a subclass of PYL proteins. *Mol Cell*, 42(5):662-672.
Jin, R. et al. (2015) Physiological changes of purslane (*Portulaca oleracea* L.) after progressive drought stress and rehydration. *Sci Hortic*, (Amsterdam) 194:215-221.
Kim, J.H. et al. (2009) Trifurcate feed-forward regulation of age-dependent cell death involving miR164 in *Arabidopsis. Science*, 323(5917):1053-1057.
Kim, J.H. et al. (2011) Three positive regulators of leaf senescence in *Arabidopsis*, ORE1, ORE3 and ORE9, play roles in crosstalk among multiple hormone-mediated senescence pathways. *Genes Genomics*, 33(4):373-381.
Li, Z. et al. (2012) ROP11 GTPase is a negative regulator of multiple ABA responses in *Arabidopsis. J Integr Plant Biol*, 54(3):169-179.
Liang, C. et al. (2014) OsNAP connects abscisic acid and leaf senescence by fine-tuning abscisic acid biosynthesis and directly targeting senescence-associated genes in rice. *Proc Natl Acad Sci USA*, 111(27):10013-10018.
Lim, P.O. et al. (2007) Leaf senescence. *Annu Rev Plant Biol*, 58:115-136.
Ma, Y. et al. (2009) Regulators of PP2C phosphatase activity function as abscisic acid sensors. *Science*, 324(5930):1064-1068.
Munné-Bosch, S. et al . (2004) Die and let live: Leaf senescence contributes to plant survival under drought stress. *Funct Plant Biol*, 31(3):203-216.
Okamoto, M. et al. (2013) Activation of dimeric ABA receptors elicits guard cell closure, ABA-regulated gene expression, and drought tolerance. *Proc Natl Acad Sci USA*, 110(29):12132-12137.
Olsen, A.N. et al. (2005) DNA-binding specificity and molecular functions of NAC transcription factors. Plant Sci 169(4):785-797.
Park, S.Y. et al. (2009) Abscisic acid inhibits type 2C protein phosphatases via the PYR/PYL family of START proteins. *Science*, 324(5930):1068-1071.
Riov, J. et al. 1990) Characterization of abscisic Acid-induced ethylene production in citrus leaf and tomato fruit tissues. *Plant Physiol*, 92(1):48-53.
Rivero, R.M. et al. (2007) Delayed leaf senescence induces extreme drought tolerance in a flowering plant. *Proc Natl Acad Sci USA*, 104(49):19631-19636.
Ruttink, T. et al. (2007) A molecular timetable for apical bud formation and dormancy induction in poplar. *Plant Cell*, 19(8):2370-2390.
Sakuraba, Y. et al. (2014) Phytochrome-interacting transcription factors PIF4 and PIF5 induce leaf senescence in *Arabidopsis. Nat Commun*, 5:4636.
Samuels, L. et al. (2008) Sealing plant surfaces: Cuticular wax formation by epidermal cells. *Annu Rev Plant Biol*, 59:683-707.
Shen, Q. et al. (1995) Functional dissection of an abscisic acid (ABA)-inducible gene reveals two independent ABA-responsive complexes each containing a G-box and a novel cis-acting element. *Plant Cell*, 7(3):295-307.
Shi, H. et al. (2014) Constitutive production of nitric oxide leads to enhanced drought stress resistance and extensive transcriptional reprogramming in *Arabidopsis. J Exp Bot*, 651 151:4119-4131.
Uauy, C. et al. (2006) A NAC Gene regulating senescence improves grain protein, zinc, and iron content in wheat. *Science*, 314(5803):1298-1301.
Van Der Graaff, E. et al. (2006) Transcription analysis of *Arabidopsis* membrane transporters and hormone pathways during developmental and induced leaf senescence. *Plant Physiol*, 141(2):776-792.
Volaire, F. et al. (2006) Summer dormancy in perennial temperate grasses. *Ann Bot*, (Lond) 98(5):927-933.
Weaver, L.M. et al. (1998) A comparison of the expression patterns of several senescence-associated genes in response to stress and hormone treatment. *Plant Mol Biol*, 37(3):455-469.
Woo, H.R. et al. (2010) The RAV1 transcription factor positively regulates leaf senescence in *Arabidopsis. J Exp Bot*, 61(14):3947-3957.
Yang, Y. et al. (2008) Isolation of a strong *Arabidopsis* guard cell promoter and its potential as a research tool. *Plant Methods*, 4(1):6.
Zhao, Y. et al. (2013) The unique mode of action of a divergent member of the ABA-receptor protein family in ABA and stress signaling. *Cell Res*, 23(12):1380-1395.
Zhao, Y. et al. (2014) The ABA receptor PYL8 promotes lateral root growth by enhancing MYB77-dependent transcription of auxin-responsive genes. *Sci Signal*, 7(328):ra53.

* cited by examiner

A

B

C

| Treatment | 1/2 MS | | 100 μM ABA for 1 hour | | 0.8 M Mannitol for 30 min | |
|---|---|---|---|---|---|---|
| Symbol | Unique peptides | Coverage | Unique peptides | Coverage | Unique peptides | Coverage |
| PYL9 | 12 | 81.82 | 11 | 81.82 | 12 | 85.56 |
| HAB2 | 12 | 33.07 | 9 | 30.92 | 14 | 38.75 |
| PP2CA | 5 | 24.31 | 11 | 49.37 | 10 | 47.87 |
| ABI1 | 2 | 8.29 | 7 | 19.35 | 8 | 23.73 |

D

SEQUENCE LISTING

```
<160> NUMBER OF SEQ ID NOS: 106

<210> SEQ ID NO 1
<211> LENGTH: 28
<212> TYPE: DNA
<213> ORGANISM: Artificial Sequence
<220> FEATURE:
<223> OTHER INFORMATION: PYR1-EcoRIF

<400> SEQUENCE: 1

cggaattcat gccttcggag ttaacacc                                         28


<210> SEQ ID NO 2
<211> LENGTH: 26
<212> TYPE: DNA
<213> ORGANISM: Artificial Sequence
<220> FEATURE:
<223> OTHER INFORMATION: PYR1-SallR

<400> SEQUENCE: 2

gtgtcgactc acgtcacctg agaacc                                           26


<210> SEQ ID NO 3
<211> LENGTH: 29
<212> TYPE: DNA
<213> ORGANISM: Artificial Sequence
<220> FEATURE:
<223> OTHER INFORMATION: PYL1-BamHF

<400> SEQUENCE: 3

gcggatccat ggcgaattca gagtcctcc                                        29


<210> SEQ ID NO 4
<211> LENGTH: 30
<212> TYPE: DNA
<213> ORGANISM: Artificial Sequence
<220> FEATURE:
<223> OTHER INFORMATION: PYL1-SallR

<400> SEQUENCE: 4

gtgtcgactt acctaacctg agaagagaag                                       30


<210> SEQ ID NO 5
<211> LENGTH: 27
```

```
<212> TYPE: DNA
<213> ORGANISM: Artificial Sequence
<220> FEATURE:
<223> OTHER INFORMATION: PYL2-EcoRIF

<400> SEQUENCE: 5

cggaattcat gagctcatcc ccggccg                                           27


<210> SEQ ID NO 6
<211> LENGTH: 28
<212> TYPE: DNA
<213> ORGANISM: Artificial Sequence
<220> FEATURE:
<223> OTHER INFORMATION: PYL2-SallR

<400> SEQUENCE: 6

gtgtcgactt attcatcatc atgcatag                                          28


<210> SEQ ID NO 7
<211> LENGTH: 27
<212> TYPE: DNA
<213> ORGANISM: Artificial Sequence
<220> FEATURE:
<223> OTHER INFORMATION: PYL3-EcoRIF

<400> SEQUENCE: 7

cggaattcat gaatcttgct ccaatcc                                           27


<210> SEQ ID NO 8
<211> LENGTH: 26
<212> TYPE: DNA
<213> ORGANISM: Artificial Sequence
<220> FEATURE:
<223> OTHER INFORMATION: PYL3-SallR

<400> SEQUENCE: 8

gtgtcgactc aggtcggaga agccgt                                            26


<210> SEQ ID NO 9
<211> LENGTH: 28
<212> TYPE: DNA
<213> ORGANISM: Artificial Sequence
<220> FEATURE:
<223> OTHER INFORMATION: PYL4-EcoRIF

<400> SEQUENCE: 9

cggaattcat gcttgccgtt caccgtcc                                          28


<210> SEQ ID NO 10
<211> LENGTH: 27
<212> TYPE: DNA
<213> ORGANISM: Artificial Sequence
<220> FEATURE:
<223> OTHER INFORMATION: PYL4-SallR

<400> SEQUENCE: 10

gtgtcgactc acagagacat cttcttc                                           27


<210> SEQ ID NO 11
<211> LENGTH: 27
<212> TYPE: DNA
<213> ORGANISM: Artificial Sequence
<220> FEATURE:
<223> OTHER INFORMATION: PYL5-EcoRIF

<400> SEQUENCE: 11
```

-continued cggaattcat gaggtcaccg gtgcaac 27

<210> SEQ ID NO 12
<211> LENGTH: 28
<212> TYPE: DNA
<213> ORGANISM: Artificial Sequence
<220> FEATURE:
<223> OTHER INFORMATION: PYL5-SalIR

<400> SEQUENCE: 12
gtgtcgactt attgccggtt ggtacttc 28

<210> SEQ ID NO 13
<211> LENGTH: 26
<212> TYPE: DNA
<213> ORGANISM: Artificial Sequence
<220> FEATURE:
<223> OTHER INFORMATION: PYL6-EcoRIF

<400> SEQUENCE: 13
cggaattcat gccaacgtcg atacag 26

<210> SEQ ID NO 14
<211> LENGTH: 25
<212> TYPE: DNA
<213> ORGANISM: Artificial Sequence
<220> FEATURE:
<223> OTHER INFORMATION: PYL6-SalIR

<400> SEQUENCE: 14
gtgtcgactt acgagaattt agaag 25

<210> SEQ ID NO 15
<211> LENGTH: 27
<212> TYPE: DNA
<213> ORGANISM: Artificial Sequence
<220> FEATURE:
<223> OTHER INFORMATION: PYL7-EcoRIF

<400> SEQUENCE: 15
cggaattcat ggagatgatc ggaggag 27

<210> SEQ ID NO 16
<211> LENGTH: 27
<212> TYPE: DNA
<213> ORGANISM: Artificial Sequence
<220> FEATURE:
<223> OTHER INFORMATION: PYL7-SalIR

<400> SEQUENCE: 16
gtgtcgactc aaaggttggt ttctgta 27

<210> SEQ ID NO 17
<211> LENGTH: 29
<212> TYPE: DNA
<213> ORGANISM: Artificial Sequence
<220> FEATURE:
<223> OTHER INFORMATION: PYL8-EcoRIF

<400> SEQUENCE: 17
cggaattcat ggaagctaac gggattgag 29

<210> SEQ ID NO 18
<211> LENGTH: 31
<212> TYPE: DNA
<213> ORGANISM: Artificial Sequence
<220> FEATURE:
<223> OTHER INFORMATION: PYL8-SallR

<400> SEQUENCE: 18
gtgtcgactt agactctcga ttctgtcgtg t 31

<210> SEQ ID NO 19
<211> LENGTH: 28
<212> TYPE: DNA
<213> ORGANISM: Artificial Sequence
<220> FEATURE:
<223> OTHER INFORMATION: PYL9-EcoRIF

<400> SEQUENCE: 19
cggaattcat gatggacggc gttgaagg 28

<210> SEQ ID NO 20
<211> LENGTH: 26
<212> TYPE: DNA
<213> ORGANISM: Artificial Sequence
<220> FEATURE:
<223> OTHER INFORMATION: PYL9-SallR

<400> SEQUENCE: 20
gtgtcgactc actgattaat gtcctg 26

<210> SEQ ID NO 21
<211> LENGTH: 30
<212> TYPE: DNA
<213> ORGANISM: Artificial Sequence
<220> FEATURE:
<223> OTHER INFORMATION: PYL10-EcoRIF

<400> SEQUENCE: 21
cggaattcat gaaaacatct caagaacagc 30

<210> SEQ ID NO 22
<211> LENGTH: 28
<212> TYPE: DNA
<213> ORGANISM: Artificial Sequence
<220> FEATURE:
<223> OTHER INFORMATION: PYL10-SallR

<400> SEQUENCE: 22
gtgtcgactt aagtgagctc catcatct 28

<210> SEQ ID NO 23
<211> LENGTH: 29
<212> TYPE: DNA
<213> ORGANISM: Artificial Sequence
<220> FEATURE:
<223> OTHER INFORMATION: PYL11-EcoRIF

<400> SEQUENCE: 23
cggaattcat ggaaacttct caaaaatat 29

<210> SEQ ID NO 24
<211> LENGTH: 26
<212> TYPE: DNA
<213> ORGANISM: Artificial Sequence
<220> FEATURE:
<223> OTHER INFORMATION: PYL11-SaIIR

<400> SEQUENCE: 24
gtgtcgactt acaactttag atgagc 26

-continued

<210> SEQ ID NO 25
<211> LENGTH: 29
<212> TYPE: DNA
<213> ORGANISM: Artificial Sequence
<220> FEATURE:
<223> OTHER INFORMATION: PYL12-EcoRIF

<400> SEQUENCE: 25
cggaattcat gaacggtgac gaaacaaag 29

<210> SEQ ID NO 26
<211> LENGTH: 28
<212> TYPE: DNA
<213> ORGANISM: Artificial Sequence
<220> FEATURE:
<223> OTHER INFORMATION: PYL12-SaIIR

<400> SEQUENCE: 26
gtgtcgactc atatcttctt ctccatag 28

<210> SEQ ID NO 27
<211> LENGTH: 30
<212> TYPE: DNA
<213> ORGANISM: Artificial Sequence
<220> FEATURE:
<223> OTHER INFORMATION: PYL13-EcoRIF

<400> SEQUENCE: 27
cggaattcat ggaaagttct aagcaaaaac 30

<210> SEQ ID NO 28
<211> LENGTH: 27
<212> TYPE: DNA
<213> ORGANISM: Artificial Sequence
<220> FEATURE:
<223> OTHER INFORMATION: PYL13-SaIIR

<400> SEQUENCE: 28
gtgtcgactt acttcatcat tttcttt 27

<210> SEQ ID NO 29
<211> LENGTH: 30
<212> TYPE: DNA
<213> ORGANISM: Artificial Sequence
<220> FEATURE:
<223> OTHER INFORMATION: RD29A Promoter-HindF

<400> SEQUENCE: 29
cgaagcttgt aaacgaatat tttgtatgtt 30

<210> SEQ ID NO 30
<211> LENGTH: 29
<212> TYPE: DNA
<213> ORGANISM: Artificial Sequence
<220> FEATURE:
<223> OTHER INFORMATION: RD29A promoter-XbaIR

<400> SEQUENCE: 30
cgtctagaga gtaaaacaga ggagggtct 29

<210> SEQ ID NO 31
<211> LENGTH: 29
<212> TYPE: DNA
<213> ORGANISM: Artificial Sequence
<220> FEATURE:
<223> OTHER INFORMATION: pGC1 promoter-HindF

<400> SEQUENCE: 31
cgaagctttg gttgcaacag agaggatga 29

<210> SEQ ID NO 32
<211> LENGTH: 29
<212> TYPE: DNA
<213> ORGANISM: Artificial Sequence
<220> FEATURE:
<223> OTHER INFORMATION: pGC1 promoter-XbaIR

<400> SEQUENCE: 32
gctctagagt gaaaatagta cttgtggat 29

<210> SEQ ID NO 33
<211> LENGTH: 30
<212> TYPE: DNA
<213> ORGANISM: Artificial Sequence
<220> FEATURE:
<223> OTHER INFORMATION: RBCS1A promoter-HindF

<400> SEQUENCE: 33
cgaagcttgg attattggtc aacaaattct 30

<210> SEQ ID NO 34
<211> LENGTH: 29
<212> TYPE: DNA
<213> ORGANISM: Artificial Sequence
<220> FEATURE:
<223> OTHER INFORMATION: RBCS1A promoter-XbaIR

<400> SEQUENCE: 34
gctctagaag tgtggatatg tgtgaggtt 29

<210> SEQ ID NO 35
<211> LENGTH: 30
<212> TYPE: DNA
<213> ORGANISM: Artificial Sequence
<220> FEATURE:
<223> OTHER INFORMATION: ROP11 promoter-EcoRVF

<400> SEQUENCE: 35
cggatatcgg attattggtc aacaaattct 30

<210> SEQ ID NO 36
<211> LENGTH: 29
<212> TYPE: DNA
<213> ORGANISM: Artificial Sequence
<220> FEATURE:
<223> OTHER INFORMATION: ROP11 promoter-XbaIR

<400> SEQUENCE: 36
gctctagaag tgtggatatg tgtgaggtt 29

<210> SEQ ID NO 37
<211> LENGTH: 33
<212> TYPE: DNA
<213> ORGANISM: Artificial Sequence
<220> FEATURE:
<223> OTHER INFORMATION: PYL9F-Sall

<400> SEQUENCE: 37
gcctgtcgac gagttgtgtg tgtgttaatg tta 33

<210> SEQ ID NO 38

<211> LENGTH: 33
<212> TYPE: DNA
<213> ORGANISM: Artificial Sequence
<220> FEATURE:
<223> OTHER INFORMATION: PYL9genoR-ApoI

<400> SEQUENCE: 38
gcctgggccc ctgagtaatg tcctgagaag cca 33

<210> SEQ ID NO 39
<211> LENGTH: 33
<212> TYPE: DNA
<213> ORGANISM: Artificial Sequence
<220> FEATURE:
<223> OTHER INFORMATION: SAG12proF-BamHI

<400> SEQUENCE: 39
gaggatccga atacttagcg taatgaagtt cac 33

<210> SEQ ID NO 40
<211> LENGTH: 34
<212> TYPE: DNA
<213> ORGANISM: Artificial Sequence
<220> FEATURE:
<223> OTHER INFORMATION: SAG12proR-NcoI

<400> SEQUENCE: 40
cttccatggt ttagtcctac atcaacctga aatc 34

<210> SEQ ID NO 41
<211> LENGTH: 28
<212> TYPE: DNA
<213> ORGANISM: Artificial Sequence
<220> FEATURE:
<223> OTHER INFORMATION: ORE1proF-BamHI

<400> SEQUENCE: 41
gaggatcctt tacggcaaag tgttgacc 28

<210> SEQ ID NO 42
<211> LENGTH: 36
<212> TYPE: DNA
<213> ORGANISM: Artificial Sequence
<220> FEATURE:
<223> OTHER INFORMATION: ORE1proR-NcoI

<400> SEQUENCE: 42
cttccatggt ttatcctaat agggtttcta aaaatg 36

<210> SEQ ID NO 43
<211> LENGTH: 56
<212> TYPE: DNA
<213> ORGANISM: Artificial Sequence
<220> FEATURE:
<223> OTHER INFORMATION: pHBT-AB15F

<400> SEQUENCE: 43
cggctccctc tccccttgct ccgtggatcc atggtaacta gagaaacgaa gttgac 56

<210> SEQ ID NO 44
<211> LENGTH: 52
<212> TYPE: DNA
<213> ORGANISM: Artificial Sequence
<220> FEATURE:
<223> OTHER INFORMATION: pHBT-AB15R

<400> SEQUENCE: 44

-continued gtagtctgga acgtcgtatg ggtaaggcct ttagagtgga caactcgggt tc 52

<210> SEQ ID NO 45
<211> LENGTH: 58
<212> TYPE: DNA
<213> ORGANISM: Artificial Sequence
<220> FEATURE:
<223> OTHER INFORMATION: pHBT-EELF

<400> SEQUENCE: 45
cggctccctc tccccttgct ccgtggatcc atgggttcta ttagaggaaa cattgaag 58

<210> SEQ ID NO 46
<211> LENGTH: 54
<212> TYPE: DNA
<213> ORGANISM: Artificial Sequence
<220> FEATURE:
<223> OTHER INFORMATION: pHBT-EELR

<400> SEQUENCE: 46
gtagtctgga acgtcgtatg ggtaaggcct tcagagagaa gcagagtttg ttcg 54

<210> SEQ ID NO 47
<211> LENGTH: 55
<212> TYPE: DNA
<213> ORGANISM: Artificial Sequence
<220> FEATURE:
<223> OTHER INFORMATION: pHBT-AREB3F

<400> SEQUENCE: 47
cggctccctc tccccttgct ccgtggatcc atggattctc agaggggtat tgttg 55

<210> SEQ ID NO 48
<211> LENGTH: 50
<212> TYPE: DNA
<213> ORGANISM: Artificial Sequence
<220> FEATURE:
<223> OTHER INFORMATION: pHBT-AREB3R

<400> SEQUENCE: 48
gtagtctgga acgtcgtatg ggtaaggcct tcagaaagga gccgagcttg 50

<210> SEQ ID NO 49
<211> LENGTH: 57
<212> TYPE: DNA
<213> ORGANISM: Artificial Sequence
<220> FEATURE:
<223> OTHER INFORMATION: pHBT-ORE1F

<400> SEQUENCE: 49
cggctccctc tccccttgct ccgtggatcc atggattacg aggcatcaag aatcgtc 57

<210> SEQ ID NO 50
<211> LENGTH: 52
<212> TYPE: DNA
<213> ORGANISM: Artificial Sequence
<220> FEATURE:
<223> OTHER INFORMATION: pHBT-ORE1R

<400> SEQUENCE: 50
gtagtctgga acgtcgtatg ggtaaggcct tcagaaattc caaacgcaat cc 52

<210> SEQ ID NO 51
<211> LENGTH: 57
<212> TYPE: DNA

<213> ORGANISM: Artificial Sequence
<220> FEATURE:
<223> OTHER INFORMATION: pHBT-ORS1F

<400> SEQUENCE: 51
cggctccctc tccccttgct ccgtggatcc atggattaca aggtatcaag aagtggg 57

<210> SEQ ID NO 52
<211> LENGTH: 54
<212> TYPE: DNA
<213> ORGANISM: Artificial Sequence
<220> FEATURE:
<223> OTHER INFORMATION: pHBT-ORS1R

<400> SEQUENCE: 52
gtagtctgga acgtcgtatg ggtaaggcct tcagaatttc caaacgcaat caag 54

<210> SEQ ID NO 53
<211> LENGTH: 54
<212> TYPE: DNA
<213> ORGANISM: Artificial Sequence
<220> FEATURE:
<223> OTHER INFORMATION: pHBT-AtNAPF

<400> SEQUENCE: 53
cggctccctc tccccttgct ccgtggatcc atggaagtaa cttcccaatc tacc 54

<210> SEQ ID NO 54
<211> LENGTH: 54
<212> TYPE: DNA
<213> ORGANISM: Artificial Sequence
<220> FEATURE:
<223> OTHER INFORMATION: pHBT-AtNAPR

<400> SEQUENCE: 54
gtagtctgga acgtcgtatg ggtaaggcct ctaaaactta aacatcgctt gacg 54

<210> SEQ ID NO 55
<211> LENGTH: 52
<212> TYPE: DNA
<213> ORGANISM: Artificial Sequence
<220> FEATURE:
<223> OTHER INFORMATION: pHBT-RAV1F

<400> SEQUENCE: 55
cggctccctc tccccttgct ccgtggatcc atggaatcga gtagcgttga tg 52

<210> SEQ ID NO 56
<211> LENGTH: 50
<212> TYPE: DNA
<213> ORGANISM: Artificial Sequence
<220> FEATURE:
<223> OTHER INFORMATION: pHBT-RAV1R

<400> SEQUENCE: 56
gtagtctgga acgtcgtatg ggtaaggcct ttacgaggcg tgaaagatgc 50

<210> SEQ ID NO 57
<211> LENGTH: 52
<212> TYPE: DNA
<213> ORGANISM: Artificial Sequence
<220> FEATURE:
<223> OTHER INFORMATION: 6P1-RAV1F

<400> SEQUENCE: 57
gaagttctgt tccaggggcc cctgggatcc atggaatcga gtagcgttga tg 52

<210> SEQ ID NO 58
<211> LENGTH: 50
<212> TYPE: DNA
<213> ORGANISM: Artificial Sequence
<220> FEATURE:
<223> OTHER INFORMATION: 6P1-RAV1R

<400> SEQUENCE: 58
atgcggccgc tcgagtcgac ccgggaattc ttacgaggcg tgaaagatgc 50

<210> SEQ ID NO 59
<211> LENGTH: 58
<212> TYPE: DNA
<213> ORGANISM: Artificial Sequence
<220> FEATURE:
<223> OTHER INFORMATION: 6P1-EELF

<400> SEQUENCE: 59
gaagttctgt tccaggggcc cctgggatcc atgggttcta ttagaggaaa cattgaag 58

<210> SEQ ID NO 60
<211> LENGTH: 54
<212> TYPE: DNA
<213> ORGANISM: Artificial Sequence
<220> FEATURE:
<223> OTHER INFORMATION: 6P1-EELR

<400> SEQUENCE: 60
atgcggccgc tcgagtcgac ccgggaattc tcagagagaa gcagagtttg ttcg 54

<210> SEQ ID NO 61
<211> LENGTH: 22
<212> TYPE: DNA
<213> ORGANISM: Artificial Sequence
<220> FEATURE:
<223> OTHER INFORMATION: RD29A promoter F

<400> SEQUENCE: 61
cacgcgtaga gagcaaaatg ac 22

<210> SEQ ID NO 62
<211> LENGTH: 23
<212> TYPE: DNA
<213> ORGANISM: Artificial Sequence
<220> FEATURE:
<223> OTHER INFORMATION: PYL9-R

<400> SEQUENCE: 62
agtagcaagt ctcatccttt gtg 23

<210> SEQ ID NO 63
<211> LENGTH: 20
<212> TYPE: DNA
<213> ORGANISM: Artificial Sequence
<220> FEATURE:
<223> OTHER INFORMATION: ORE1qF

<400> SEQUENCE: 63
aatgaagctg ttgcttgacg 20

<210> SEQ ID NO 64
<211> LENGTH: 20
<212> TYPE: DNA
<213> ORGANISM: Artificial Sequence
<220> FEATURE:

<223> OTHER INFORMATION: ORE1qR

<400> SEQUENCE: 64
agaaattcca aacgcaatcc 20

<210> SEQ ID NO 65
<211> LENGTH: 21
<212> TYPE: DNA
<213> ORGANISM: Artificial Sequence
<220> FEATURE:
<223> OTHER INFORMATION: AtNAPqF

<400> SEQUENCE: 65
tggctcattt gttggaaatg g 21

<210> SEQ ID NO 66
<211> LENGTH: 22
<212> TYPE: DNA
<213> ORGANISM: Artificial Sequence
<220> FEATURE:
<223> OTHER INFORMATION: AtNAPqR

<400> SEQUENCE: 66
gacgatgatg gtttaagatc tc 22

<210> SEQ ID NO 67
<211> LENGTH: 22
<212> TYPE: DNA
<213> ORGANISM: Artificial Sequence
<220> FEATURE:
<223> OTHER INFORMATION: SAG12qF

<400> SEQUENCE: 67
acaaaggcga agacgctact tg 22

<210> SEQ ID NO 68
<211> LENGTH: 24
<212> TYPE: DNA
<213> ORGANISM: Artificial Sequence
<220> FEATURE:
<223> OTHER INFORMATION: SAG12qR

<400> SEQUENCE: 68
taaccgggac atcctcataa cctg 24

<210> SEQ ID NO 69
<211> LENGTH: 24
<212> TYPE: DNA
<213> ORGANISM: Artificial Sequence
<220> FEATURE:
<223> OTHER INFORMATION: SAG13qF

<400> SEQUENCE: 69
gcatcgtgct catatcctct gctg 24

<210> SEQ ID NO 70
<211> LENGTH: 24
<212> TYPE: DNA
<213> ORGANISM: Artificial Sequence
<220> FEATURE:
<223> OTHER INFORMATION: SAG13qR

<400> SEQUENCE: 70
gccagctgat tcatggctcc tttg 24

<210> SEQ ID NO 71
<211> LENGTH: 20
<212> TYPE: DNA
<213> ORGANISM: Artificial Sequence
<220> FEATURE:
<223> OTHER INFORMATION: KCS2-rtF

<400> SEQUENCE: 71
caacctcgct ttccaacaaa 20

<210> SEQ ID NO 72
<211> LENGTH: 20
<212> TYPE: DNA
<213> ORGANISM: Artificial Sequence
<220> FEATURE:
<223> OTHER INFORMATION: KCS2-rtR

<400> SEQUENCE: 72
tccggttttc tcaagcactg 20

<210> SEQ ID NO 73
<211> LENGTH: 20
<212> TYPE: DNA
<213> ORGANISM: Artificial Sequence
<220> FEATURE:
<223> OTHER INFORMATION: CER1-rtF

<400> SEQUENCE: 73
aggtcgacag ggagaccaac 20

<210> SEQ ID NO 74
<211> LENGTH: 20
<212> TYPE: DNA
<213> ORGANISM: Artificial Sequence
<220> FEATURE:
<223> OTHER INFORMATION: CER1-rtR

<400> SEQUENCE: 74
ataagcgctg ccatcaacac 20

<210> SEQ ID NO 75
<211> LENGTH: 20
<212> TYPE: DNA
<213> ORGANISM: Artificial Sequence
<220> FEATURE:
<223> OTHER INFORMATION: LTP3-rtF

<400> SEQUENCE: 75
tggctccatg tgcaacctat 20

<210> SEQ ID NO 76
<211> LENGTH: 20
<212> TYPE: DNA
<213> ORGANISM: Artificial Sequence
<220> FEATURE:
<223> OTHER INFORMATION: LTP3-rtR

<400> SEQUENCE: 76
ggactggatg catctgcaag 20

<210> SEQ ID NO 77
<211> LENGTH: 20
<212> TYPE: DNA
<213> ORGANISM: Artificial Sequence
<220> FEATURE:
<223> OTHER INFORMATION: WSD1-rtF

<400> SEQUENCE: 77
gcttggtggt tgtttgttgg 20

<210> SEQ ID NO 78
<211> LENGTH: 20
<212> TYPE: DNA
<213> ORGANISM: Artificial Sequence
<220> FEATURE:
<223> OTHER INFORMATION: WSD1-rtR

<400> SEQUENCE: 78
tcgggttacc cataagaggg 20

<210> SEQ ID NO 79
<211> LENGTH: 23
<212> TYPE: DNA
<213> ORGANISM: Artificial Sequence
<220> FEATURE:
<223> OTHER INFORMATION: SWEET15RTF

<400> SEQUENCE: 79
gagagaaagc tttagggttt caa 23

<210> SEQ ID NO 80
<211> LENGTH: 20
<212> TYPE: DNA
<213> ORGANISM: Artificial Sequence
<220> FEATURE:
<223> OTHER INFORMATION: SWEET15RTR

<400> SEQUENCE: 80
acgtttccta agatgccgaa 20

<210> SEQ ID NO 81
<211> LENGTH: 22
<212> TYPE: DNA
<213> ORGANISM: Artificial Sequence
<220> FEATURE:
<223> OTHER INFORMATION: PYL9qF

<400> SEQUENCE: 81
cctcttcatc tcgtttggtc ac 22

<210> SEQ ID NO 82
<211> LENGTH: 22
<212> TYPE: DNA
<213> ORGANISM: Artificial Sequence
<220> FEATURE:
<223> OTHER INFORMATION: PYL9qR

<400> SEQUENCE: 82
ctctaagact gccgatttca gg 22

<210> SEQ ID NO 83
<211> LENGTH: 22
<212> TYPE: DNA
<213> ORGANISM: Artificial Sequence
<220> FEATURE:
<223> OTHER INFORMATION: RD29A-F

<400> SEQUENCE: 83
cacgcgtaga gagcaaaatg ac 22

<210> SEQ ID NO 84
<211> LENGTH: 23

<212> TYPE: DNA
<213> ORGANISM: Artificial Sequence
<220> FEATURE:
<223> OTHER INFORMATION: PYL9-R

<400> SEQUENCE: 84
agtagcaagt ctcatccttt gtg 23

<210> SEQ ID NO 85
<211> LENGTH: 890
<212> TYPE: DNA
<213> ORGANISM: Arabidopsis thaliana

<400> SEQUENCE: 85
tctctctttc aagtttcaac aaacaatatc aatggcgaat tcagagtcct cctcctcacc 60
agtaaacgaa gaagagaaca gccagagaat ctcaacactc catcaccaaa ccatgccttc 120
cgatttaact caagacgaat tcacccaact ctcccaatca atcgccgagt tccacacgta 180
ccaactcggt aacggccgtt gctcatctct cctagctcag cgaatccacg cgccgccgga 240
aacagtatgg tccgtggtga gacgtttcga taggccacag atttacaaac acttcatcaa 300
aagctgtaac gtgagtgaag atttcgagat gcgagtggga tgcacgcgcg acgtgaacgt 360
gataagtgga ttaccggcga atacgtctcg agagagatta gatctgttgg acgatgatcg 420
gagagtgact gggtttagta taaccggtgg tgaacatagg ctgaggaatt ataaatcggt 480
tacgacggtt catagatttg agaaagaaga agaagaagaa aggatctgga ccgttgtttt 540
ggaatcttat gttgttgatg taccggaagg taattcggag gaagatacga gattgtttgc 600
tgatacggtt attagattga atcttcagaa acttgcttcg atcactgaag ctatgaaccg 660
gaacaacaac aacaacaact cttctcaggt taggtaatga tgaaatttgg gggaaagaaa 720
aatgtttcta aattggggga gttttaattt ttattttgat ttgtaaaacg tttttttct 780 tctcttgaat tgtaatttcc ttgtttgatt ttatggttat gttttatttt ttaaaaaaaa 840
tcagtctcct ggataattgg aatggtcgag ataggttaaa tttaataaca 890

<210> SEQ ID NO 86
<211> LENGTH: 883
<212> TYPE: DNA
<213> ORGANISM: Arabidopsis thaliana

<400> SEQUENCE: 86
ataacacatt atatatctat atatatacgt atgtcaagag aattagtcct agtttcgtac 60
acaattttct tctcaaaatt aaagtacacc caaaaccatg aatcttgctc caatccatga 120
tccatcatca tcatcaacaa caacaacatc atcgtcaaca ccatacggat taacaaagga 180
cgagttctca acactagact ccatcatccg aacacaccac acgttcccaa gatcgccaaa 240
cacgtgcaca tcactcatag cacaccgtgt agacgcaccg gcacatgcca tatggagatt 300
cgtccgcgac ttcgccaatc caaacaaata caaacacttc atcaagagtt gcaccatcag 360
agttaacggt aacggcatca aagagattaa agttgggact ataagggaag ttagcgtggt 420
ctctggtctt ccagcgtcaa caagcgttga gatactcgaa gttcttgacg aagagaaacg 480
aatcttgagt tttcgtgttc ttggaggaga acaccggtta aataattacc ggtcggttac 540
atcggtcaac gagttcgtcg tcttggaaaa ggataagaag aagagagtgt atagtgtggt 600
attggagtct tacattgttg atataccaca aggtaacacg gaagaagata caaggatgtt 660
tgtggatacg gtcgttaagt cgaatctaca gaatctcgcc gtcatttcca cggcttctcc 720
gacctgaaag tgtttgtgtt gaaaatgtca tgtgtggtgt atataatggg ccataaatgg 780
gccgattatt tgttcaacgg atgtgtttgt gtggaatgtg aggtgtgtat ataaaactat 840
gggctataat gggcttagta attattatat aaggaaatcc ctg 883

<210> SEQ ID NO 87
<211> LENGTH: 1071
<212> TYPE: DNA
<213> ORGANISM: Arabidopsis thaliana

<400> SEQUENCE: 87
attacatgta aatatctctc attaatacaa cctcacgaag aaaaccattt gttttcttag 60
agagagccaa gaatattaaa agagatatag agaaaagatt tgctttaata atgccaacgt 120
cgatacagtt tcagagatcc tccaccgccg cagaagcagc caacgccacc gtaagaaact 180
atccccacca ccatcagaaa caggttcaaa aagtgagcct cacgcgcggg atggctgatg 240
tgccggagca cgtggagctt tcccacacgc acgtggttgg tccttctcag tgcttctccg 300
tcgtggtaca agacgtggag gctccggttt ccacagtctg gtcgatccta agccgcttcg 360
aacaccctca agcgtacaaa cacttcgtga aaagctgcca cgtggttatc ggagacggtc 420
gagaggttgg gtcggtgaga gaggtcagag tcgtctctgg tctccccgcg gcgtttagct 480
tagagcggct tgagatcatg gacgatgatc gccacgtcat cagtttcagc gtcgttggtg 540
gggaccacag actcatgaac tacaagtcgg tgacgacggt gcatgagtcg gaggaggact 600
ccgacggcaa gaagaggaca cgtgtcgttg agtcatacgt cgttgacgta ccggcgggta 660
acgataagga agagacttgt agctttgctg atactatagt acggtgcaac ttgcaatcgc 720
tggctaaact cgccgagaac acttctaaat tctcgtaatt acattttttc aatcttttta 780
tttttatttt attttctata tttctctctt tcaaaattta tcttttattt ttgggattct 840
cgaggtggtt ttggatttta agatttaagt atttaactat cgtcggggat ttttcgaaac 900
taaaacaaaa aacaagaatt atatcaaaca agatggtttt ggtttttcga agttagggtt 960
tttagggtct gttaaatgta tgtctcaacg atactttggt tttaccctta aaaccatttc 1020
ttcttgtaca gctctcgtag ctttattata taaacattga ttgtttagtt a 1071

<210> SEQ ID NO 88
<211> LENGTH: 1166
<212> TYPE: DNA
<213> ORGANISM: Arabidopsis thaliana

<400> SEQUENCE: 88
agcctaacca accaaacata aataaaaatc gaagctttac tttgtttgct tctattatat 60
ccacttccaa caagattcct caaaaggaaa gaagagaaag aagataagag atatctggtt 120
ggtcggagat ggagatgatc ggaggagacg atacagatac agagatgtac ggagctctag 180
tgacggcaca gtccttaagg ttgcgtcatc ttcaccactg cagagagaac cagtgtacct 240
ctgttctcgt caaatacatt caagctcctg ttcatcttgt ttggtcactg gtgcggagat 300
ttgatcagcc gcagaaatac aaaccattta taagcagatg cactgtaaat ggtgatcctg 360
agatcggttg tctcagagaa gtaaatgtca aatctggtct tccagcaacc accagtacag 420
agagattgga acagcttgat gatgaagaac acatcctcgg tatcaacatc attggtggtg 480
atcatagact taagaattac tcttcgatct tgactgtgca tccggagatg attgatggaa 540
ggtcaggaac tatggtgatg gagtcttttg ttgtggatgt tcctcaaggc aacaccaaag 600
atgatacatg ttacttcgtg gaatcactca taaagtgtaa cctcaaatcc ttggcttgtg 660

-continued

```
tctctgaaag attggctgct caagacatta ccaattccat cgcaactttc tgtaacgctt    720

ccaatggata cagagagaag aatcatacag aaaccaacct ttgaagattt ggctagatta    780

gtcccacgaa caaactcagt gaaggaaatt tagattcata gaagcacgtg tgatcatgct    840

tctctgctgc tttactcaga tcagctccat gggccatttt cgagcatgca gtcaaagttt    900

tgatgtaatt tgttttctgg tgtttgttgg acagtgtctg tatttacgca ccattgttag    960

aaaaaacaga gctaggtagt atctatatta tcaccaagag tcgttgcagg aacattttcc   1020

gtctctgaaa tgatgaaccc ttgccccttc ttgtaaaaca atctcacggt ttctcaaaac   1080

cgacatgtat ttggctacgg tgtggctatc agaacatata ttcgtgtttt tgaccactct   1140

tataggagct aagcctttct tcttga                                        1166
```

<210> SEQ ID NO 89
<211> LENGTH: 1000
<212> TYPE: DNA
<213> ORGANISM: Arabidopsis thaliana

<400> SEQUENCE: 89

```
attatgtcgg tgggttcatt aaaagaaacc aaaaaacata aacaagtaat tttgttttgg     60

cataacgaag catcttcttc ttcttccttg tatttattat ccatttccag agattctccc    120

ttgtgagata acaacgaaga acgaaagaga gagagagaga gagagatatg atggacggcg    180

ttgaaggcgg cacggcgatg tacggtggtc tcgagacggt gcaatacgta cggacgcatc    240

atcaacatct gtgcagagaa aaccagtgta cctctgctct tgtcaaacac atcaaagctc    300

ctcttcatct cgtttggtca cttgtacgga gatttgatca gccgcagaaa tacaaaccgt    360

ttgtgagcag atgtacagta atcggtgatc ctgaaatcgg cagtcttaga gaagtcaatg    420

ttaaatctgg tcttcctgca acaacatcta ctgagagatt agaacttctt gatgatgaag    480

aacacatcct cggtatcaaa atcatcggtg gtgatcacag acttaagaat tactcgtcga    540

ttttgacggt tcatccggag ataatcgagg gaagagcagg aacgatggtg attgaatcgt    600

ttgtagttga tgttcctcaa ggtaacacaa aggatgagac ttgctacttt gttgaagcac    660

ttatcagatg taatctcaag tcactagcag atgtttctga aagattggct tctcaggaca    720

ttactcagtg aactacataa tcaatgaaca agggcattga agtgaagtat caattccagt    780

ttgtgatata atcaatattc ttcaggattt ttttggtttg gcctagatat atatatagat    840

atctatcctc ggtaatgacc agtctaaaaa gatgtacata ttgtcccaat ggtgaagttt    900

tgatgtaaga tatctcctgg tggtttgtta tttgtagata tttttgtaaa caatgtaaat    960

gtgaatggtt tatgatgtat aatatatagt tcacaaaaga                        1000
```

<210> SEQ ID NO 90
<211> LENGTH: 480
<212> TYPE: DNA
<213> ORGANISM: Arabidopsis thaliana

<400> SEQUENCE: 90

```
atgaaaacat ctcaagaaca gcatgtatgc ggttcgacag tagtacaaac tatcaatgct     60

ccgttacctc tagtatggtc gatcctacgt cgatttgata acccaaaaac atttaaacat    120

ttcgtaaaaa cttgtaaact acgctccggc gatggaggag aaggctctgt ccgtgaagtc    180

acggtggttt ccgatcttcc ggcgagtttt agcctagaaa gattagatga acttgacgat    240

gagtctcatg tgatggtgat cagcattatt ggtggtgatc atcgtttggt taattaccag    300
```

-continued tcgaaaacta cggtgtttgt ggcggcggag gaggagaaga cagtggttgt ggagagttat 360
gtggtggatg tgccggaagg aaatactgag gaagaaacta cgttgtttgc tgatactatc 420
gttgggtgta atcttaggtc attggctaag ttatcggaga agatgatgga gctcacttaa 480

<210> SEQ ID NO 91
<211> LENGTH: 486
<212> TYPE: DNA
<213> ORGANISM: Arabidopsis thaliana

<400> SEQUENCE: 91
atggaaactt ctcaaaaata tcatacgtgc ggttccacac tagtacaaac tatagatgct 60
ccactatctc tagtttggtc aattctacgt cggtttgata accctcaagc ctacaaacaa 120
ttcgtgaaaa cgtgcaatct aagctccggc gatggaggag aaggctccgt ccgtgaagtg 180
acggtggttt ccggtcttcc agcggagttc agccgagaga gattagatga acttgacgat 240
gagtctcatg tgatgatgat tagcattata ggtggtgatc atcgtttggt taattaccgg 300
tcgaaaacga tggcgtttgt ggcggcggat acggaggaga agacggtggt ggtggagagt 360
tatgtggtgg atgtgccgga aggaaatagt gaggaggaaa cgacgtcttt tgctgataca 420
atcgttgggt ttaatcttaa gtcattggct aagctctcgg agagggtggc tcatctaaag 480
ttgtaa 486

<210> SEQ ID NO 92
<211> LENGTH: 583
<212> TYPE: DNA
<213> ORGANISM: Arabidopsis thaliana

<400> SEQUENCE: 92
atgaacggtg acgaaacaaa gaaggtggag agcgagtaca tcaagaaaca ccatagacac 60
gagcttgtag agtctcaatg tagctctacg ctcgttaagc acatcaaagc tcctctgcat 120
ctcgtgtggt caattgtgag gagattcgat gaaccacaaa aatacaaacc atttatcagt 180
aggtgtgtgg tacaaggtaa gaagctggag gttggtagcg taagagaagt ggatttgaaa 240
tctggattac cagctactaa aagcactgag gtattagaga ttcttgacga caatgagcat 300
attctcggca tcagaatagt tggtggtgat catagactca agaattattc ttcaaccatt 360
tcgttacatt cggagacgat agacggaaaa acagggacat tggctataga atcgttcgtg 420
gtggatgtgc cggaaggtaa cacaaaggag gagacatgct tcttcgtgga ggctttgatt 480
caatgcaatc tcaattcttt agcagatgtt accgagcgtc tacaagcaga atctatggag 540
aagaagatat gagatgtgac ttgagaatct tttcattcgg aaa 583

<210> SEQ ID NO 93
<211> LENGTH: 841
<212> TYPE: DNA
<213> ORGANISM: Arabidopsis thaliana

<400> SEQUENCE: 93
gagagagtct aaaagctcgt cgtcgtcttc aatggtgaat ctcaaaccaa ttggataaat 60
aaaacaaaac aaaaaaaact tcacaaaaaa aaaaaaaaga tccaaattac aaccatgcct 120
tcggagttaa caccagaaga acgatcggaa ctaaaaaact caatcgccga gttccacaca 180
taccaactcg atccaggaag ctgttcatca ctccacgcgc aacgaatcca cgcgcctccg 240
gaactcgtct ggtcaatcgt acgacgattc gacaaaccac aaacatacaa acacttcatc 300
aaatcctgct ccgtcgaaca aaacttcgag atgcgcgtcg gatgcacgcg cgacgtgatc 360

```
gtcatcagtg gattaccggc gaacacatca acggaaagac tcgatatact cgacgacgaa    420

cggagagtta ccggattcag tatcatcgga ggcgaacata ggctgacgaa ttacaaatcc    480

gttacgacgg tgcatcggtt cgagaaagag aatcggatct ggacggtggt tttggaatct    540

tacgtcgttg atatgccgga aggtaactcg gaggatgata ctcgtatgtt tgctgatacg    600

gttgtgaagc ttaatttgca gaaactcgcg acggttgctg aagctatggc tcgtaactcc    660

ggtgacggaa gtggttctca ggtgacgtga aaatgaagaa aaaaatatga tttaatttct    720

tttattaaaa acaaaatcca gaaatgttat ttatgttgct tcgtataaga ttctcttctt    780

cttttgtctg tttttgcttt tttaacctca tatagtcata tttttaccat tttcttatga    840

t                                                                    841
```

<210> SEQ ID NO 94
<211> LENGTH: 573
<212> TYPE: DNA
<213> ORGANISM: Arabidopsis thaliana

<400> SEQUENCE: 94

```
atgagctcat ccccggccgt gaaaggccta accgatgaag agcagaaaac cctcgaaccg     60

gttatcaaaa cgtaccacca gttcgaacca gacccaacca cgtgcacttc tctcataacc    120

caacgcatcc acgctccggc ctccgtggtt tggcctctta tccgccgctt cgacaacccc    180

gaacgctaca aacactttgt aaaaaggtgc cgtctcatct ccggtgatgg tgacgtcgga    240

agcgtcagag aagtgaccgt aatctccggc ctcccagcct caaccagtac cgagcggctt    300

gagttcgtcg atgacgacca ccgtgttcta agcttcaggg tcgtcggcgg agagcaccga    360

ctcaagaact acaaatcagt gacgtcggtc aatgagttct tgaatcaaga ttccggcaag    420

gtttacacgg tggttcttga atcttacacc gttgatattc ccgagggaaa cacagaggaa    480

gacactaaaa tgtttgtgga cactgtcgtc aaactcaacc ttcagaaact cggagttgcc    540

gccacatctg cacctatgca tgatgatgaa taa                                 573
```

<210> SEQ ID NO 95
<211> LENGTH: 1106
<212> TYPE: DNA
<213> ORGANISM: Arabidopsis thaliana

<400> SEQUENCE: 95

```
aaatcgaaag gcacagccca acttttcgca agtcgctgta aagtttgatt tgcttctttt     60

tatatacaca catacttctc ctccatacac tttcctcttc aatcctcagt ttttttttcta   120

agccctaata ccatctcaaa gaagagatca agatttgaaa tcaagaagac accattactc    180

agatcaacat gcttgccgtt caccgtcctt cttccgccgt atcagacgga gattccgttc    240

agattccgat gatgatcgcg tcgtttcaaa aacgttttcc ttctctctca cgcgactcca    300

cggccgctcg ttttcacaca cacgaggttg gtcctaatca gtgttgctcc gccgttattc    360

aagagatctc cgctccaatc tccaccgttt ggtccgtcgt acgccgcttt gataacccac    420

aagcttacaa acactttctc aaaagctgta gcgtcatcgg cggagacggc gataacgttg    480

gtagcctccg tcaagtccac gtcgtctctg gtctccccgc cgctagctcc accgagagac    540

tcgatatcct cgacgacgaa cgccacgtca tcagcttcag cgttgttggt ggtgaccacc    600

ggctctctaa ctaccgatcc gtaacgaccc ttcacccttc tccgatctcc gggaccgtcg    660

ttgtcgagtc ttacgtcgtt gatgttcctc caggcaacac aaaggaagag acttgtgact    720
```

-continued

```
tcgttgacgt tatcgtacga tgcaatcttc aatctcttgc gaaaatagcc gagaatactg    780

cggctgagag caagaagaag atgtctctgt gatgagtctt tgtcgttgtc gggtagtttc    840

gttagatccg acgtcgtttt ctagattttt agccgtcgtg tgatctatgt tttttcggct    900

tatgtgtgaa aaaaaagtta cattagtgaa ttaatctctc atgcatatca taatccttct    960

tttaattttt gtattttaca tatcccataa agaaccgatt tggatagccc tattccggct   1020

ttcaccaccc aaagataata atattcaaac tgaaagaatg tggttgtgtt gtccgctaat   1080

taaaagtgtg attttcaagt ttaatt                                         1106
```

<210> SEQ ID NO 96
<211> LENGTH: 1197
<212> TYPE: DNA
<213> ORGANISM: Arabidopsis thaliana

<400> SEQUENCE: 96

```
gacagcgaac aagatcaaaa agctagctct cttcttttct catcaaactt atttctctct     60

cgatcgcaat atatacgatt ccataaattc tcccaaaaac aaattaagag atagaggaga    120

gatcatgagg tcaccggtgc aactccaaca cggctcagac gccactaacg gtttccacac    180

gctgcagcct cacgatcaga ccgatggtcc gatcaagaga gtgtgtctca cgcgcggtat    240

gcatgtccct gaacacgttg cgatgcacca cacacacgac gttggtccgg accagtgttg    300

ctcctcggtg gtgcagatga tccacgcgcc gcctgagtcc gtgtgggctc ttgtgcggcg    360

tttcgataat ccgaaggttt acaagaactt catcagacag tgccgtatcg tccaaggcga    420

tggactacac gtcggcgatc tccgggaggt catggtggtc tctggactcc cggcggtctc    480

gagcaccgag aggctcgaga tcttggacga ggagcgtcac gtgataagct ttagtgtcgt    540

tggtggggac cacaggctca agaactaccg atcggtgacg acactacacg cgtcggacga    600

cgaaggtacc gtggtggtgg agtcttacat cgttgatgtg ccgccgggaa acacggagga    660

ggaaactcta agcttcgttg atactatcgt ccggtgcaac cttcagtctc tggctcgaag    720

taccaaccgg caataatctc atctttctta tataaattgc aattatgtat ctaatttttt    780

ttgttgttct atttctttta gatgttcgat cttctttaca aggaagaaaa tttcgagtac    840

cttttctttc tttttaaata gatatatcgg cttagaaaga attgtaattt aatggggatt    900

tctttgggag atttatgttg gaaatttcga agtactgttg gggggattcac aaaactttgg    960

atttggaggg tgttagtact ggtacataaa acattttaag gtgaatctgt taaatgaatt   1020

aatccatttg ttgttttgta catggtatca ttctttgtga cattgtttaa tttcttgtac   1080

tcttttaaat gttactctta accgtttttt tcttttgtgg tttgtaaatg aatatttgat   1140

gcatcggtat tgttaatgat agacttatta atttatttct tcatagtatg taacatt      1197
```

<210> SEQ ID NO 97
<211> LENGTH: 1182
<212> TYPE: DNA
<213> ORGANISM: Arabidopsis thaliana

<400> SEQUENCE: 97

```
tttgttggag gattcgtctc tctctctctc tctttctctt tctctcatct tcttcttatc     60

tccctccaaa gacggcgact gtataatcta tcatttcttc acagtaacgc tttcatcgga    120

agatctcgcc ggaaaaaaac ttctctctga gatcagatct cttacgattc tcagctcaat    180

cttatctttt cctttgttgt gctgcttttc actctcttct gcgcgacgaa tttggccttg    240

tttttgtttt gtttgtcgta tccgacgcgg aggtattgag aaaccgtggc ttaagacgga    300
```

ggaagaagat ggaagctaac gggattgaga acttgacgaa tccgaatcag gaaagagagt 360
ttataaggag acatcataag catgagcttg tggataatca gtgtagctct acgcttgtta 420
aacatatcaa cgctcctgtt catattgtgt ggtcacttgt gagaagattt gatcagccac 480
agaagtataa gccgtttatc agtagatgtg tggtgaaagg aaacatggag attggtacag 540
taagagaagt tgatgtgaaa tctggactac cagcaactag aagcactgag agattggagt 600
tacttgatga caatgagcat attctcagta tcagaatcgt tggtggtgat catagactta 660
agaactattc ttcaatcatc tctcttcacc ccgagactat agaaggaaga ataggaacac 720
ttgtgattga gtcatttgtg gttgatgtac cagaaggaaa cacaaaggat gagacttgtt 780
actttgttga agctttaatc aaatgcaatc ttaaatcttt agctgatatc tctgaacgtc 840
ttgcggttca agacacgaca gaatcgagag tctaaagatc aaaggagtaa gaaactattg 900
aatcagagag attttggttg ccatggatga agctctcaaa gggaaaaaga gagagtgggt 960
gagtttcttt gaggatggac aaggcaaaaa aagtatcatc atttatccag ttacataata 1020
agtttctcat ttgctatttt tggggtcatt tcactttcaa accctctttt taatttcatg 1080
tgtctaattt aatgaatgtg tttttggttt cttctctata gaaccaaaat atgattttgg 1140
agtttagctt tagcaacttg caggaatctt tttacaattt gc 1182

<210> SEQ ID NO 98
<211> LENGTH: 495
<212> TYPE: DNA
<213> ORGANISM: Arabidopsis thaliana

<400> SEQUENCE: 98
atggaaagtt ctaagcaaaa acgatgtcgc tctagcgtag tcgagaccat tgaagcacca 60
ttaccactag tgtggtccat cctacgtagt ttcgacaaac cacaagctta tcaacgtttc 120
gtcaaaagtt gcaccatgcg ctctggcggc ggcggcggca aaggaggaga aggaaaaggc 180
tccgtccggg acgtgacgtt agtctccggc ttcccggcgg atttcagcac ggagaggctc 240
gaagagctag atgatgagtc tcacgtgatg gtggtaagta ttattggcgg taaccatagg 300
cttgttaatt acaaatcgaa aacgaaggtg gtcgcgtcgc cggaggatat ggcaaagaag 360
acggtggtgg tggagagtta cgtggtggat gtgccggaag gaactagcga ggaagataca 420
atattttttg ttgataacat tattcggtat aaccttactt cacttgctaa gctcacaaag 480
aaaatgatga agtaa 495

<210> SEQ ID NO 99
<211> LENGTH: 2500
<212> TYPE: DNA
<213> ORGANISM: Arabidopsis thaliana

<400> SEQUENCE: 99
acaaatatgc aaactagaaa acaatcatca ggaataaagg gtttgattac ttctattgga 60
aagaaaaaaa tctttggaaa atggatcaaa cagaggaacc accactcaac acacaccagc 120
agcacccaga agaagttgaa catcatgaga atggtgcgac taagatgttt aggaaagtaa 180
aggctagagc taagaagttc aagaacagtc tcactaaaca tggacaaagc aatgagcatg 240
agcaagatca tgatttggtt gaagaagatg atgatgatga cgagctagaa cctgaagtga 300
tcgatgcacc aggcgtaaca ggtaaaccta gagaaactaa tgttccagca tcggaggaaa 360
ttattccacc agggacaaag gtgtttcctg tcgtgtcttc cgattacacc aaacccactg 420

-continued

```
aatctgtacc agtacaagag gcctcttacg gacacgatgc accggctcat tctgtaagga    480

cgacgtttac atcggacaag gaagagaaaa gagatgtacc gattcatcat cctctgtccg    540

aattgtcaga cagagaagag agtagagaga ctcatcatga gtcattgaac actccggtct    600

ctctgctttc tggaacagag gatgtaacga gtacgtttgc tccaagtggt gatgatgaat    660

atcttgatgg tcaacggaag gtcaacgtcg agaccccgat aacgttggag gaagagtcgg    720

ctgtttcaga ctatcttagt ggtgtatcta attatcagtc caaagttact gatcccacca    780

aagaagaaac tggaggagta ccggagattg ctgagtcttt tggtaatatg gaagtgactg    840

atgagtctcc tgatcagaag ccaggacaat ttgaaagaga cttgtcgacg agaagcaaag    900

aattcaaaga gtttgatcag gactttgact ctgttctcgg taaggattcg ccggcgaaat    960

ttccaggtga atcaggagtt gttttcccgg tgggctttgg tgacgagtca ggagctgagc   1020

tggaaaaaga ttttccgacg agaagtcatg attttgatat gaagactgaa actggaatgg   1080

acacgaattc tccatcaaga agccatgaat ttgatctgaa gactgaatct ggaaacgaca   1140

agaattctcc gatgggcttt ggtagtgaat caggagctga gctggaaaaa gaatttgatc   1200

agaagaacga ttctggaaga aacgagtatt cgccggaatc tgacggcggt ttaggagctc   1260

cgttgggagg aaattttccg gtgagaagtc atgagttgga tctgaagaac gaatctgata   1320

tcgacaagga tgtgccgacg ggatttgacg gagaaccaga ttttctggcg aagggaagac   1380

ctggatacgg tgaggcatca gaagaggata aatttccggc gagaagtgat gatgtggaag   1440

tagagactga gctgggaaga gacccaaaga cggagactct tgatcaattc tcaccggaac   1500

tttctcatcc taaagaaaga gatgagttta aggagtccag agatgatttt gaggagacga   1560

gagatgagaa aacagaggag ccaaaacaga gcacttacac agagaagttt gcttcaatgc   1620

taggttactc cggagaaatt ccggtgggag atcaaactca agtggcggga actgttgatg   1680

agaagttgac tccggtcaat gagaaggatc aagaaacaga gtctgccgtg acgacgaagt   1740

tacctatctc cggaggtgga agtggagtag aggagcaacg aggggaagat aaaagtgtgt   1800

cgggtagaga ttatgtggcg gagaaactga caactgaaga agaagacaaa gccttttctg   1860

atatggttgc cgagaaactt cagattggag gagaagaaga gaagaaggaa acgacgacaa   1920

aggaagtgga gaagatctct accgagaagg cagcatcgga ggagggtgag gcggtggaag   1980

aggaagtgaa aggaggagga ggaatggttg ggaggattaa aggatggttc ggtggtggtg   2040

cgactgatga ggtgaagcca gaatcgccac attctgttga agaggctcca aaatcatctg   2100

gctggtttgg tggtggtgcg acggaggagg tgaagccaaa atcgcctcat tccgttgaag   2160

agtctccaca atcacttggc tccactgttg ttccggtgca gaaggagctt taagaatatg   2220

agaactgaga ttttcaagtt tcactttgga tgtttatgtg tgttttgttt gacgtctttg   2280

atgtattatg gtataattcc ttgtttgtgt gaaaaaagga catttggtta ataaattgtt   2340

cggctttgga ttaagaagtt cctccatacc agctactagg tctaaagtgg gtaaaatcat   2400

tggatttatt cccttcaaag ttcttagaat tattcacagg attttacatt atgagctagt   2460

agtgtgactt gttgaggtgt tgtctctatc gttaaagttc                         2500
```

<210> SEQ ID NO 100
<211> LENGTH: 1679
<212> TYPE: DNA
<213> ORGANISM: Cauliflower mosaic virus

<400> SEQUENCE: 100

```
gaattcttta gcctttaaat tgctagtttt cgttaaatgg tcataacttg agctatggac     60
```

-continued

```
ctccaaatta aatttcgggc atacgctcaa atcccaaatt acgatacgga gctaccggaa    120

ctgtcaaaat actgatccgg gtccgtttgc taaaaacgtt gaccaaagtc cactaagttg    180

agttttaaaa ctttatttca cattttaatc catttttttac atgaaaactt tccggaaaat    240

acggagtatg cacgcaagtc gaggaatgat aaatggtact tttcgaagtt ttagaactca    300

aaattactta ttaaatttaa agatgacatt ttgggtcatc acattgatga aaattttgac    360

attaatatct gagaactttc tttgaccttt ttcgattcta atccaatcaa ttcaacagtg    420

taaggtgaag cagtcaattt aaaggaaggc ctttaaattc taaaatattg tacttttcct    480

gcgcttctaa aagtgaacga caaagaaaaa atagttattc ttgaacttaa tattgtacaa    540

taggataaat tttaactatc tataaaaaga gaacaaaacc ttaatctctt caaaataata    600

ttataagaag taacataatt gtcaaatgaa atacacataa gaagcacata aatttaaatg    660

ccgtattaaa cttacagtat actatagcgg aagttggctt gataaaggaa cgctgaggag    720

agtagccgat ggtgaaacac taacatcaag tgcaaaagaa agaaaaactg aaaacagaag    780

atgaatgttt gaagtgggta aaagattact taaaagatag gtttggttaa caaatgattg    840

tgactgttac gaagcagtgt gaaccgttgg gacttttaat attcttcggc agaagaacat    900

tgctctttcc acgtatgtag tctttgtcta cttgtagttt tttttaattt aaattaaata    960

agttaattag agaaataata agaaggatat tttagtaatt caacttttaa cttttaggtt   1020

tcccacttat aatataatat agatatagtt ttttttaatt taaattaaat aagttaatta   1080

gagaaataat aagaaggata ttttagtaat tcaactttta acttttaggg tttccactta   1140

taatataata tagatataga tatagatata gatatagata aagatatata gatatagata   1200

gataatatag atggatgagt cattggcgat aaagtgagga tgtttcattt ttgttattaa   1260

aaacttacta ctccttaaat ataaaatatg attcctttta aaaaagaaat agaataaaaa   1320

taaagataaa acactaaaaa taaattaatt gtctagacaa aatctaccgt tcacctcaat   1380

taatacacat ccccgtccac atcatgaagt agctagcaca agcgtacaga tcagttgaaa   1440

gaagaaaagg gtccagtcct aaatatccaa atgttcatga aaggaggaca acttagtttt   1500

ttctactaga aagaatattt tgacgaattt cgttcacatt ggcatgcttt aattatatta   1560

agtagtcttt cttggaaaag aagtatttgc aatatcaaac caaatcttcc cattacgcaa   1620

gcaatgacat ctaagcaaat atatatcact ataaatagta ctactaatgt tcaatgact    1679
```

<210> SEQ ID NO 101
<211> LENGTH: 1510
<212> TYPE: DNA
<213> ORGANISM: Arabidopsis thaliana

<400> SEQUENCE: 101

```
ccaaggtaaa aaaaaggtat gaaagctcta tagtaagtaa aatataaatt ccccataagg     60

aaagggccaa gtccaccagg caagtaaaat gagcaagcac cactccacca tcacacaatt    120

tcactcatag ataacgataa gattcatgga attatcttcc acgtggcatt attccagcgg    180

ttcaagccga taagggtctc aacacctctc cttaggcctt tgtggccgtt accaagtaaa    240

attaacctca cacatatcca cactcaaaat ccaacggtgt agatcctagt ccacttgaat    300

ctcatgtatc ctagaccctc cgatcactcc aaagcttgtt ctcattgttg ttatcattat    360

atatagatga ccaaagcact agaccaaacc tcagtcacac aaagagtaaa gaagaacaat    420

ggcttcctct atgctctctt ccgctactat ggttgcctct ccggctcagg ccactatggt    480
```

-continued

```
cgctcctttc aacggactta agtcctccgc tgccttccca gccacccgca aggctaacaa    540
cgacattact tccatcacaa gcaacggcgg aagagttaac tgcatgcagg tcatttatat    600
ttcttctttc actttttat tattccatat gatttttttc ggttctttct tcgaatctac     660
ataaactaat atcattggaa aaatcgaaaa aataggtgtg gcctccgatt ggaaagaaga    720
agtttgagac tctctcttac cttcctgacc ttaccgattc cgaattggct aaggaagttg    780
actaccttat ccgcaacaag tggattcctt gtgttgaatt cgagttggag gtaattaaac    840
aaaatttaaa catctatata aactagctag atcttaggaa aatttggttt aatatattag    900
gatcttgatt tatataaaca tgttcaaaat gttatctgag tggtttgtaa catgtggttt    960
gtatagcacg gatttgtgta ccgtgagcac ggtaactcac ccggatacta tgatggacgg   1020
tactggacaa tgtggaagct tcccttgttc ggttgcaccg actccgctca agtgttgaag   1080
gaagtggaag agtgcaagaa ggagtacccc aatgccttca ttaggatcat cggattcgac   1140
aacacccgtc aagtccagtg catcagtttc attgcctaca agccaccaag cttcaccggt   1200
taatttccct ttgcttttgt gtaaacctca aaactttatc cccatcttt gattttatcc    1260
cttgtttttc tgctttttc ttctttcttg ggttttaatt tccggactta acgtttgttt    1320
tccggtttgc gagacatatt ctatcggatt ctcaactgtc tgatgaaata aatatgtaat   1380
gttctataag tctttcaatt tgatatgcat atcaacaaaa agaaaatagg acaatgcggc   1440
tacaaatatg aaatttacaa gtttaagaac catgagtcgc taaagaaatc attaagaaaa   1500
ttagtttcac                                                          1510
```

<210> SEQ ID NO 102
<211> LENGTH: 1268
<212> TYPE: DNA
<213> ORGANISM: Arabidopsis thaliana

<400> SEQUENCE: 102

```
ccaaggtaaa aaaaaggtat gaaagctcta tagtaagtaa aatataaatt ccccataagg     60
aaagggccaa gtccaccagg caagtaaaat gagcaagcac cactccacca tcacacaatt    120
tcactcatag ataacgataa gattcatgga attatcttcc acgtggcatt attccagcgg    180
ttcaagccga taagggtctc aacacctctc cttaggcctt tgtggccgtt accaagtaaa    240
attaacctca cacatatcca cactcaaaat ccaacggtgt agatcctagt ccacttgaat    300
ctcatgtatc ctagaccctc cgatcactcc aaagcttgtt ctcattgttg ttatcattat    360
atatagatga ccaaagcact agaccaaacc tcagtcacac aaagagtaaa gaagaacaat    420
ggcttcctct atgctctctt ccgctactat ggttgcctct ccggctcagg ccactatggt    480
cgctcctttc aacggactta agtcctccgc tgccttccca gccacccgca aggctaacaa    540
cgacattact tccatcacaa gcaacggcgg aagagttaac tgcatgcagg tgtggcctcc    600
gattggaaag aagaagtttg agactctctc ttaccttcct gaccttaccg attccgaatt    660
ggctaaggaa gttgactacc ttatccgcaa caagtggatt ccttgtgttg aattcgagtt    720
ggagcacgga tttgtgtacc gtgagcacgg taactcaccc ggatactatg atggacggta    780
ctggacaatg tggaagcttc ccttgttcgg ttgcaccgac tccgctcaag tgttgaagga    840
agtggaagag tgcaagaagg agtaccccaa tgccttcatt aggatcatcg gattcgacaa    900
cacccgtcaa gtccagtgca tcagtttcat tgcctacaag ccaccaagct tcaccggtta    960
atttcccttt gcttttgtgt aaacctcaaa actttatccc ccatctttga ttttatccct   1020
tgtttttctg ctttttcttt ctttcttggg ttttaatttc cggacttaac gtttgttttc   1080
```

cggtttgcga gacatattct atcggattct caactgtctg atgaaataaa tatgtaatgt 1140
tctataagtc tttcaatttg atatgcatat caacaaaaag aaaataggac aatgcggcta 1200
caaatatgaa atttacaagt ttaagaacca tgagtcgcta aagaaatcat taagaaaatt 1260
agtttcac 1268

<210> SEQ ID NO 103
<211> LENGTH: 966
<212> TYPE: DNA
<213> ORGANISM: Arabidopsis thaliana

<400> SEQUENCE: 103
atttatctct ctctctctct ctatttcttt tgcttccttt tggtatttgc tttgtatgtt 60
tgttttgaga tcaaaatggc ttcaagtgct tcaaagttca tcaagtgtgt gactgttggt 120
gatggtgctg ttggtaaaac ctgtatgctc atctgctaca ccagcaataa attccccact 180
gactacatac caacagtttt tgacaacttt agtgcaaatg ttgttgttga aggcaccact 240
gtcaatttgg ggctttggga cactgctggg caagaagact ataacagatt aaggccttta 300
agttacaggg gagcagatgt tttcgtcttg tctttctcat tagtcagccg agctagctac 360
gagaatgttt ttaaaaagtg gatccctgaa ctccaacact ttgctccagg agttcccctt 420
gtccttgttg gtaccaaatt agatcttcgt gaagataagc attatttggc tgatcatcct 480
ggactatccc ctgtaactac tgcacaggga gaggagttgc gtaagctaat tggtgcgacg 540
tattacattg agtgtagttc aaaaactcaa cagaatgtga aagcagtttt tgattctgcg 600
ataaaggaag tgatcaaacc tctggttaaa caaaaggaga agactaagaa gaagaagaag 660
caaaagtcga atcacggctg tttatcaaat gttctgtgtg ggaggatagt gactcggcat 720
tgatgacgat gacccaactc agtctgatga ttttaaactc cacttttgag attgtgtgat 780
aaacgagaga ctttatatta tatagattga atcatgtaag agattattag cctctaatca 840
atcaatagtt accttgaaga gagaaagagg gggaggtaga gagcttatta ttaattcaat 900
tgtgtttatt tgtttcaaac ctgttattgc aatatattag ccattttgat aaaaaaaaaa 960
aaaaaa 966

<210> SEQ ID NO 104
<211> LENGTH: 187
<212> TYPE: PRT
<213> ORGANISM: Arabidopsis thaliana

<400> SEQUENCE: 104

Met Met Asp Gly Val Glu Gly Gly Thr Ala Met Tyr Gly Gly Leu Glu
1 5 10 15

Thr Val Gln Tyr Val Arg Thr His His Gln His Leu Cys Arg Glu Asn
20 25 30

Gln Cys Thr Ser Ala Leu Val Lys His Ile Lys Ala Pro Leu His Leu
35 40 45

Val Trp Ser Leu Val Arg Arg Phe Asp Gln Pro Gln Lys Tyr Lys Pro
50 55 60

Phe Val Ser Arg Cys Thr Val Ile Gly Asp Pro Glu Ile Gly Ser Leu
65 70 75 80

Arg Glu Val Asn Val Lys Ser Gly Leu Pro Ala Thr Thr Ser Thr Glu
85 90 95

Arg Leu Glu Leu Leu Asp Asp Glu Glu His Ile Leu Gly Ile Lys Ile
100 105 110

-continued

```
Ile Gly Gly Asp His Arg Leu Lys Asn Tyr Ser Ser Ile Leu Thr Val
        115                 120                 125

His Pro Glu Ile Ile Glu Gly Arg Ala Gly Thr Met Val Ile Glu Ser
    130                 135                 140

Phe Val Val Asp Val Pro Gln Gly Asn Thr Lys Asp Glu Thr Cys Tyr
145                 150                 155                 160

Phe Val Glu Ala Leu Ile Arg Cys Asn Leu Lys Ser Leu Ala Asp Val
                165                 170                 175

Ser Glu Arg Leu Ala Ser Gln Asp Ile Thr Gln
            180                 185


<210> SEQ ID NO 105
<211> LENGTH: 788
<212> TYPE: DNA
<213> ORGANISM: Arabidopsis thaliana

<400> SEQUENCE: 105

gaagttcact tgttgtgaat gactatgatt tgatcaaatt agttaatttt gtcgaatcat      60

ttttcttttt gatttgatta agcttttaac ttgcacgaat ggttctcttg tgaataaaca     120

gaatctttga attcaaacta tttgattagt gaaaagacaa aagaagattc cttgttttta     180

tgtgattagt gattttgatg catgaaaggt acctacgtac tacaagaaaa ataaacatgt     240

acgtaactac gtatcagcat gtaaaagtat ttttttccaa ataatttata ctcatgatag     300

attttttttt tttgaaatgt caattaaaaa tgctttctta aatattaatt ttaattaatt     360

aaataaggaa atatatttat gcaaaacatc atcaacacat atccaacttc gaaaatctct     420

atagtacaca agtagagaaa ataaatttta ctagatacaa acttcctaat catcaattat     480

aaatgtttac aaaactaatt aaacccacca ctaaaattaa ctaaaaatcc gagcaaagtg     540

agtgaacaag acttgatttc aggttgatgt aggactaaaa tggctacgta tcaaacatca     600

acgatcattt agttatgtat gaatgaatgt agtcattact tgtaaaacaa aaatgctttg     660

atttggatca atcacttcat gtgaacatta gcaattacat caaccttatt ttcactataa     720

aaccccatct cagtaccctt ctgaagtaat caaattaaga gcaaaagtca tttaactttc     780

ctaaaaca                                                              788


<210> SEQ ID NO 106
<211> LENGTH: 6
<212> TYPE: DNA
<213> ORGANISM: Artificial Sequence
<220> FEATURE:
<223> OTHER INFORMATION: Synthetic construct

<400> SEQUENCE: 106

cacgtg                                                                  6
```

PYL9 AND USES THEREOF

CROSS-REFERENCE TO RELATED APPLICATIONS

This application is filed under the provisions of 35 U.S.C. § 371 and claims the priority of International Patent Application No. PCT/US2016/062468 filed on 17 Nov. 2016 entitled "PYL9 AND USES THEREOF", which in turn claims priority to U.S. Provisional Patent Application No. 62/257,027 filed on Nov. 18, 2015, the content of which is hereby incorporated by reference herein for all purposes.

GOVERNMENT INTEREST

This invention was made with government support under Grant Numbers R01GM059138 awarded by the U.S. National Institute of Health. The government has certain rights in the invention.

SEQUENCE TEXT FILE

The sequences described in the sequence text file PRF 67210-02-036511.27 PCT and filed herewith are incorporated by reference herein.

BACKGROUND OF THE INVENTION

Field of the Invention

The present invention relates generally to drought-resistant transgenic plants, and more specifically, to transgenic lines showing dramatically increased drought resistance and drought-induced leaf senescence by overexpressing the pyrabactin resistance 1-like (PYL) family of abscisic acid (ABA) receptors.

Background of Related Technology

Drought is perhaps the single most important factor that devastates crop production on the planet every year. Global warming aggravates this kind of natural disaster. Thus, breeding for drought-tolerant crop cultivars has never been as urgent as today. In general there are two ways to enhance drought tolerance of plants, that being, increasing water-absorbing ability or improving water-conservation power of plants.

Plants have evolved sophisticated mechanisms to cope with and adapt to the changing environment. For example, stomata open/closure of plants, which is essential for water transpiration and gas exchange necessary for photosynthesis, is tightly regulated via multiple pathways to help plants constantly adjust to regular and irregular environmental changes such as light, water, $CO_2$ and pathogens.

Cell and organ senescence causes programmed cell death to regulate the growth and development of organisms. In plants, leaf senescence increases the transfer of nutrients to developing and storage tissues. Recently, studies on transgenic tobacco showed that delayed leaf senescence increases plant resistance to drought stress (1). However, the senescence and abscission of older leaves and subsequent transfer of nutrients are known to increase plant survival under abiotic stresses, including drought, low or high temperatures, and darkness (2, 3). Senescence mainly develops in an age-dependent manner and is also triggered by environmental stresses and phytohormones, such as abscisic acid (ABA), ethylene, salicylic acid, and jasmonic acid, but delayed by cytokinin (4).

Senescence-associated genes (SAGs) are induced by leaf senescence. The expression of SAGs is tightly controlled by several senescence-promoting, plant-specific NAC (NAM, ATAF1, and CUC2) transcription factors, such as Oresara 1 (ORE1) (5), Oresara 1 sister 1 (ORS1) (6), and AtNAP (7). Environmental stimuli and phytohormones may regulate leaf senescence through NACs. Phytochrome-interacting factor 4 (PIF4) and PIF5 transcription factors promote dark-induced senescence by activating ORE1 expression (8). The expression of ORE1, AtNAP, and OsNAP (ortholog of AtNAP) is up-regulated by ABA by an unknown molecular mechanism (7, 9).

ABA is an important hormone that regulates plant growth and development and responses to abiotic stresses, such as drought and high salinity (10). Although it is well-known that ABA promotes leaf senescence, the underlying molecular mechanism is obscure. Previous studies suggested that ABA promotes senescence by causing ethylene biosynthesis (11). ABA induces expression of several SAGs and yellowing of the leaves, which are typical phenomena associated with leaf senescence (9, 12). ABA is sensed by the pyrabactin resistance 1 and pyrabactin resistance 1-like (PYL)/regulatory component of abscisic acid receptor proteins (13, 14). The ABA-bound PYLs prevent clade A protein phosphatase type 2Cs (PP2Cs) from inhibiting the sucrose non-fermenting 1-related protein kinase 2s (SnRK2s). ABA-activated SnRK2s phosphorylate transcription factors, such as ABA-responsive element-binding factors (ABFs), and these phosphorylated ABFs regulate the expression of ABA-responsive genes (15). In *Arabidopsis,* 14 PYLs function diversely and redundantly in ABA and drought-stress signaling (16-19).

Notably, the physiological roles of ABA-induced senescence under stress conditions and the underlying molecular mechanism are unclear. Thus, it would be advantageous to understand how each PYL affects drought resistance and whether the overexpression of certain PYLs with subsequent interaction with ABA affects both short-term responses, such as stomatal closure, and long-term responses, such as senescence.

SUMMARY OF THE INVENTION

The present invention identifies transgenic plants that are extremely resistant to drought from a large-scale screening of transgenic plants overexpressing the pyrabactin resistance 1-like (PYL) family of abscisic acid (ABA) receptors. How these plants resist drought by examining both short-term responses, such as stomatal closure, and long-term responses, such as senescence was explored. It was found herein that ABA induces senescence by activating ABA-responsive element-binding factors and related to ABA-Insensitive 3/VP1 transcription factors through core ABA signaling. Additionally, the results provided herein show that PYL9 promotes drought resistance by not only limiting transpirational water loss, but also, causing summer dormancy-like responses, such as senescence, in old leaves and growth inhibition in young tissues under severe drought conditions.

In one aspect, the present invention relates to plants and methods of producing modified plants that exhibit enhanced drought resistance and senescence relative to non-modified plants. Specifically the present invention relates to increasing amounts of PYL9 in plants to interact with abscisic acid (ABA) thereby activating enhanced drought resistance and senescence relative to non-modified plants.

In another aspect, the present invention provides for a transgenic plant having increased drought tolerance and leaf senescence compared to a control plant, wherein the transgenic plant is transformed with a recombinant DNA construct comprising a polynucleotide sequence encoding a PYL9 polypeptide or a polypeptide having at least 95% identity to the PLY9 polypeptide and having the same functional activity and wherein the polynucleotide sequence encoding a PYL9 polypeptide is operatively linked to a polynucleotide sequence encoding a promoter. Preferably, the polynucleotide sequence encoding the PYL9 polypeptide is SEQ ID NO. 89 and the polynucleotide sequence encoding the promoter is SEQ ID NO. 99.

In a further aspect, the present invention provides a DNA construct that provides for increased expression of PYL9 in a modified plant and thus enhances drought resistance and senescence relative to non-modified plant, wherein the DNA construct comprises a nucleotide sequence for expressing a RD29A promoter which is operatively linked to a nucleotide sequence expressing a PYL9 protein.

In yet another aspect, the present invention relates to a method of producing a transgenic plant having an increased tolerance to an environmental stress, such as drought stress, said method comprising the steps of:

(a) transforming plant cells with an expression cassette comprising a polynucleotide sequence which comprises a nucleotide sequence encoding an PYL9 protein having an amino acid sequence of SEQ ID NO. 104 or at least having 95% identity to the amino acid sequence set forth in SEQ ID NO: 104 with the same functional activity, and wherein the nucleotide sequence encoding the PYL9 protein is operably linked to a RD29A promoter (SEQ ID NO. 99) to produce pRD29A::PYL9 transgenic plants;
(b) regenerating transgenic plants from said transformed plant cells; and
(c) selecting a transformed plant from said transgenic plants which exhibits increase in tolerance to an environmental stress as compared to an untransformed plant of the same species, and wherein said increase in environmental stress tolerance is due to the increased expression of the PYL-9 protein in the selected transformed plant.

In a further aspect, the present invention provides for obtaining transformed seeds from the selected transformed plant generated by the method above, and wherein the transformed seeds comprise the expression cassette and exhibit increase in tolerance to the environmental stress as compared to an untransformed seeds of the same species.

In another aspect, the present invention provides for a method of producing a transgenic plant with increased drought tolerance and leaf senescence as compared to a control or wild type plant. The method comprises the steps of;

(i) providing a recombinant DNA construct comprising a polynucleotide sequence encoding a PLY9 polypeptide having an amino acid sequence of SEQ ID NO. 104 or at least 95% identity to the amino acid sequence set forth in SEQ ID NO: 104 with the same functional activity, and wherein the polynucleotide sequence encoding a PLY9 polypeptide is operably linked to a RD29A promoter (SEQ ID NO. 99); and
(ii) introducing the recombinant DNA construct into a plant to produce a pRD29A::PYL9 transgenic plant, wherein the pRD29A::PYL9 transgenic plant exhibits increased drought tolerance and leaf senescence.

The transgenic plant may include a monocotyledonous plant selected from the group consisting of wheat, maize, rye, rice, corn, oat, barley, turfgrass, sorghum, millet and sugarcane or a dicotyledonous plant selected from the group consisting of tobacco, tomato, potato, soybean, cotton, canola, sunflower and alfalfa.

In another aspect, the present invention provides for a seed of a transgenic plant, wherein the seed comprises the expression cassette pRD29A::PYL9.

In yet another aspect, the present invention provides for obtaining a progeny plant derived from the transgenic plant, wherein said progeny plant comprises stably-integrated in its genome the recombinant DNA construct comprising SEQ ID NO. 89 and SEQ ID NO. 99 and exhibits increased drought tolerance when compared to a control plant not comprising the recombinant DNA construct.

In a still further aspect, the present invention provides for an isolated nucleic acid comprising polynucleotide sequences of SEQ ID NO. 99 and SEQ ID NO. 89. The isolated nucleic acid is included in a vector, plasmid or expression cassette.

In another aspect, the present invention provides for a kit comprising an expression cassette pRD29A::PYL9 comprising SEQ ID NO. 89 and SEQ ID NO. 99 to produce a transgenic plant exhibiting increased drought tolerance and leaf senescence relative to a non-transgenic plant.

Other features and advantages of the invention will be apparent from the following detailed description, drawings and claims.

BRIEF DESCRIPTION OF THE FIGURES

(FIG. 1B) shows images of representative seedlings. (FIG. 1C) shows soil water content during the drought-stress period. Error bars indicate SEM ($n \geq 4$).

(FIG. 2A) pRD29A::PYL9 confers drought resistance in *Arabidopsis*. Water was withheld from 3-wk-old *Arabidopsis* plants for 20 d under short-day conditions before watering was resumed. Representative images show plants 7 d before rewatering, on the day of rewatering, and 2 d after watering was resumed. (FIG. 2B) shows cumulative transpirational water loss from rosettes of the WT (Col-0) and pRD29A::PYL9 transgenic *Arabidopsis* at the indicated times after detachment. Error bars indicate SD (n=3). (FIG. 2C) shows electrolyte leakage of the WT (Col-0) and pRD29A::PYL9 transgenic *Arabidopsis* at the indicated days after water was withheld. Error bars indicate SD (n=3). (FIG. 2D) shows pRD29A::PYL9 confers drought resistance in rice. Water was withheld from 4-wk-old rice plants for 14 d. Plants were photographed 14 d after watering was resumed. *P<0.05 (Student's t test).

(FIGS. 3A and 3B) shows that pRD29A::PYL9 accelerates ABA-induced leaf senescence in *Arabidopsis*. (FIG. 3A) shows plants were photographed 2 d after they were sprayed with ABA. (FIG. 3B) shows chlorophyll content in mature leaves of WT (Col-0) and pRD29A::PYL9 lines. Error bars indicate SEM (n=3). (FIG. 3C) shows expression of SAG12 in pRD29A::PYL9 lines. The expression level of SAG12 in Col-0 without ABA treatment was set at one. Error bars indicate SEM (n=3). (FIGS. 3D and 3E) show leaf growth and chlorophyll content of the WT (Col-0), the pyl9 mutant, and the pyl8-1pyl9 double mutant were documented at 17 d after the seedling were transferred to Murashige and Skoog (MS) medium with or without 10 μM ABA and grown under low light (30-45 $\mu mol\ m^{-2}\ s^{-1}$). Error bars indicate SEM (n=3). (FIG. 3F) shows that pRD29A::PYL9 accelerates ABA-induced leaf senescence in rice. The third-oldest leaves of WT (ZH11) and pRD29A::PYL9 rice lines were photographed. (FIG. 3G) Expression of Osh36 and Osl85 in pRD29A::PYL9 rice lines. The expression level of SAGs in ZH11 without ABA treatment was set at one. *P<0.05 (Student's t test); P<0.01 (Student's t test); *P<0.001 (Student's t test).

(FIGS. 4A and 4B) show leaf growth of the WT [*Landsberg erecta* (Ler)]; the abi1-1 mutant; the WT (Col-0); snrk2.2, snrk2.3, and snrk2.6 single mutants; snrk2.2/3 double mutant; and snrk2.2/3/6 triple mutant at 13 d after seedlings were transferred to Murashige and Skoog (MS) medium with or without 10 μM ABA. (FIG. 4C) shows SAG12-LUC expression in snrk2.2/3/6 triple-mutant protoplasts cotransformed with SnRK2.6, ABI1, and PYL9. Error bars indicate SEM (n≥3). (FIG. 4D) shows SAG12-LUC expression in Col-0 protoplasts cotransformed with ABI5, EEL, AREB3, and ABF2. Error bars indicate SEM (n≥3). (FIG. 4E) shows SAG12-LUC expression in snrk2.2/3/6 triple-mutant protoplasts cotransformed with SnRK2.6, ABF2, and $ABF2^{S26DS86DS94DT135D}$. Error bars indicate SEM (n=4). (FIG. 4F) shows expression of ORE1 and AtNAP in pRD29A::PYL9 lines. The expression level of ORE1 and AtNAP in Col-0 without ABA treatment was set at one. Error bars indicate SEM (n=3). (FIG. 4G) shows ORE1L-LUC expression in Col-0 protoplasts cotransformed with RAV1, SnRK2.6, ABI1, and PYL9. Error bars indicate SEM (n=3). *P<0.05 (Student's t test); P<0.01 (Student's t test); *P<0.001 (Student's t test).

(FIGS. 5A and 5B) show pRD29A::PYL9 accelerates ABA-induced drying in senescing leaves under well-watered conditions. Four-week-old *Arabidopsis* plants growing in soil were sprayed with 20 μM ABA plus 0.2% Tween-20. (FIG. 5A) show plants that were photographed 4 d after they were sprayed with ABA. (FIG. 5B) shows that pRD29A::PYL9 transgenic plants exhibit improved osmoregulation in sink tissues. Samples were collected 2 d after ABA was sprayed. Error bars indicate SEM (n=6). (FIG. 5C) shows expression of SWEET15 in pRD29A::PYL9 lines. The expression level of SWEET15 in Col-0 without ABA treatment was set at one. Error bars indicate SEM (n=3). *P<0.05 (Student's t test); P<0.01 (Student's t test); *P<0.001 (Student's t test).

FIG. 6A shows the pRD29A::PYL transgenic lines, FIG. 6B shows the pGC::PYL transgenic lines, and FIG. 6C shows the 35S::PYL transgenic lines.

(FIG. 7A) shows that PYL5, PYL7, and PYL9 can antagonize the ability of HAI1 to inhibit the induction of RD29B-LUC expression in the presence of 0.5 μM ABA in Col-0 protoplasts. Error bars indicate SEM (n=3). *P<0.05 (Student's t test). (FIG. 7B) shows that PYL9 can reduce the ability of all tested PP2Cs to inhibit the ABA-dependent induction of RD29B-LUC expression in protoplasts. Error bars indicate SEM (n=3).

(FIG. 8A) shows northern blot verification using DIG-labeled PYL probes. Samples were collected under drought-stress conditions. DIG, digoxigenin. (FIG. 8B) shows PCR verification using promoter forward primer plus gene-specific reverse primer. (FIGS. 8C to 8F) shows physiological parameters of pRD29A::PYL9 lines under drought-stress conditions. Three-week-old plants were subjected to drought stress (water was withheld for 5 d) before parameters were measured. pRD29A::PYL9 values are the means of three independent transgenic lines. Error bars indicate SD (n=3). (FIG. 8G) shows the $H_2O_2$ content and the antioxidant enzyme activities of the WT (Col-0) and pRD29A::PYL9 transgenic *Arabidopsis* under drought-stress conditions. For $H_2O_2$ content measurement, water was withheld from 2-wk-old plants for 14 d, and the leaves were collected. For antioxidant enzyme activities, water was withheld from 3-wk-old plants for 10 d. Values for enzyme activities were normalized to those for the WT plants grown under well-watered conditions, which were set at one. Error bars indicate SD (n=3). (FIG. 8H) shows relative fresh and dry weights of the WT (Col-0) and pRD29A::PYL9 transgenic *Arabidopsis*. Water was withheld from 2-wk-old plants for 20 d, and the aboveground materials were collected and weighed before and after drying. The values were normalized to those for the WT plants grown under well-watered conditions, which were set at one. Error bars indicate SD (n=3). (FIG. 8I) shows the expression of the *Arabidopsis* PYL9 transgene in rice. Error bars indicate SEM (n=3). (FIG. 8J) shows survival rate, total biomass, and electrolyte leakage of the WT (ZH11) and pRD29A::PYL9 transgenic rice. Plants were collected 14 d after water was withheld. Error bars indicate SD (n=3). *P<0.05 (Student's t test).

(FIG. 9A) shows that pRD29A::PYL9 accelerates drought-induced leaf senescence in *Arabidopsis*. Water was withheld from 3-wk-old *Arabidopsis* plants growing in Jiffy 7 Peat Soil for 14 d. (FIG. 9B) shows expression of PYL9 in pRD29A::PYL9 lines. Quantitative RT-PCR was conducted with leaves of 4-wk-old *Arabidopsis* plants that were grown in soil and sprayed with 20 μM ABA for 12 and 24 h. The expression level of PYL9 in Col-0 without ABA treatment was set at one. Error bars indicate SEM (n=3). (FIG. 9C) shows expression of SAG13 in pRD29A::PYL9 lines. The expression level of SAG13 in Col-0 without ABA treatment was set at one. Error bars indicate SEM (n=3). (FIG. 9D) shows the leaves of WT (Col-0), pyl9 mutant, and pyl8-

1pyl9 double mutant at 17 d after transfer to Murashige and Skoog (MS) medium with or without 10 μM ABA under normal light (80-100 μmol m−2 s−1). (FIG. 9E) shows the chlorophyll content in third oldest leaves of WT (ZH11) and pRD29A::PYL9 rice lines that were growing in soil after they were sprayed with 100 μM ABA. Error bars indicate SEM (n=3). *P<0.05 (Student's t test); P<0.01 (Student's t test); *P<0.001 (Student's t test).

(FIG. 11A) shows SAG12-LUC expression in Col-0 WT protoplasts treated with the ethylene biosynthesis inhibitor AVG. Error bars indicate SEM (n=3). (FIG. 11B) shows leaf growth of WT (Col-0) and ethylene-insensitive mutants ein2-1 and ein3-1 13 d after seedlings were transferred to a medium with or without 10 μM ABA. (FIG. 11C) shows SAG12-LUC expression in ein2-1 mutant protoplasts cotransformed with ABI1 and PYL9. Error bars indicate SEM (n=3).

(FIG. 12A) shows the detection of the PYL9-HA-YFP protein in a sample purified from 10-d-old seedlings of ProPYL9:PYL9-HA-YFP-expressing lines. PYL9-HA-YFP protein was detected with anti-GFP mouse antibodies (Roche). (FIG. 12B) shows the procedure for purification of PYL9-associated proteins using tandem affinity purification (TAP) in extracts of 10-d-old seedlings of the transgenic plants treated with ABA or osmotic stress. (FIG. 12C) shows identification of PYL9-associated proteins in TAP-MS analyses using ProPYL9:PYL9-HA-YFP transgenic plants not treated or treated with ABA or mannitol. Detailed data of the peptides identified by MS analyses are provided in Table 1. (FIG. 12D) shows PYL9-PP2C interactions in the Y2H assay. Interaction was determined by yeast growth on media lacking His with and without ABA. Dilutions (10-1, 10-2, and 10-3) of saturated cultures were spotted onto the plates, which were photographed after 5 d. The activating domain (AD)-MYB44/binding domain (BD)-PYL8 and AD/BD-PYL9 combinations were included as positive and negative controls, respectively, for the Y2H interaction assay. (FIG. 12E) shows promoter region (SEQ ID NO. 105) for SAG12-LUC reporter fusion. The ORE1 binding site is underlined. (FIG. 12F) shows SAG12-LUC expression in Col-0 WT protoplasts cotransformed with ABI1 and PYL9 (n=4 experiments). Values are means±SEMs. (FIG. 12G) shows SAG12-LUC expression in Col-0 WT protoplasts cotransformed with PP2Cs (n=3 experiments). Values are means±SEMs. (FIGS. 12H and 12I) shows the chlorophyll content of the WT (Ler), the abi1-1 mutant, WT (Col-0), and snrk2.2/3/6 triple mutant 13 d after seedlings were transferred to a medium with or without 1 μM ABA. Error bars indicate SEM (n=6). *P<0.05 (Student's t test); P<0.01 (Student's t test); *P<0.001 (Student's t test). Ler, *Landsberg erecta*; MS, Murashige and Skoog medium; NOS, NOS terminator; WB, Western blotting; Y2H, yeast two hybrid.

(FIG. 13A) shows phylogenetic tree of ABFs in *Arabidopsis*. (FIG. 13B) shows SAG12-LUC expression in Col-0 protoplasts cotransformed with ORE1, ORS1, and AtNAP. Error bars indicate SEM (n≥3). *P<0.05 (Student's t test); P<0.01 (Student's t test); *P<0.001 (Student's t test). (FIG. 13C) shows a diagram of promoters of ORE1, ORS1, and AtNAP. (FIG. 13D) shows expression of ORE1, ORS1, and AtNAP with ABA treatment according to data from the *Arabidopsis* eFP browser (bar.utoronto.ca/efp/cgi-bin/efpWeb.cgi). (FIG. 13E) shows a scheme for the ORE1L-LUC reporter. The 3,984-bp fragment of the ORE1 promoter was fused to the LUC reporter gene (ORE1L-LUC) to use as a senescence-responsive reporter. The 3,984-bp ORE1 promoter contains the RAV1(1) and RAV1(2) motifs. bZIP, the basic region-leucine zipper; eFP, electronic fluorescent pictograph.

FIGS. 14A, 14B, 14C, 14D, 14E, 14F, 14G and 14H show that core ABA signaling promotes ABA-induced growth inhibition and the expression of cuticular wax biosynthesis genes. (FIG. 14A) shows seed germination and seedling growth of WT (Col-0), snrk2.2/3/6, pyl8-1pyl9, and pRD29A::PYL9 lines in Murashige and Skoog medium and Murashige and Skoog medium plus 1 μM ABA at 8 d. (FIGS. 14B and 14C) show rosette growth of WT (Col-0) and pRD29A::PYL9 lines at 13 d after transfer to a medium with or without 1 μM ABA. (FIG. 14B) shows images of representative seedlings. (FIG. 14C) shows rosette width. Error bars indicate SEM (n=6). (FIG. 14D) Rosette width of WT (Col-0), pyl9, and pyl8-1pyl9 double mutants was documented at 17 d after transfer to a medium with or without 10 μM ABA under low light (30-45 μmol m−2 s−1). Error bars indicate SEM (n=12). (FIG. 14E) shows rosette width of WT (Col-0), single mutants (snrk2.2, snrk2.3, and snrk2.6), snrk2.2/3 double mutant, and snrk2.2/3/6 triple mutant 13 d after transfer to a medium with or without 10 μM ABA. Error bars indicate SEM (n=8). *P<0.05 (Student's t test); *P<0.001 (Student's t test). (FIG. 14F) shows seedling growth of WT (ZH11) and pRD29A::PYL9 rice lines 20 d after transfer to a medium with or without 5 μM ABA. (FIG. 14G) shows expression of wax biosynthetic genes in pRD29A::PYL9 lines. Quantitative RT-PCR was performed at the indicated time after transfer of 7-d-old seedlings to a medium with or without 1 μM ABA. The expression level of genes in Col-0 without ABA treatment was set at one. Error bars indicate SEM (n=3).

FIG. 16 shows the nucleotide sequence for SEQ ID NO. 89 (PLY9) and amino acid sequence for SEQ ID NO. 104 (PLY9).

FIG. 17 shows the nucleotide sequence for SEQ ID NO. 99 for RD29A promoter.

DETAILED DESCRIPTION OF THE INVENTION

Figure 1:
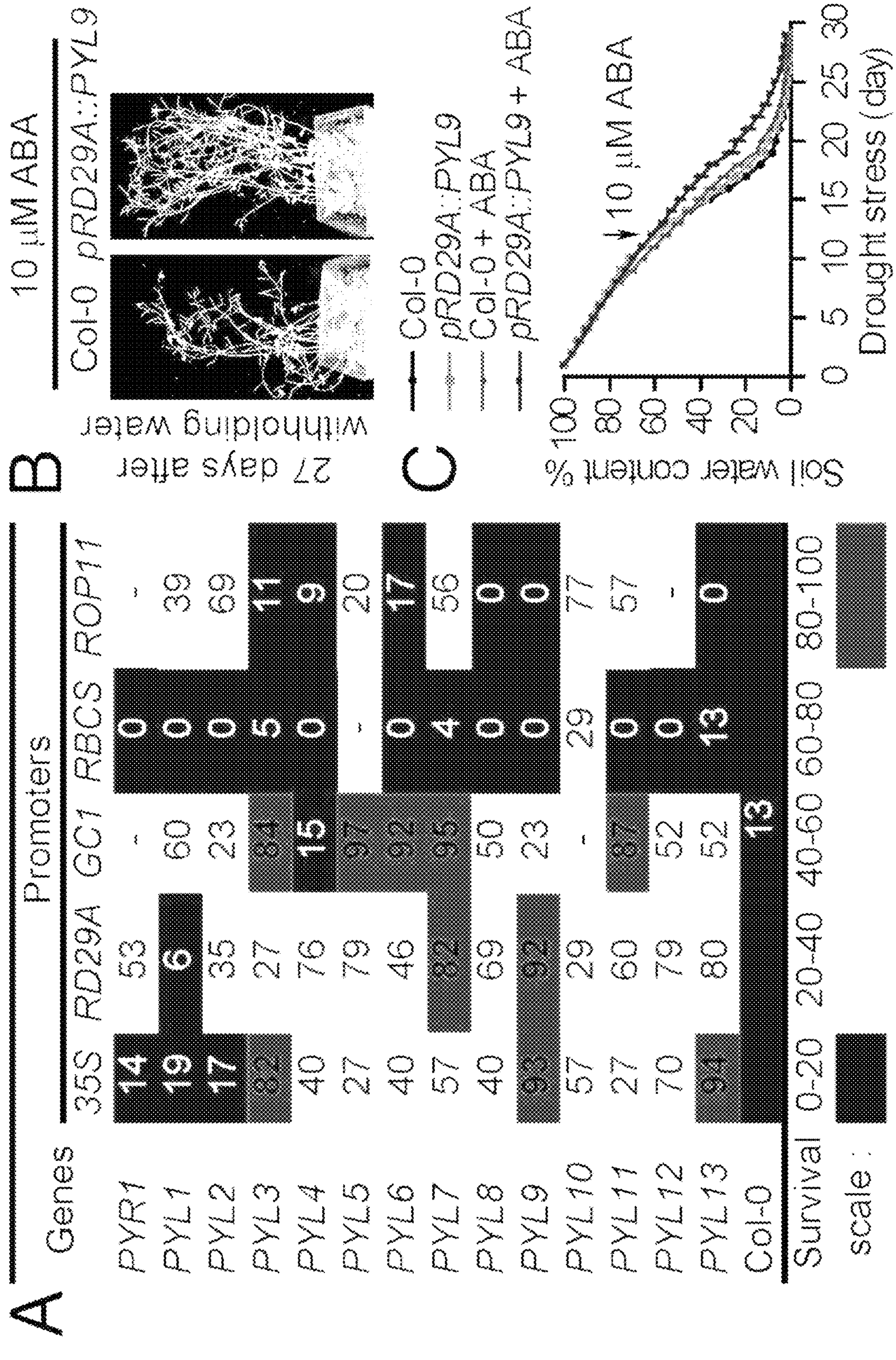
FIGS. 1A, 1B and 1C show the screening PYL transgenic lines for resistance to drought stress in (FIG. 1A) Drought-resistance screening of PYL transgenic *Arabidopsis*. Fourteen *Arabidopsis* PYLs and five promoters were used to generate 65 transgenic plants with different promoter-PYL combinations. Two-week-old plants were subjected to drought stress by withholding water for 20 d. Survival rates were calculated at 2 d after rehydration. "-" indicates that no transgenic plants were obtained. pRD29A::PYL9 transgenic plants exhibit improved drought-stress resistance with ABA treatment. Plants were subjected to drought stress after flowering. After water was withheld for 12 d, plants were treated once with 10 μM ABA.

The present invention will now be described more fully hereinafter with reference to the accompanying drawings, in which some, but not all, embodiments are shown. Indeed, the invention may be embodied in many different forms and should not be construed as limited to the embodiments set forth herein; rather, these embodiments are provided so that this disclosure will satisfy applicable legal requirements. Additionally, while embodiments are disclosed as "comprising" elements, it should be understood that the embodiments may also "consist of" elements or "consist essentially of" elements. Where possible, any terms expressed in the singular form herein are meant to also include the plural form and vice versa unless explicitly stated otherwise. Also, as used herein, the term "a" and/or "an" shall mean "one or more," even though the phrase "one or more" is also used herein. Like numbers refer to like elements throughout.

Drought stress is an important environmental factor limiting plant productivity. In the present invention, drought-resistant transgenic plants were screened from 65 promoter-pyrabactin resistance 1-like (PYL) abscisic acid (ABA) receptor gene combinations and it is shown herein that pRD29A::PYL9 transgenic lines showed dramatically increased drought resistance and drought-induced leaf senescence in both *Arabidopsis* and rice. Previous studies suggested that ABA promotes senescence by causing ethylene production. However, in the present invention it was found that ABA promotes leaf senescence in an ethylene-independent manner by activating sucrose nonfermenting 1-related protein kinase 2s (SnRK2s), which subsequently phosphorylates ABA-responsive element-binding factors (ABFs) and Related to ABA-Insensitive 3/VP1 (RAV1) transcription factors. The phosphorylated ABFs and RAV1 up-regulate the expression of senescence-associated genes, partly by up-regulating the expression of Oresara 1. The pyl9 and ABA-insensitive 1-1 single mutants, pyl8-1pyl9 double mutant, and snrk2.2/3/6 triple mutant showed reduced ABA-induced leaf senescence relative to the WT, whereas pRD29A::PYL9 transgenic plants showed enhanced ABA-induced leaf senescence. It was found that leaf senescence may benefit drought resistance by helping to generate an osmotic potential gradient, which is increased in pRD29A::PYL9 transgenic plants and causes water to preferentially flow to developing tissues. The results shown herein uncover the molecular mechanism of ABA-induced leaf senescence and suggest an important role of PYL9 and leaf senescence in promoting resistance to extreme drought stress.

Definitions

The term "promoter," as used herein, refers to a polynucleotide sequence capable of driving transcription of a coding sequence in a cell generally located upstream of the initiation site of a gene, to which RNA polymerase may bind and initiate correct transcription. Thus, promoters used in the polynucleotide constructs of the invention include cis-acting transcriptional control elements and regulatory sequences that are involved in regulating or modulating the timing and/or rate of transcription of a gene. A "plant promoter" is a promoter capable of initiating transcription in plant cells.

The term "plant," as used herein, refers to whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention generally as broad as the class of higher and lower plants amenable to transformation techniques, including angiosperms (monocotyledonous plants and dicotyledonous plants), gymnosperms, ferns, horsetails, psilophytes, lycophytes, and bryophytes.

The term "transgenic," as used herein, describes a non-naturally occurring plant that contains a genome modified by man, wherein the plant includes in its genome an exogenous nucleic acid molecule, which can be derived from the same or a different plant species. The exogenous nucleic acid molecule can be a gene regulatory element such as a promoter, enhancer, or other regulatory element, or can contain a coding sequence, which can be linked to a heterologous gene regulatory element.

The term "expression cassette," as used herein, refers to a nucleic acid construct that, when introduced into a host cell, results in transcription and/or translation of an RNA or polypeptide, respectively. In the case of expression of transgenes one of skill will recognize that the inserted polynucleotide sequence need not be identical, but may be only "substantially identical" to a sequence of the gene from which it was derived.

The terms "increased" or "enhanced" PYL expression or activity, as used herein, refers to an augmented change in the protein's expression or activity. Examples of such increased activity or expression include, e.g., where PYL expression is increased above control levels. Preferably, PYL expression or activity is increased above the level of that in wild-type, non-transgenic control plants.

The term "drought-resistance" or "drought-tolerance," as used herein, refers to the ability of a plant to recover from periods of drought stress (i.e., little or no water for a period of days). Typically, the drought stress will be at least 5 days and can be as long as, for example, 18 to 20 days or more (e.g., at least 6, 7, 8, 9, 10, 11, 12, 13, 14, 15, 16, 17, 18, 19, 20 days), depending on, for example, the plant species.

The "gene," as used herein, means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

The term "gene expression," as used refers to the process by which a polypeptide is produced based on the nucleic acid sequence of a gene. The process includes both transcription and translation.

The term "over-expression," as used herein refers to increased expression of a polypeptide sequence relative to its expression in a wild-type (or other reference [e.g., non-transgenic]) plant and may relate to a naturally-occurring or non-naturally occurring sequence.

The term "introduced," as used herein, means "transfection," "transformation" or "transduction" and includes reference to the incorporation of a nucleic acid sequence into a plant cell where the nucleic acid sequence may be incorporated into the genome of the cell (for example, chromosome, plasmid, plastid, or mitochondrial DNA), converted into an autonomous replicon, or transiently expressed (for example, transfected mRNA).

The term "plant cell," as used herein refers to any cell derived from a plant, including cells from undifferentiated tissue (e.g., callus) as well as plant seeds, pollen, progagules and embryos.

The term "modified" regarding a plant trait as used herein, refers to a change in the phenotype of a transgenic plant relative to the similar non-transgenic plant. A change in the phenotype refers to an observable or measurable phenotype demonstrated by a T1 and/or subsequent generation plant, which is not displayed by the corresponding non-transgenic (i.e., a genotypically similar plant that has been raised or assayed under similar conditions). An "improvement" is a feature that may enhance the utility of a plant species or variety by providing the plant with a unique and/or novel quality.

The term "polynucleotide," as used herein, means a sequence of two or more deoxyribonucleotides (in DNA) or ribonucleotides (in RNA). The term "polypeptide," as used herein, means a sequence of two or more amino acids.

The term "DNA construct," as used herein, means a nucleic acid molecule that is isolated from a naturally occurring gene or which has been modified to contain segments of nucleic acid which are combined and juxtaposed in a manner which would not normally otherwise exist in nature.

The term "transgenic plant" as used herein refers to a plant that contains genetic material not found or arranged the same in a wild-type plant of the same species, cultivar, or variety. The genetic material may include a transgene, an insertional mutagenesis event (such as by transposon or T-DNA insertional mutagenesis), an activation tagging sequence, a mutated sequence, a homologous recombination event, or a sequence modified by chimeraplasty. Typically, the foreign genetic material has been introduced into the plant by human manipulation, but any method can be used as one of skill in the art recognizes. A transgenic plant may contain an expression vector or cassette. The expression cassette typically comprises a polypeptide-encoding sequence operably linked to appropriate inducible or constitutive regulatory sequences that allow for the expression of a polypeptide. The expression cassette can be introduced into a plant by transformation or by breeding after transformation of a parent plant.

The term "operably linked," as used herein, means two DNA sequence linked and the linkage allows the two sequences to carry out their normal functions relative to each other. For instance, a promoter region would be operably linked to a coding sequence if the promoter were capable of effecting transcription of that coding sequence and said coding sequence encoded a product intended to be expressed in response to the activity of the promoter.

The term "(%) percent identity," as used herein relates to the extent to which the sequences of DNA or protein segments are invariant throughout a window of alignment of sequences, for example nucleotide sequences or amino acid sequences. An "identity fraction" for a sequence aligned with a reference sequence is the number of identical components which are shared by the sequences, divided by the length of the alignment not including gaps introduced by the alignment algorithm. Percent identity is calculated over the aligned length preferably using a local alignment algorithm, such as BLASTp. As used herein, sequences are "aligned" when the alignment produced by BLASTp has a minimal e-value.

The term "functional activity," as used herein, related to the proteins for use according to the present invention have the ability to provide for drought tolerance which can result in an increased yield. Transfer of the functional activity to plant or bacterial systems can involve a nucleic acid sequence, encoding the amino acid sequence for a protein of the subject invention, integrated into a protein expression vector appropriate to the host in which the vector will reside. Further, the sequences can be optimized for expression in specific plants.

The term "native" or "wild type" as used herein, refers to a plant cell, seed, plant component, plant tissue, plant organ, or whole plant that has not been genetically modified or treated in an experimental sense. Wild-type cells, seed, components, tissue, organs, or whole plants may be used as controls to compare level of expression and the extent and nature of trait modification with cells, tissue, or plants of the same species in which a polypeptide's expression is altered, e.g., in that is has been knocked out, over-expressed, or ectopically expressed.

The present invention evaluated the drought resistance of 14 transgenic *Arabidopsis*-overexpressing PYLs driven by the constitutive 35S cauliflower mosaic virus (CaMV) promoter, the stress-inducible RD29A promoter, the guard cell-specific GC1 and ROP11 promoters (20, 21), and the green tissue-specific ribulose bisphosphate carboxylase small subunit (RBCS) RBCS-1A promoter (22). It was found that, relative to the WT and all other combinations, pRD29A::PYL9 transgenic *Arabidopsis* plants had both greater drought resistance and accelerated drought- or ABA-induced leaf senescence. Additionally, it was discovered that ABA induces leaf senescence in an ethylene-independent manner and that PYL9 promotes ABA-induced leaf senescence by inhibiting PP2Cs and activating SnRK2s. ABA-activated SnRK2s then mediate leaf senescence by phosphorylation of related to ABA-Insensitive 3/VP1 (RAV1) and ABF2 transcription factors, which then up-regulate the expression of ORE1 and other NAC transcription factors, thereby activating expression of SAGs. Previous research has suggested that transgenic plants with delayed leaf senescence are more resistant to drought stress (1). The importance of ABA-induced leaf senescence under drought stress was examined and surprising it was found that the increased leaf senescence in pRD29A::PYL9 transgenic plants helps generate a greater osmotic potential gradient, which causes water to preferentially flow to developing tissues. Therefore, hypersensitivity to ABA leads to increased senescence and death of old leaves but survival of young tissues during severely limited water conditions through promoting summer dormancy-like responses (23).

Screening Transgenic *Arabidopsis* for Drought-Stress Survival.

Figure 6:
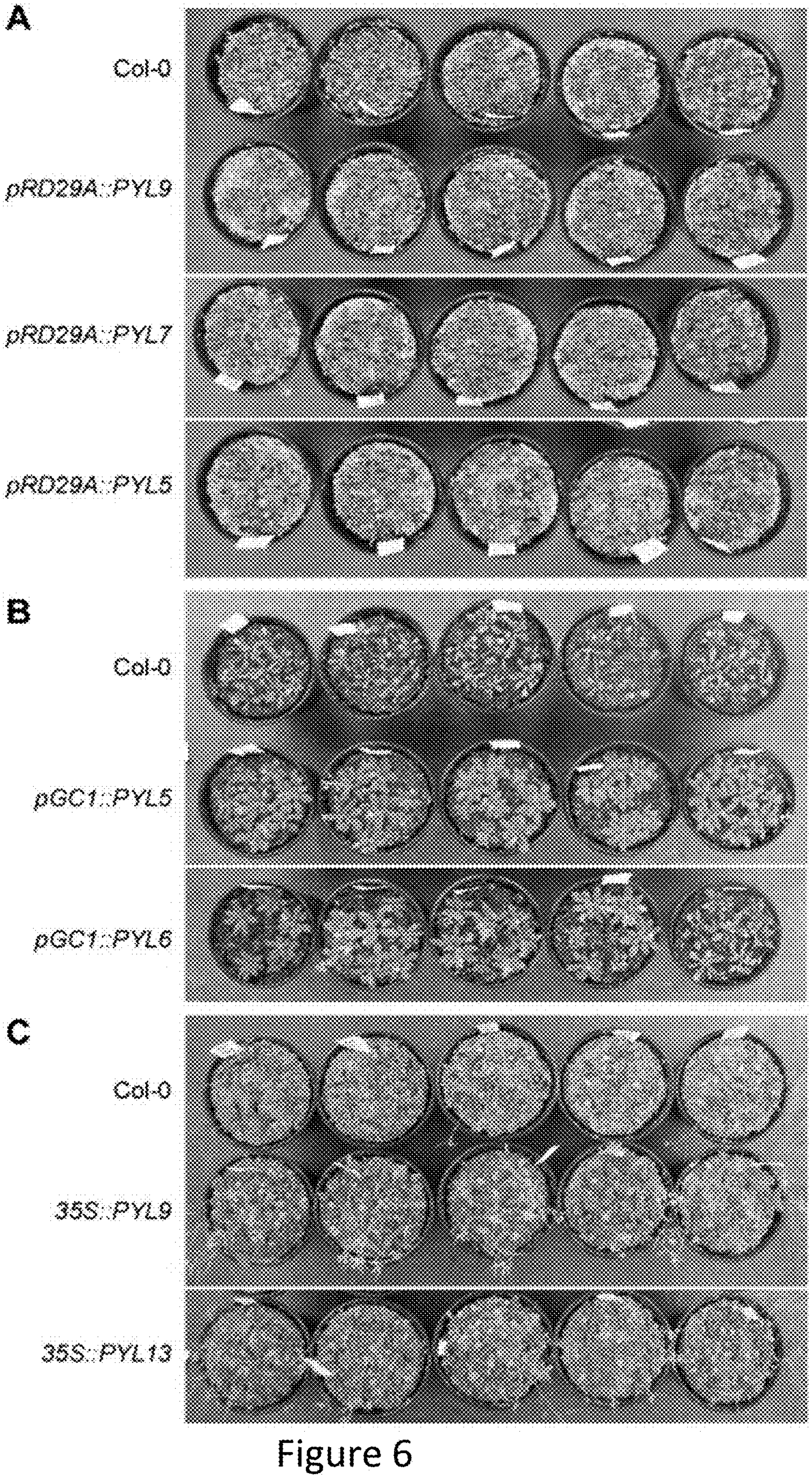
FIGS. 6A, 6B and 6C show drought resistance screening of PYL transgenic *Arabidopsis*. Two-week-old plants were subjected to drought stress by withholding water for 20 d, by which time most Col-0 WT plants had died. Images of representative plants after 20 d of drought treatment.

In *Arabidopsis*, the expression of many PYLs is down-regulated by osmotic stress, which may constitute a negative feedback loop that reduces drought responses (24). In principle, expression modifications that allow general, tissue-specific, or stress-inducible overexpression of PYLs should amplify ABA signaling and increase drought resistance in transgenic plants. Based on this assumption, the following five promoters were used for PYL overexpression: the 35S CaMV promoter, the stress-inducible RD29A promoter, and the tissue-specific promoters GC1, ROP11, and RBCS-1A. Transgenic plants from a total of 65 different promoter-PYL combinations were generated and evaluated for drought-stress resistance (FIG. 1A and FIG. 6). The results indicated that drought resistance was increased by PYLs driven by 35S, pRD29A, and pGC1 promoters but not by the pRBCS-1A promoter. The pGC1-driven lines performed better than the lines driven by the other guard cell-specific promoter, pROP11. Among the combinations, survival was highest for 35S::PYL3/9/13, pRD29A::PYL7/9, and pGC1::PYL3/5/6/7/11 lines. These top drought-resistant lines preferentially cluster on the monomeric PYLs, especially PYL7 and PYL9, which have very high affinities to ABA (16).

Figure 7:
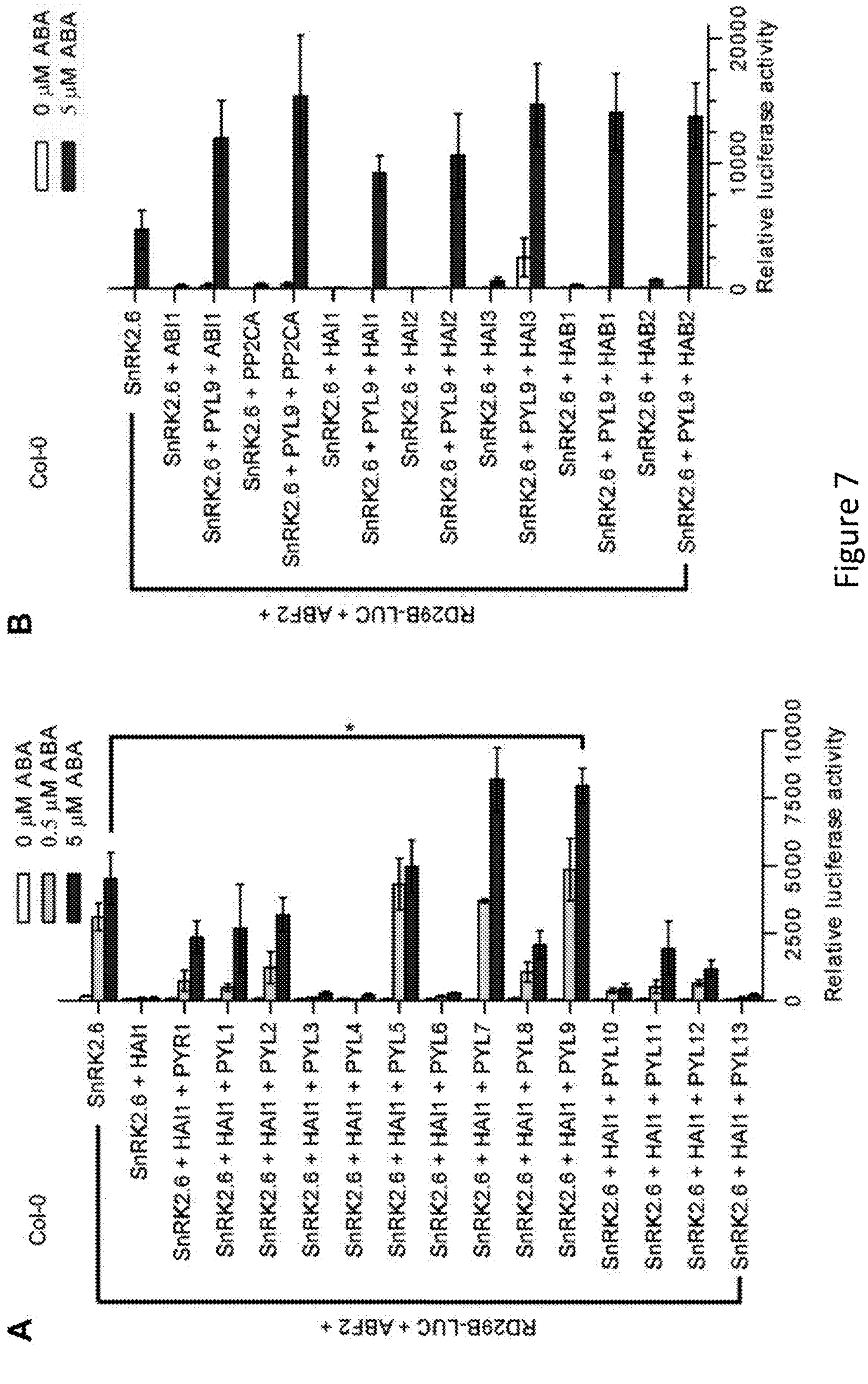
FIGS. 7A and 7B show that PYL9 inhibits all tested PP2Cs in protoplasts.

The PYLs in a transient expression assay in *Arabidopsis* protoplasts (25) was evaluated. Highly ABA-induced 1 (HAI1), HAI2, and HAI3 PP2Cs interact with only a few of these PYLs, even in the presence of 10 μM ABA (24). Transfections of HAI1 inhibited RD29B-LUC expression. PYL3, PYL4, PYL6, or PYL13 did not inhibit HAI1, whereas cotransfections of HAI1 with PYL5, PYL7, or PYL9 strongly enabled the ABA-dependent induction of RD29B-LUC expression (FIG. 7A). Furthermore, cotransfections of PYL9 together with each of the PP2Cs strongly enabled the ABA-dependent induction of RD29B-LUC (FIG. 7B). Similar to the ABA-independent inhibition of ABA-insensitive 1 (ABI1) by PYL10 (16, 25), PYL9 can partially inhibit HAI3 activity in the absence of exogenous ABA. These results suggested that PYL9 strongly inhibits the phosphatase activities of clade A PP2Cs in plant cells, an inhibition that activates the core ABA signaling pathway and is believed to be involved in the drought resistance of pRD29A::PYL9 transgenic plants.

PYL9 transcripts were significantly more abundant in pRD29A::PYL9 lines than in the WT under drought stress (FIG. 8A). Application of ABA after water was withheld for 12 d significantly increased the drought resistance of the pRD29A::PYL9 transgenic plants after flowering (FIGS. 1 B and C). The delayed wilting and drying in pRD29A::PYL9 transgenic plants was correlated with a reduction in water loss from the soil, indicating a reduction in transpiration. This result revealed that PYL9, when driven by the pRD29A promoter, is useful for generating transgenic plants that are extremely resistant to drought when treated with ABA or ABA-mimicking compounds (26, 27). The pRD29A::PYL9 transgenic lines were selected for additional study (FIG. 8B).

pRD29A::PYL9 Confers Drought Resistance to Both *Arabidopsis* and Rice.

Figure 2:
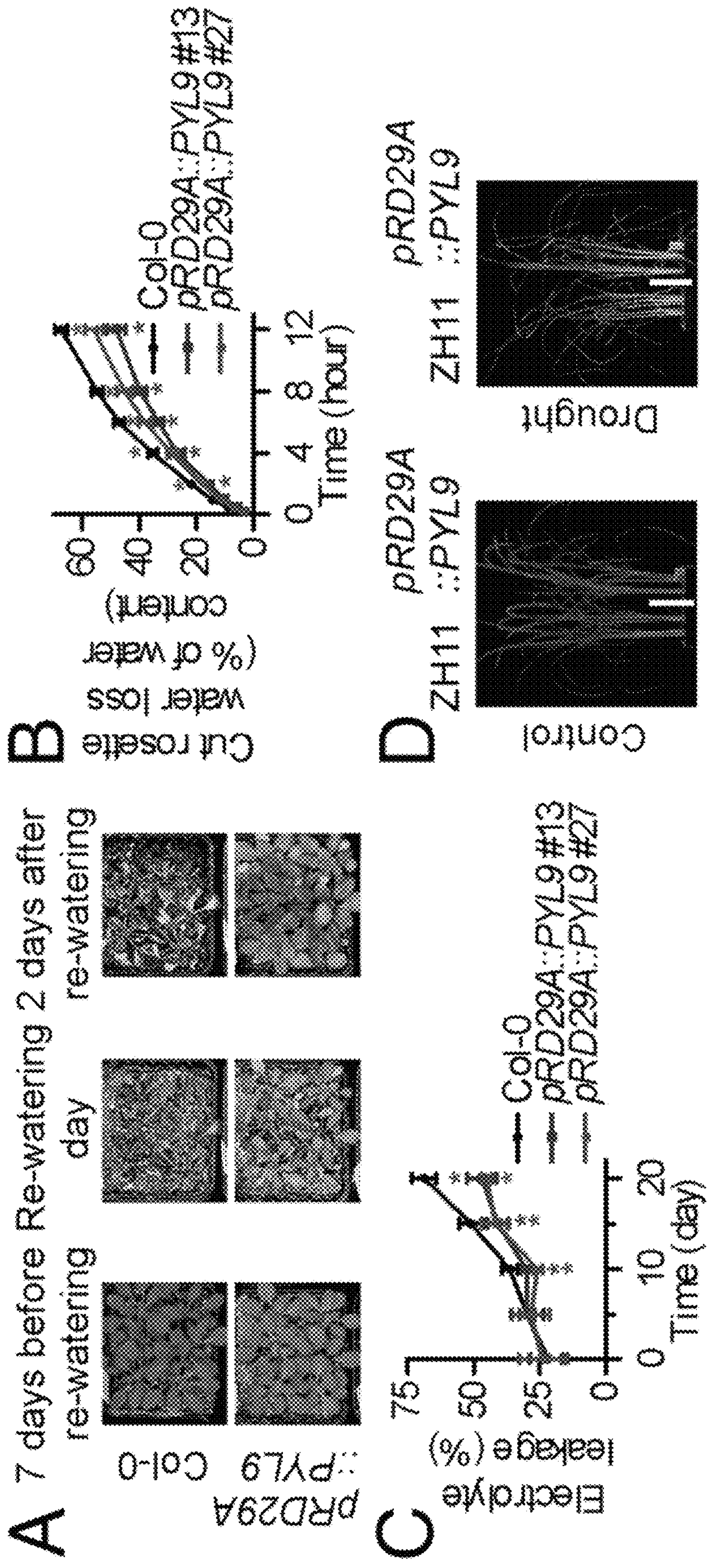
FIGS. 2A, 2B, 2C and 2D show that pRD29A::PYL9 transgenic plants exhibit improved drought-stress resistance in both *Arabidopsis* and rice.

The *Arabidopsis* pRD29A::PYL9 transgenic lines also exhibited increased drought resistance before flowering under short-day conditions (FIG. 2A). The greater drought-stress survival of pRD29A::PYL9 lines was associated with reduced water loss (FIG. 2B), reduced cell membrane damage (FIG. 2C), reduced transpiration rate and stomatal conductance (FIGS. 8C and D), enhanced photosynthetic rate and water use efficiency (FIGS. 8E and F), reduced accumulation of toxic hydrogen peroxide, and enhanced activities of antioxidant enzymes (FIG. 8G). As a result, the total biomass was greater in pRD29A::PYL9 lines than in the WT after drought treatment but did not differ statistically from the WT in the absence of drought treatment (FIG. 8H). These results showed that the pRD29A::PYL9 transgene confers drought resistance to *Arabidopsis* in at least two ways (i.e., by reducing water loss and by reducing oxidative injury).

Figure 8:
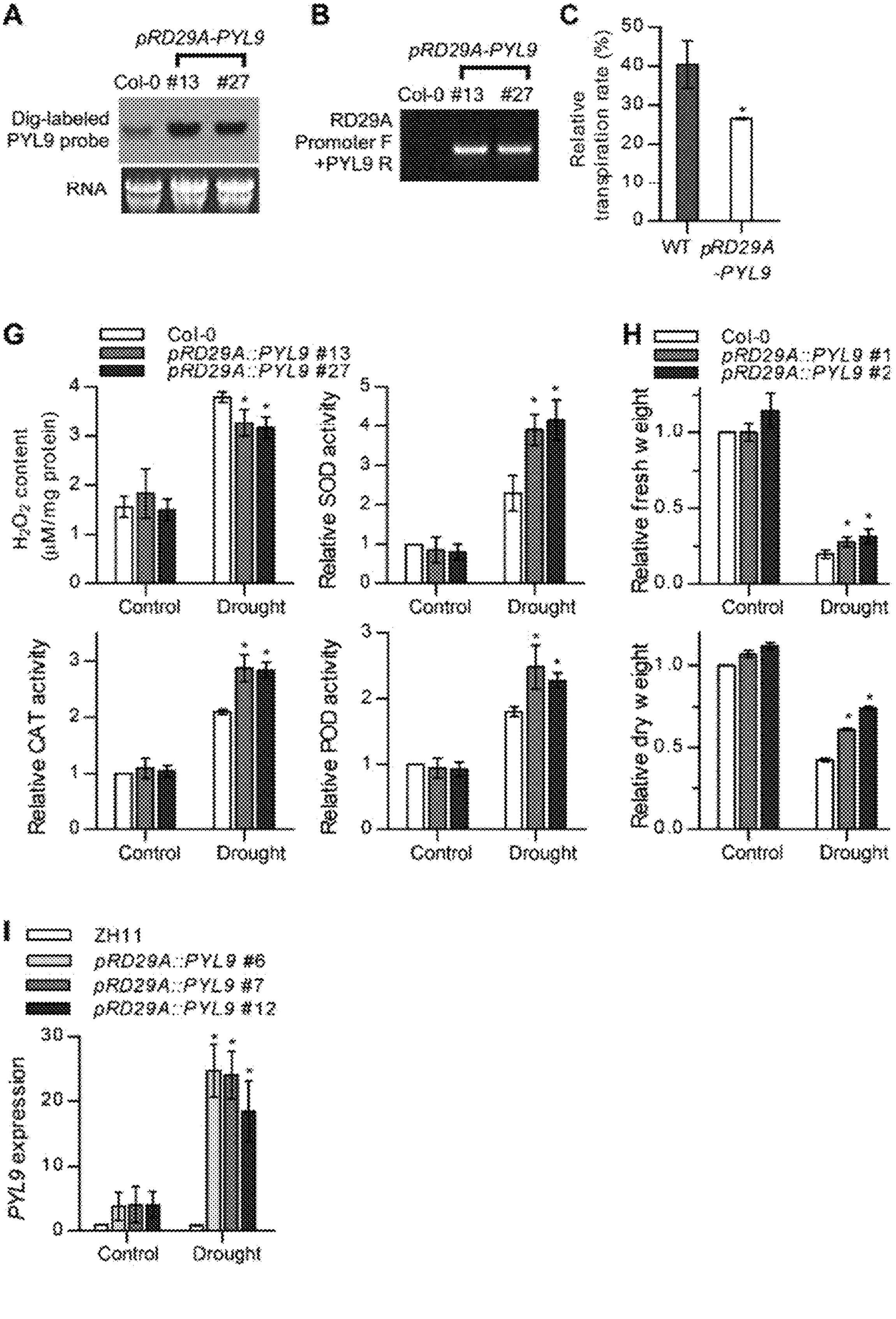
FIGS. 8A, 8B, 8C, 8D, 8E, 8F, 8G, 8H, 8I and 8J show that stress-inducible overexpression of PYL9 improves drought-stress resistance.
Figure 8:
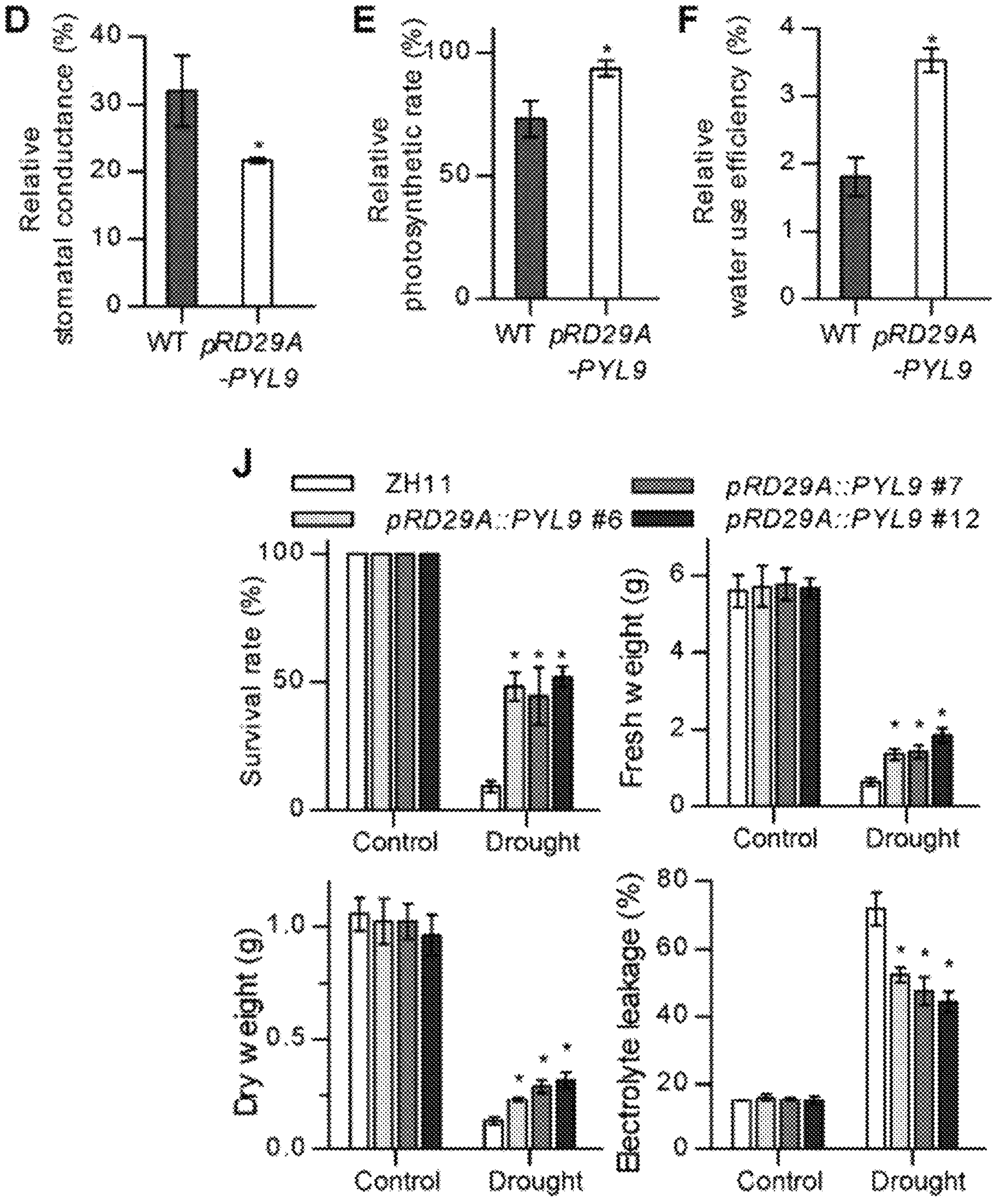

To determine whether pRD29A::PYL9 may confer drought resistance in crop plants, pRD29A::PYL9 transgenic rice (*Oryza sativa* L.) was generated in the *japonica* variety Zhonghua 11 (ZH11), in which PYL9 expression was dramatically induced by drought stress (FIG. 8I). pRD29A::PYL9 transgenic rice exhibited increased drought resistance (FIG. 2D). After a 2-wk drought treatment, nearly 50% of pRD29A::PYL9 transgenic rice growing in soil survived, but only about 10% of the ZH11 WT plants survived (FIG. 8J). Although pRD29A::PYL9 increased survival, total biomass, and cell membrane integrity of transgenic rice under drought conditions, the transgene did not adversely affect plant growth and development under well-watered conditions (FIGS. 8 H and J). These results showed that pRD29A::PYL9 increases drought resistance in rice without retarding growth under well-watered conditions.

PYL9 Promotes ABA-Induced Leaf Senescence in Both *Arabidopsis* and Rice.

Figure 9:
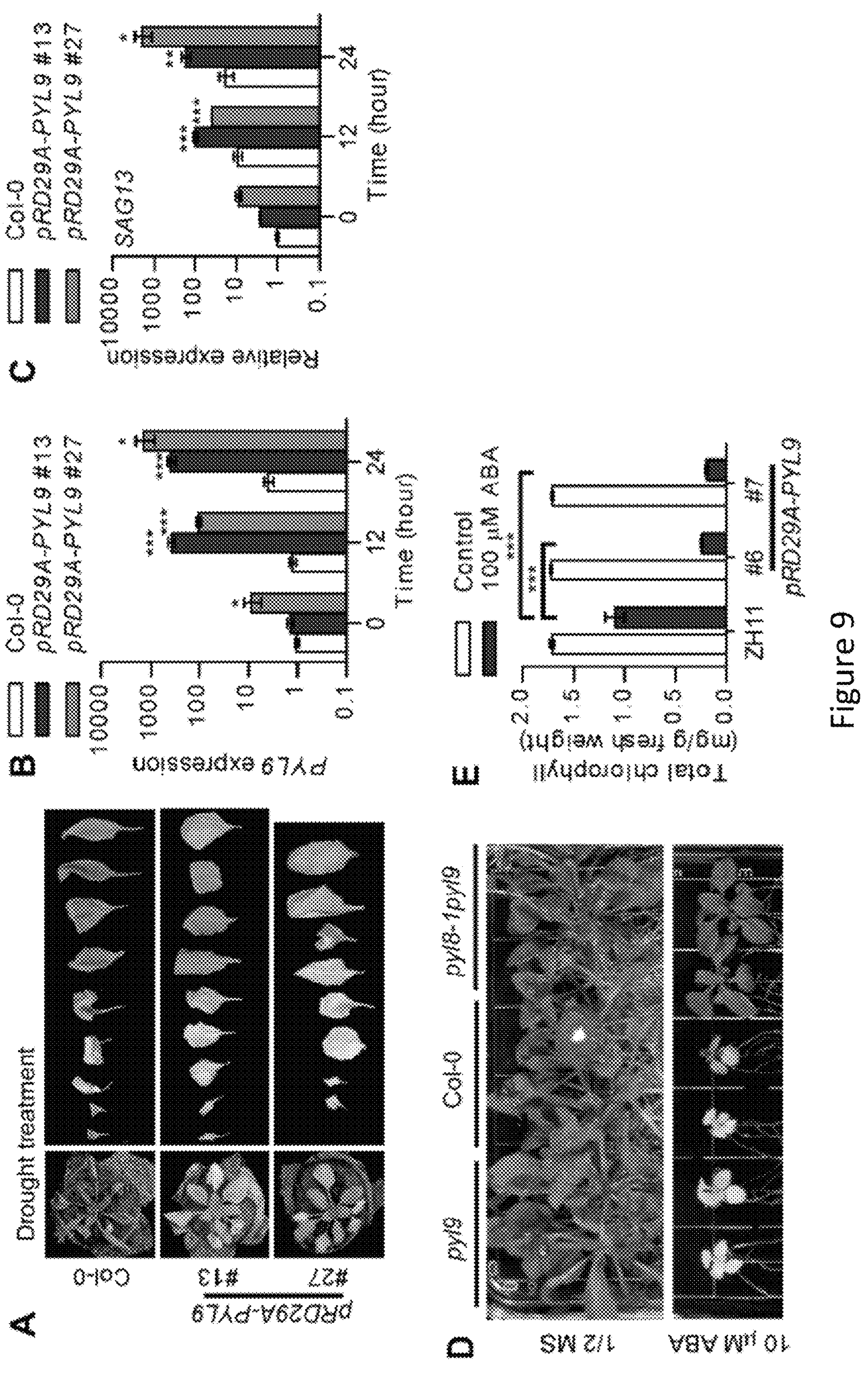
FIGS. 9A, 9B, 9C, 9D and 9E show PYL9 promotes drought- and ABA-induced leaf yellowing in *Arabidopsis*.

After the drought treatment, it was evident that older leaves of pRD29A::PYL9 lines became yellow, sooner than in the Columbia-0 (Col-0) WT (FIG. 2A and FIG. 9A). ABA-induced leaf yellowing was also accelerated in pRD29A::PYL9 transgenic plants (FIG. 3A). Consistent with its visible phenotypes, pRD29A::PYL9 lines had a lower chlorophyll level than the Col-0 WT after treatment with 20 μM ABA (FIG. 3B). SAGs are molecular markers of senescence and especially, ABA-induced senescence (12). Consistent with the elevated PYL9 expression (FIG. 9B), both SAG12 and SAG13 were more strongly induced after ABA treatment in mature leaves of pRD29A::PYL9 lines than in those of the WT (FIG. 3C and FIG. 9C). This result showed that pRD29A::PYL9 accelerates ABA-induced leaf senescence of older leaves in *Arabidopsis*.

Figure 10:
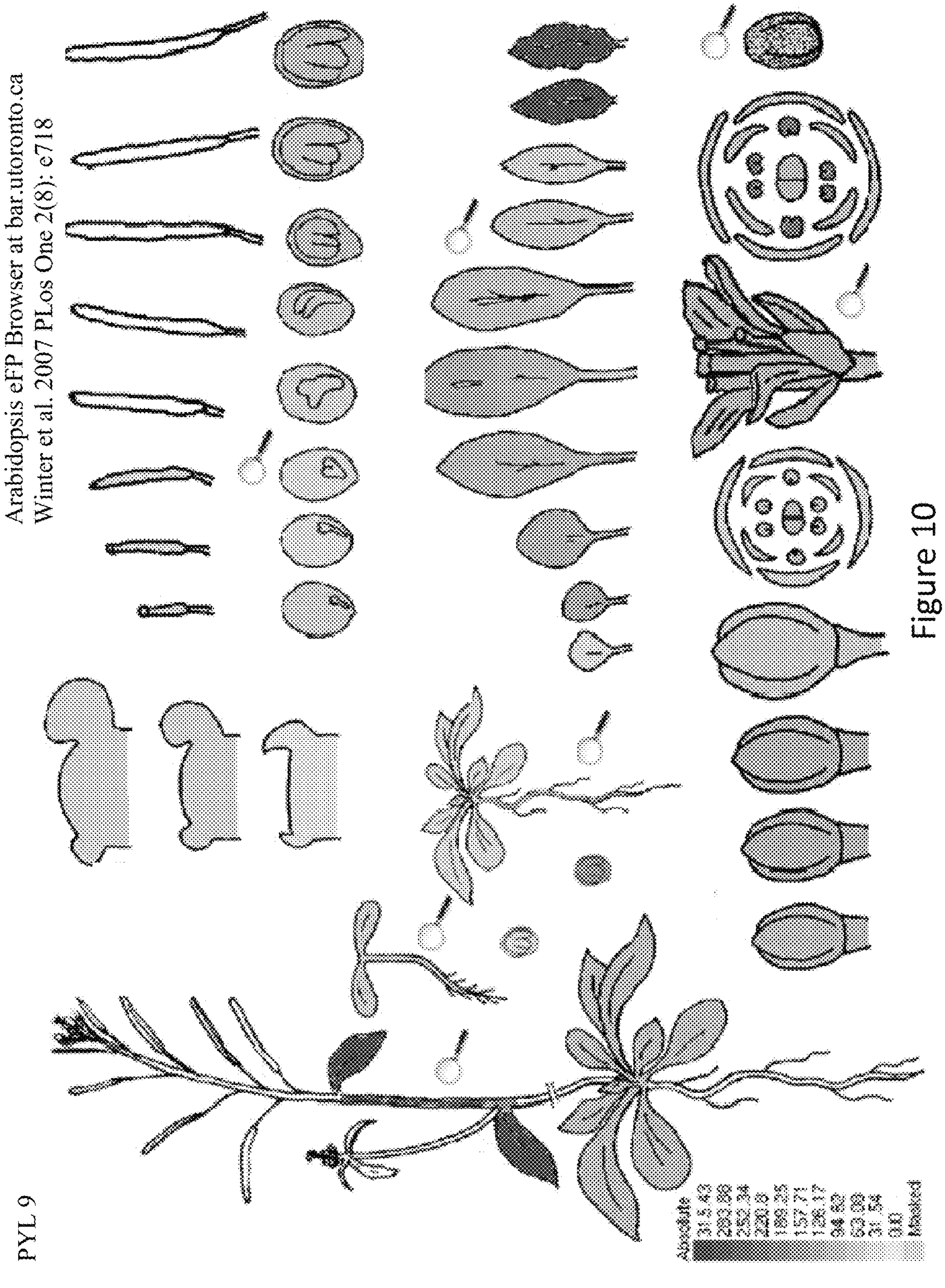
FIG. 10 shows the PYL9 and SAG12 expression in *Arabidopsis* according to the *Arabidopsis* electronic fluorescent pictograph (eFP) browser (bar.utoronto.ca/efp/cgi-bin/efpWeb.cgi).
Figure 10:
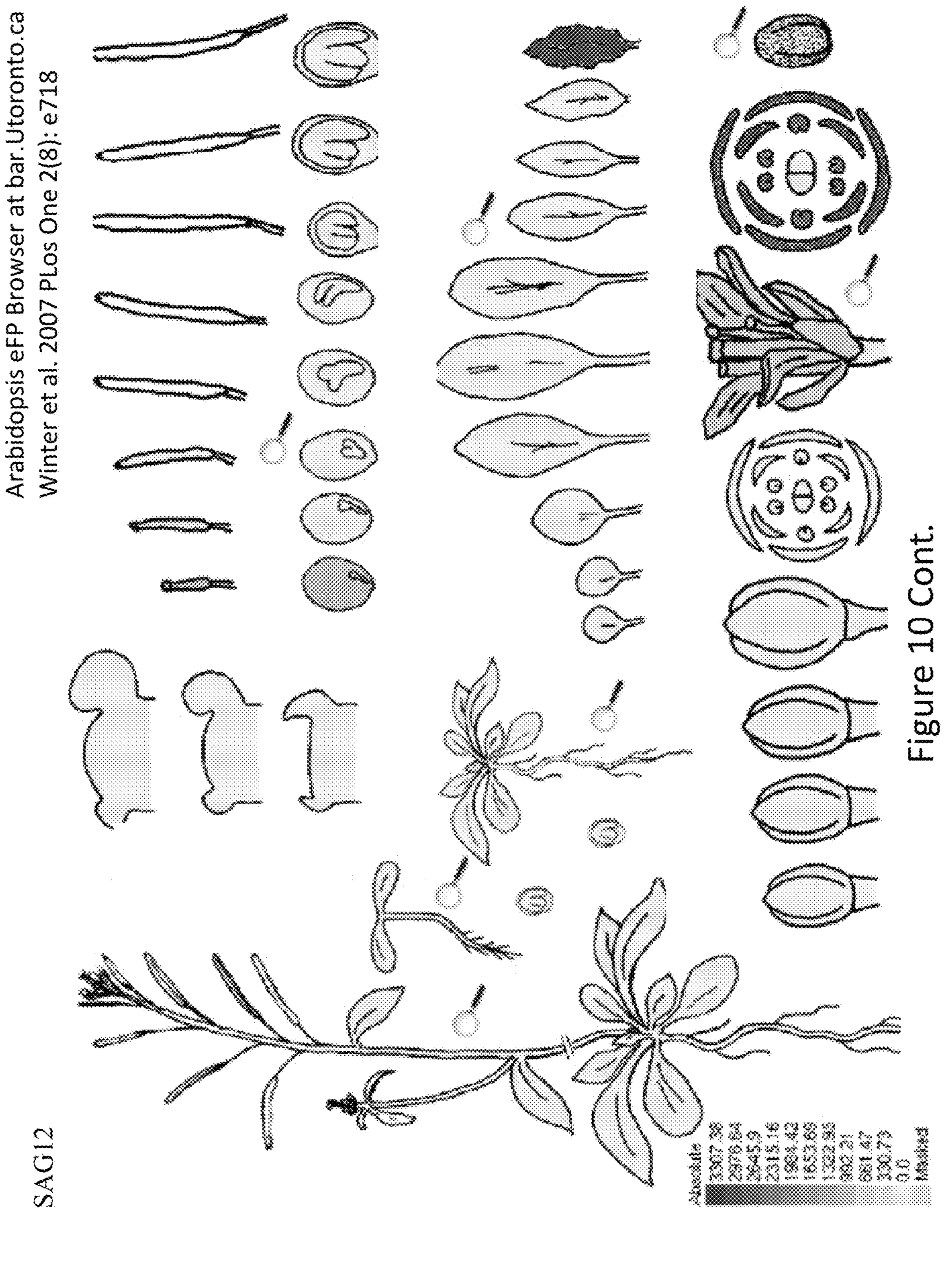

Enhanced drought survival and senescence are both associated with ABA signaling. To verify that PYL9 mediated these responses by making the plants hypersensitive to ABA, we analyzed the leaf yellowing of the pyl9 transferred DNA (T-DNA) insertion mutant after ABA treatment of plate-grown seedlings. ABA-induced leaf yellowing was lower in the pyl9 mutant than in the WT under low light (30-45 μmol $m^{-2}$ $s^{-1}$) (FIGS. 3 D and E) but not under normal light (80-100 μmol $m^{-2}$ $s^{-1}$) (FIG. 9D) because of genetic redundancy. Moreover, the pyl8-1pyl9 double mutant was less sensitive than the pyl9 mutant to ABA-induced leaf yellowing, indicating that PYL9 and PYL8 function together in ABA-induced leaf senescence. Furthermore, PYL9 is highly expressed in senescent leaves and stamens according to the *Arabidopsis* electronic fluorescent pictograph (eFP) browser, which is consistent with the expression of SAG12 (FIG. 10). These results confirm that PYL9 functions in both ABA-induced drought survival and senescence by hypersensitizing *Arabidopsis* to ABA.

ABA-induced leaf yellowing was also accelerated in pRD29A::PYL9 transgenic rice (FIG. 3F and FIG. 9E). After ABA treatment, severe yellowing was evident in the third oldest leaves of the pRD29A::PYL9 lines but not those of the ZH11 WT. Moreover, two SAGs, Osh36 and Osl85 (9), were more strongly induced after ABA treatment in the third-oldest leaves of pRD29A::PYL9 rice lines than in those of the ZH11 WT (FIG. 3G). These results show that PYL9 also mediates ABA-induced leaf senescence in rice.

ABA Induces Leaf Senescence Through the Core ABA Signaling Pathway.

Figure 11:
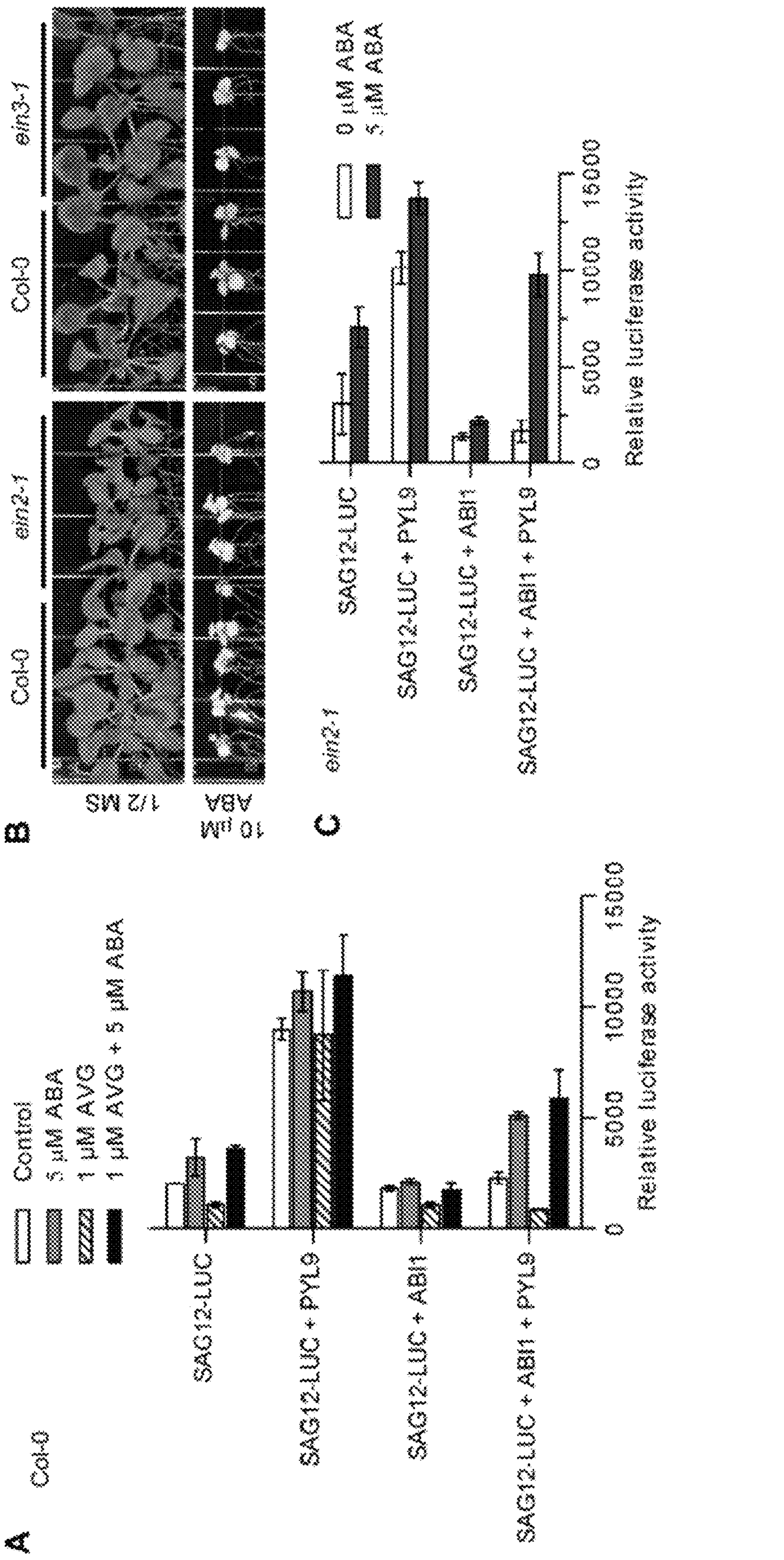
FIGS. 11A, 11B and 11C show that ABA-induced senescence is not mediated through its promotion of ethylene production.

To investigate whether ABA induction of senescence requires ethylene, protoplasts were treated with the ethylene biosynthesis inhibitor aminoethoxyvinylglycine (AVG). It was found that AVG treatment decreased SAG12-LUC expression in the absence of ABA (FIG. 11A), consistent with the known role of ethylene in promoting senescence. However, AVG treatment did not inhibit either ABA-induced or PYL9-enhanced SAG12-LUC expression (FIG. 11A). It was found that ABA-induced leaf yellowing was not reduced in the ethylene-resistant mutants ein2-1 and ein3-1 (FIG. 11B). Furthermore, ABA-induced and PYL9-enhanced SAG12-LUC expression was not blocked in ein2-1 mutant protoplasts (FIG. 11C). These results suggest that the induction of senescence by ABA is not mediated through ethylene.

Figure 12:
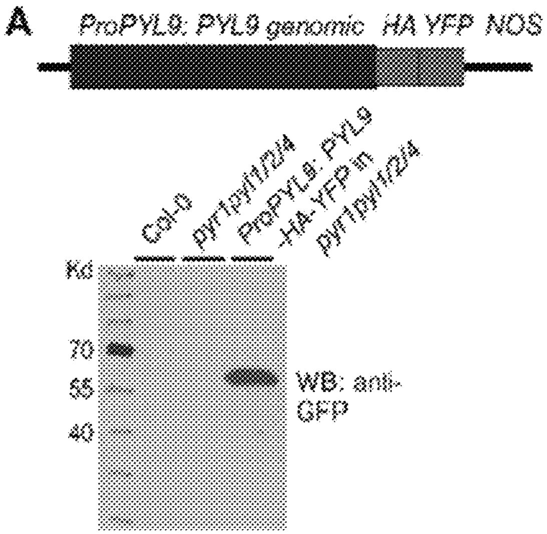
FIGS. 12A, 12B, 12C, 12D, 12E, 12F, 12G 12H and 12I show that PP2Cs are negative regulators of leaf senescence.
Figure 12:
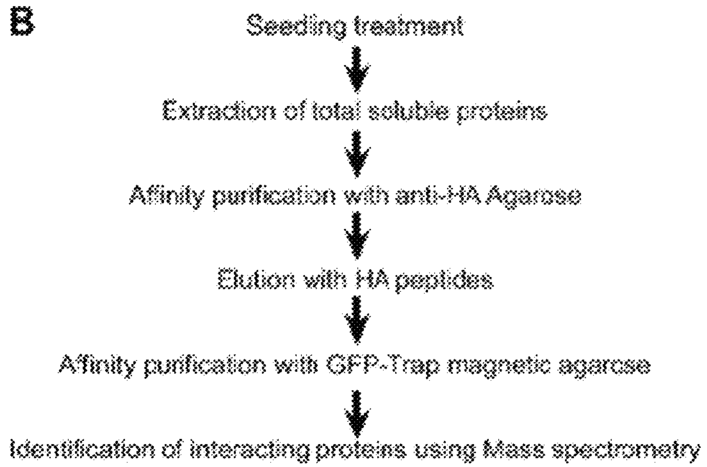
Figure 12:
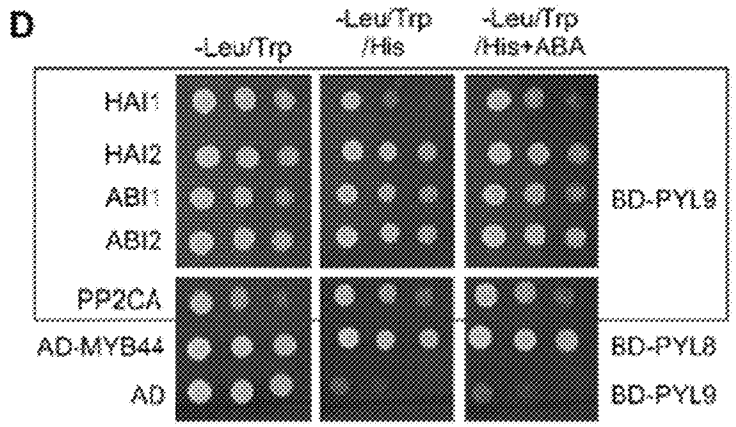

Transgenic *Arabidopsis* plants were generated by expressing HA- and YFP-tagged PYL9 under the native PYL9 promoter (ProPYL9:PYL9-HA-YFP) (FIG. 12A) and isolated PYL9-associated proteins using tandem affinity purification (FIG. 12B and Table 1). The associated proteins mainly included several PP2Cs, such as HAB2, PP2CA, and ABI1, in an ABA- or osmotic stress-enhanced manner (FIG. 12C). PYL9 interacted with all PP2Cs tested in an ABA-independent manner in yeast two-hybrid (Y2H) assays (FIG. 12D). The 788-bp fragment of the SAG12 promoter (SAG12-LUC) (FIG. 12E) was fused to the LUC reporter gene and used the construct as a senescence-responsive reporter. The 788-bp SAG12 promoter contains the 9-mer sequence which is the preferred binding site of ORE1 (28). All PP2Cs decreased SAG12-LUC expression in the presence of ABA (FIGS. 12F and 12G). The inhibition of SAG12-LUC expression by ABI1 can be released by coexpression of PYL9 (FIG. 12F). Moreover, ABA-induced leaf yellowing was weaker in the abi1-1 mutant than in the *Landsberg erecta* (Ler) WT (FIG. 4A and FIG. 12H). The abi1-1 mutant is ABA-resistant and contains a G180D point mutation. PYLs do not interact with or inhibit $ABI1^{G180D}$, even in the presence of ABA (13). These results indicated that PP2Cs inhibit ABA-induced senescence.

It was hypothesized that PYL9 may promote leaf senescence by activating SnRK2s. The snrk2.2/3/6 triple mutant was insensitive to ABA-induced leaf yellowing (FIG. 4B and FIG. 12I). Moreover, SAG12-LUC expression was not enhanced by ABA treatment in snrk2.2/3/6 triple-mutant protoplasts, but ABA induction of SAG12-LUC expression in such protoplasts could be recovered by transfection of SnRK2.6 (FIG. 4C), suggesting that ABA-induced SAG12 expression depends on the SnRK2s. The activation of SAG12-LUC expression by PYL9 was abolished in snrk2.2/3/6 triple-mutant protoplasts, but such expression was also recovered with transfection of SnRK2.6. The activation of SAG12-LUC expression by SnRK2.6 was blocked by transfection of ABI1, which can be released by PYL9. These results suggest that PYL9 promotes ABA-induced leaf yellowing and SAG12 expression through core ABA signaling.

Phosphorylation of ABFs by SnRK2s Facilitates ABA-Induced SAG12 Promoter Activity in Leaf Protoplasts.

Figure 13:
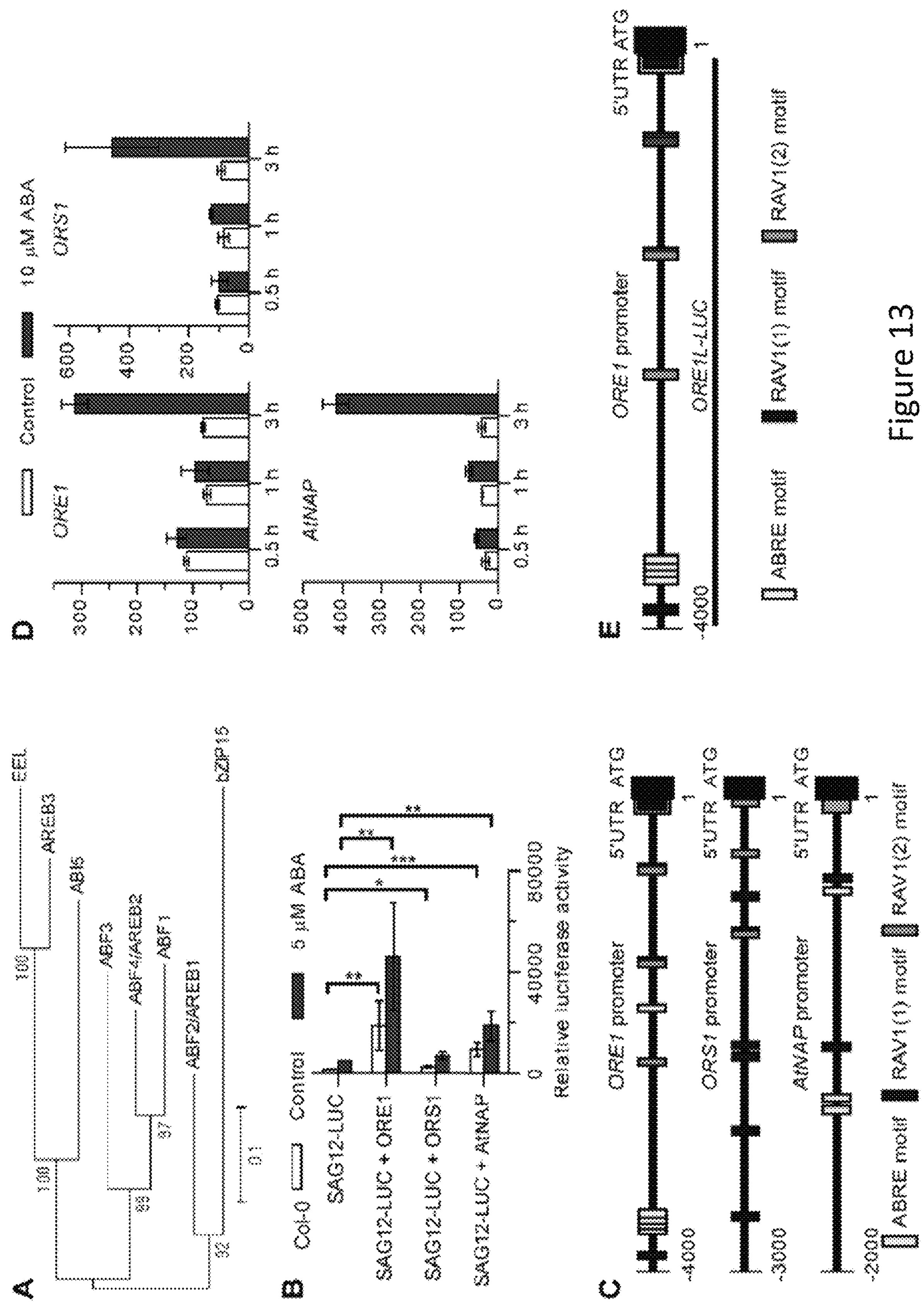
FIGS. 13A, 13B, 13C, 13D and 13E show the ABA-induced expression of senescence-related NACs.

ABA-activated SnRK2s phosphorylate ABF transcription factors, which activate these factors and enable them to regulate expression of ABA-responsive genes (15). To identify the transcription factors involved in ABA-induced leaf senescence, several ABFs, were cloned including ABF2, ABI5, enhanced EM level (EEL), and AREB3, and coexpressed them with SAG12-LUC in Col-0 leaf protoplasts (FIG. 4D and FIG. 13A). It was found that SAG12-LUC expression in protoplasts was dramatically increased by ABF2, was less dramatically but significantly increased by ABI5 and EEL, and was not increased by AREB3 (FIG. 4D). The phosphorylation of ABF2 at amino acid residues S26, S86, S94, and T135 is important for stress-responsive gene expression in *Arabidopsis*, and these sites are putatively phosphorylated by SnRK2s (15, 25). Expression of SnRK2.6 significantly enhanced the ability of ABF2 to increase SAG12-LUC expression in the presence of ABA. Furthermore, $ABF2^{S26DS86DS94DT135D}$ constitutively increased SAG12-LUC expression in the snrk2.2/3/6 triple-mutant protoplasts (FIG. 4E). These results suggested that phosphorylation of ABFs by SnRK2s promotes activity of the ABA-induced leaf senescence pathway.

Figure 4:
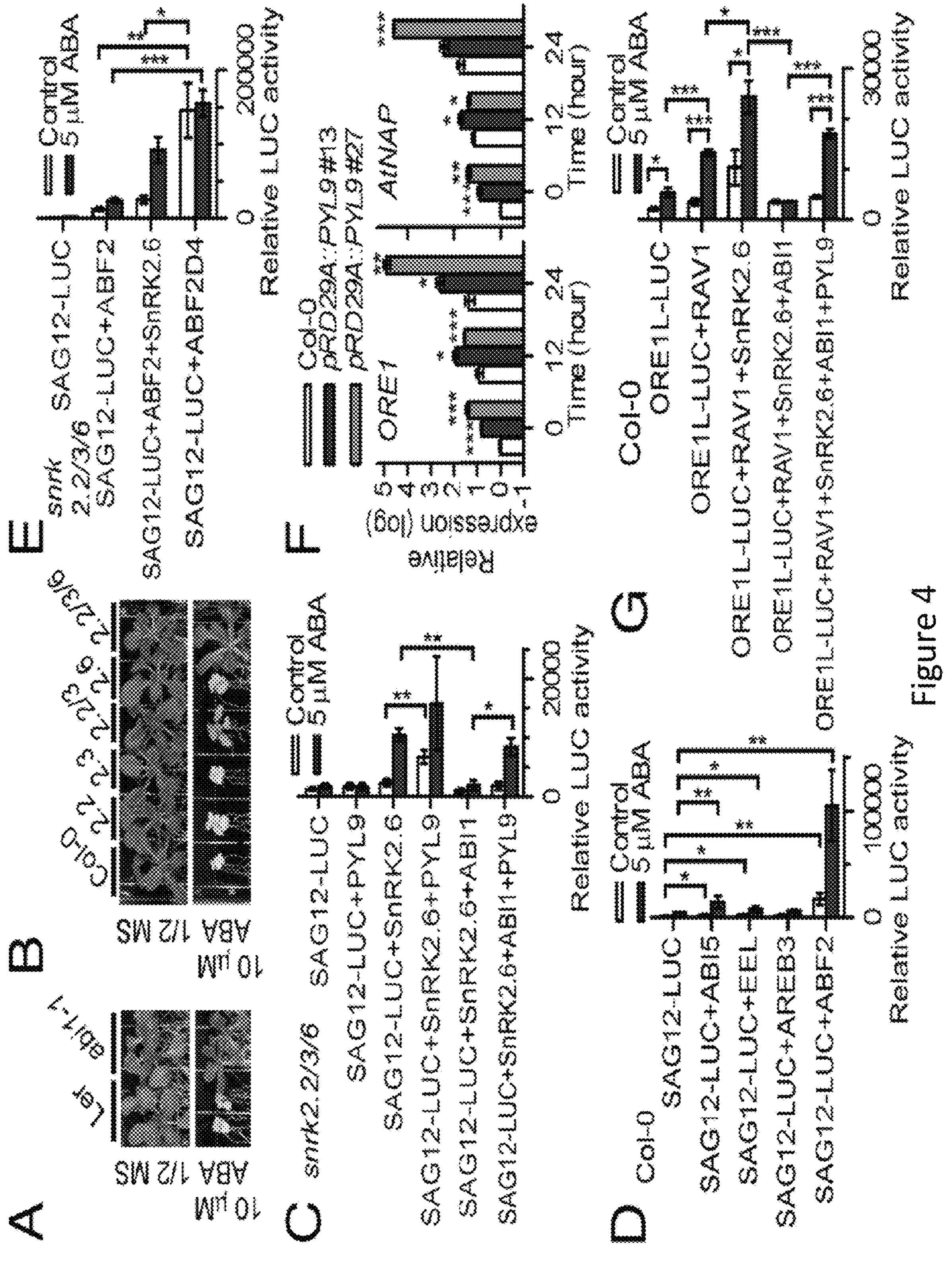
FIGS. 4A, 4B, 4C, 4D, 4E, 4F, and 4G show that core ABA signaling promotes ABA-induced leaf senescence.

Leaf senescence is promoted by several NAC transcription factors, such as ORE1 (5), ORS1 (6), and AtNAP (7). ABA-induced leaf senescence was reported to be delayed in ore1 mutant leaves (29). SAG12-LUC expression was clearly increased by ORE1 and AtNAP and slightly increased by ORS1 (FIG. 13B). The ORE1 and AtNAP promoter regions contain several abscisic acid-responsive element (ABRE) motifs and RAV1 binding sites (FIG. 13C). ABRE motifs are the binding sites for the ABF transcription factors, which the results suggested to be positive regulators of senescence (FIGS. 4 D and E). ABA-activated SnRK2s phosphorylate RAV1 (30), which positively regulates leaf senescence in *Arabidopsis* (31). According to the *Arabidopsis* eFP browser, expression of ORE1, ORS1, and AtNAP is enhanced by ABA (FIG. 13D). ABA treatment, indeed, induced the expression of ORE1 and AtNAP in mature leaves, and the expression levels were higher in pRD29A::PYL9 lines compared with those of the WT (FIG. 4F). A 3,984-bp fragment of the ORE1 promoter was fused to the LUC reporter gene (ORE1L-LUC) (FIG. 13E) to use as a senescence-responsive reporter. According to the AthaMap, the 3,984-bp ORE1 promoter contains multiple RAV1(1) and RAV1(2) motifs, which are the preferred binding sites for RAV1. The ORE1L-LUC expression was enhanced by RAV1 and SnRK2.6 and repressed by ABI1 (FIG. 4G). Expression of PYL9 released the inhibition of ABI1 on ORE1-LUC expression in an ABA-dependent manner. These results suggested that ABA core signaling up-regulates expression of SAGs through phosphorylation of both ABFs and RAV1 transcription factors.

Figure 3:
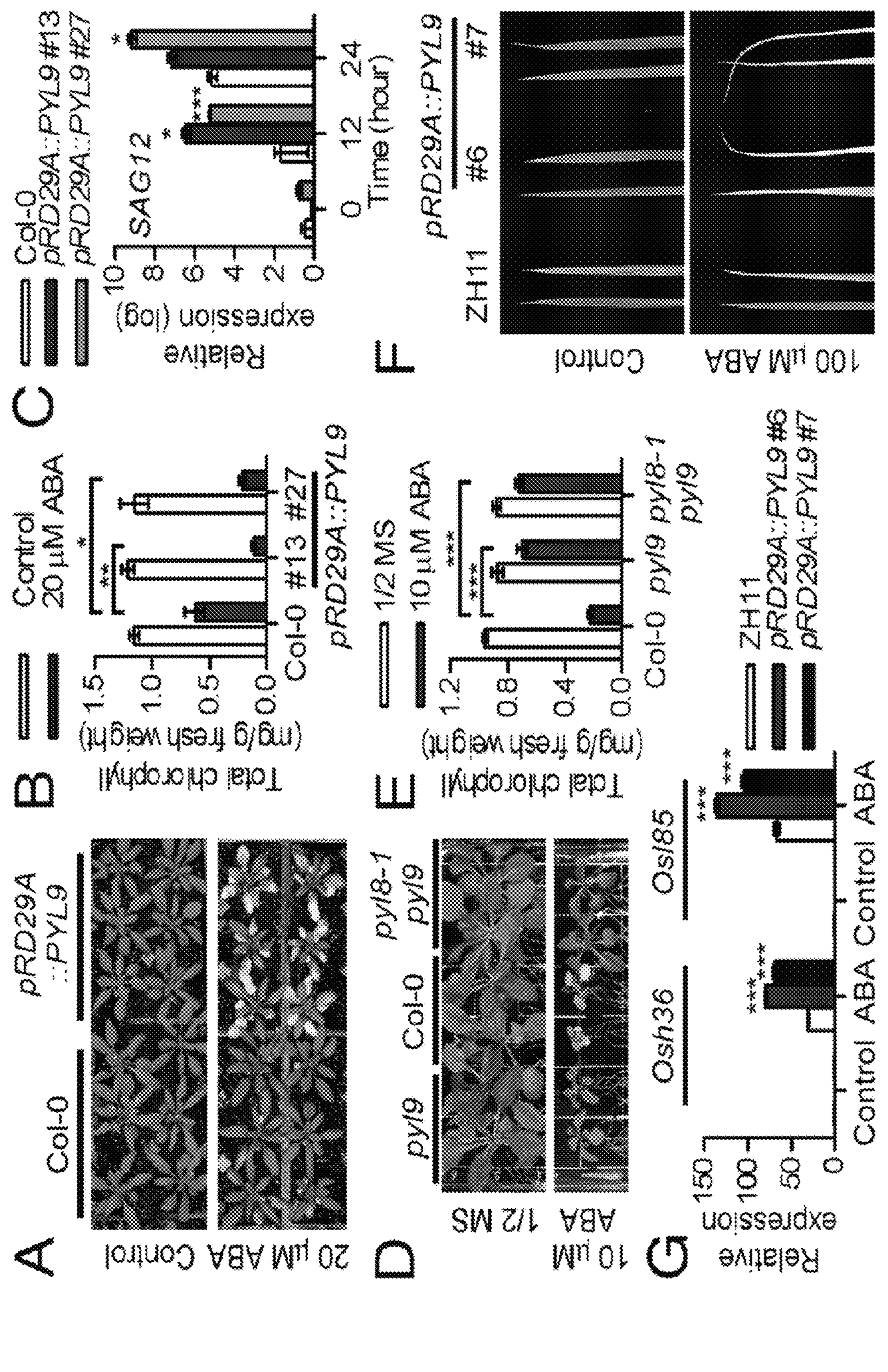
FIGS. 3A, 3B, 3C, 3D, 3E, 3F and 3G show that PYL9 promotes ABA-induced leaf senescence in both *Arabidopsis* and rice.
Figure 5:
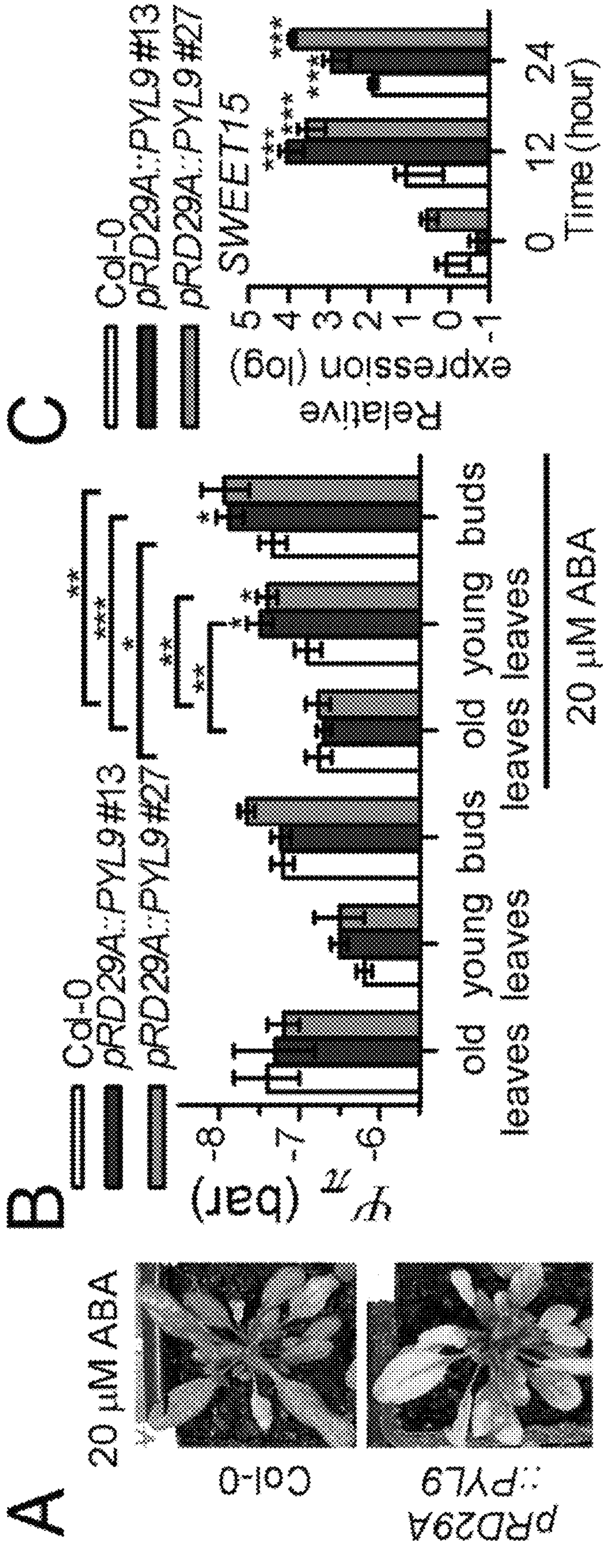
FIGS. 5A, 5B and 5C show that pRD29A::PYL9 transgenic plants exhibit an increased within-plant osmotic potential gradient.

Stressed pRD29A::PYL9 Transgenic Plants Display Enhanced Osmotic Potential Gradients Between Senescing Leaves and Buds.

pRD29A::PYL9 transgenic plants are hypersensitive to ABA-induced leaf senescence (FIG. 3). In these plants, leaf yellowing spreads from older to younger leaves (FIG. 5A). Leaf wilting in pRD29A::PYL9 transgenic plants was observed after 3 d of continuous ABA treatment, even in plants that were well-watered (FIG. 5A). This unusual event suggests that water transport to senescing leaves was reduced or blocked. Water moves from areas of high water potential to areas of low water potential, and plants control water potential, in part, by regulating osmotic potential (P). It was found that ABA treatment reduced the osmotic potential in the developing bud tissue but not in the old leaves (FIG. 5B). The osmotic potential was lower in developing tissues of pRD29A::PYL9 lines than in the WT but did not differ in old leaves of the transgenic plants vs. the WT. Thus, the osmotic potential gradient was greater in pRD29A::PYL9 lines than in the WT. As noted above, this gradient would cause water to move preferentially to developing tissues but not to senescing leaves, especially in pRD29A::PYL9 lines. Senescence, which is associated with the remobilization of carbohydrate and nitrogen from the senescing tissue to the developing or storage tissues, contributes to osmotic potential regulation. Carbohydrate is transported as sucrose to sink tissues through the phloem. The key step for phloem loading is sucrose efflux, which is mediated by SWEET proteins (32). It was determined that SWEET15/SAG29 is induced in senescing *Arabidopsis* leaves. Induction of SWEET15 expression is greater in mature leaves of pRD29A::PYL9 lines than in those of the WT after ABA treatment (FIG. 5C), suggesting that pRD29A::PYL9 lines have an increased ability to mobilize sucrose from senescing leaves.

Core ABA Signaling Promotes Growth Inhibition and the Expression of Cuticular Wax Biosynthesis Genes.

Figure 14:
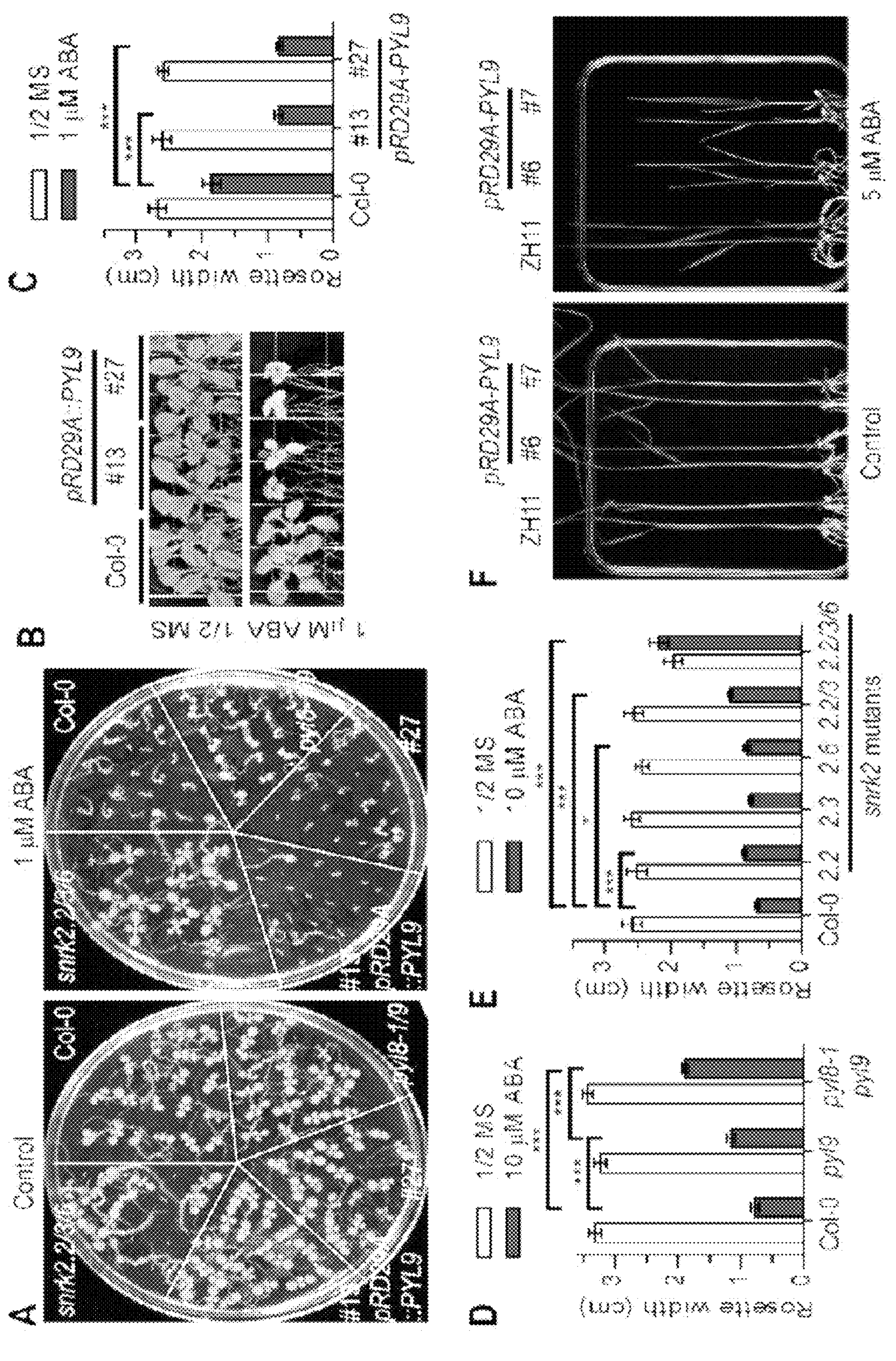
(FIG. 14**H) shows expression of wax biosynthetic genes in snrk2.2/3/6 mutant and abi1-1 mutant. Quantitative RT-PCR was performed at 24 h after transferring 7-d-old seedlings to a medium with or without 10 μM ABA. The expression level of genes in WT (Col-0 and Ler) without ABA treatment was set at one. Error bars indicate SEM (n=3). CER1 (ECERIFERUM 1); KCS2, (3-ketoacyl-CoA synthetase 2); Ler, (*Landsberg erecta*); LTP3, (lipid transfer protein 3); MS, (Murashige and Skoog medium); WSD1, (wax ester synthase 1).
Figure 14:
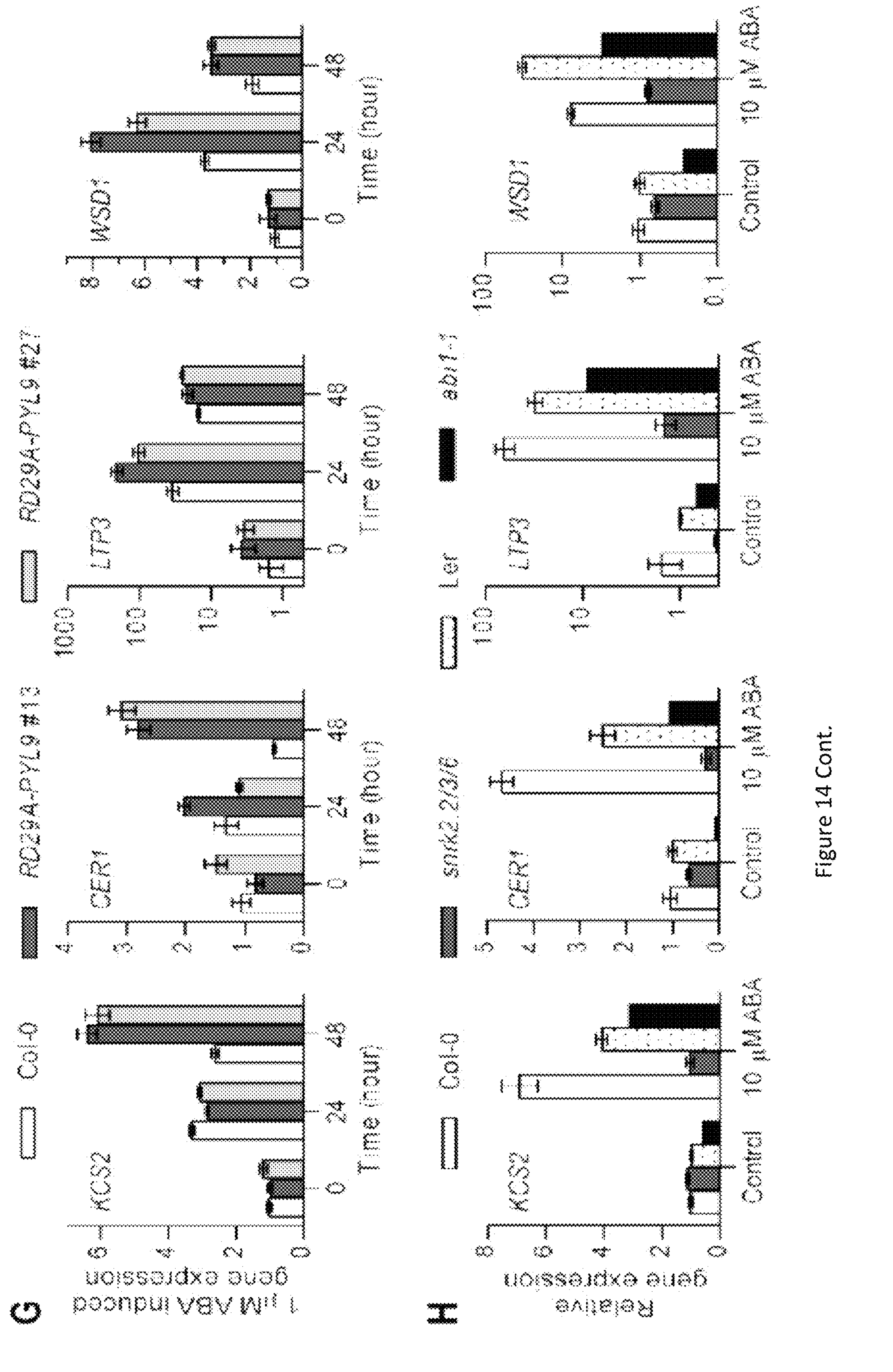

To help plants survive extreme environmental conditions, ABA promotes growth inhibition and dormancy (10). The pRD29A::PYL9 lines showed a stronger seed dormancy and growth inhibition than the Col-0 WT under ABA treatment (FIG. 14 A-C), whereas the seed dormancy and rosette growth of pyl8-1pyl9 and snrk2.2/3/6 were less sensitive to ABA treatment (FIGS. 14 A, D, and E). The pRD29A::PYL9 rice lines also showed a more severe growth inhibition than the ZH11 WT in response to the ABA treatment (FIG. 14F). These results indicated that PYL9 promotes, through the core ABA signaling pathway, ABA-induced seed dormancy and growth inhibition of buds.

ABA promotes stomatal closure to reduce water loss. To protect plants from nonstomatal water loss, ABA induces the accumulation of cuticular wax by up-regulating wax biosynthetic genes (33). The 3-ketoacyl-CoA synthetase 2, ECERIFERUM 1, lipid transfer protein 3, and wax ester synthase 1 were more strongly induced after ABA treatment in pRD29A::PYL9 lines than in the WT (FIG. 14G). Furthermore, the expression of wax biosynthetic genes was reduced in both abi1-1 and snrk2.2/3/6 than in those of the WT in either the absence or presence of ABA (FIG. 14H). These results are consistent with PYL9 promotion of ABA-induced wax biosynthesis through the core ABA signaling pathway. The accumulation of cuticular wax may be especially relevant in very young leaves, where stomata have not developed fully.

Discussion

To escape extreme environmental conditions, plants use a dormancy phase to survive. The two major forms of dormancy are seeds and dormant buds. These forms of dormancy are determined genetically and affected by environmental changes (23). ABA increases plant survival in extreme drought by inducing short-, such as stomatal closure, and long-term responses, such as senescence and abscission, and different forms of dormancy (2, 10, 23). Plants close stomata in response to drought by producing ABA, which is a rapid response that blocks most water loss and gains time for long-term responses to be established. Plants developed an important long-term defense against limited water by favoring water consumption in only newly developed organs and eventually, inducing strong dormancy in meristems or buds. A nonobvious part of this defense in its early stages is the premature senescence and/or abscission of old organs (FIG. 15), which are easily mistaken as drought sensitivity.

Figure 15:
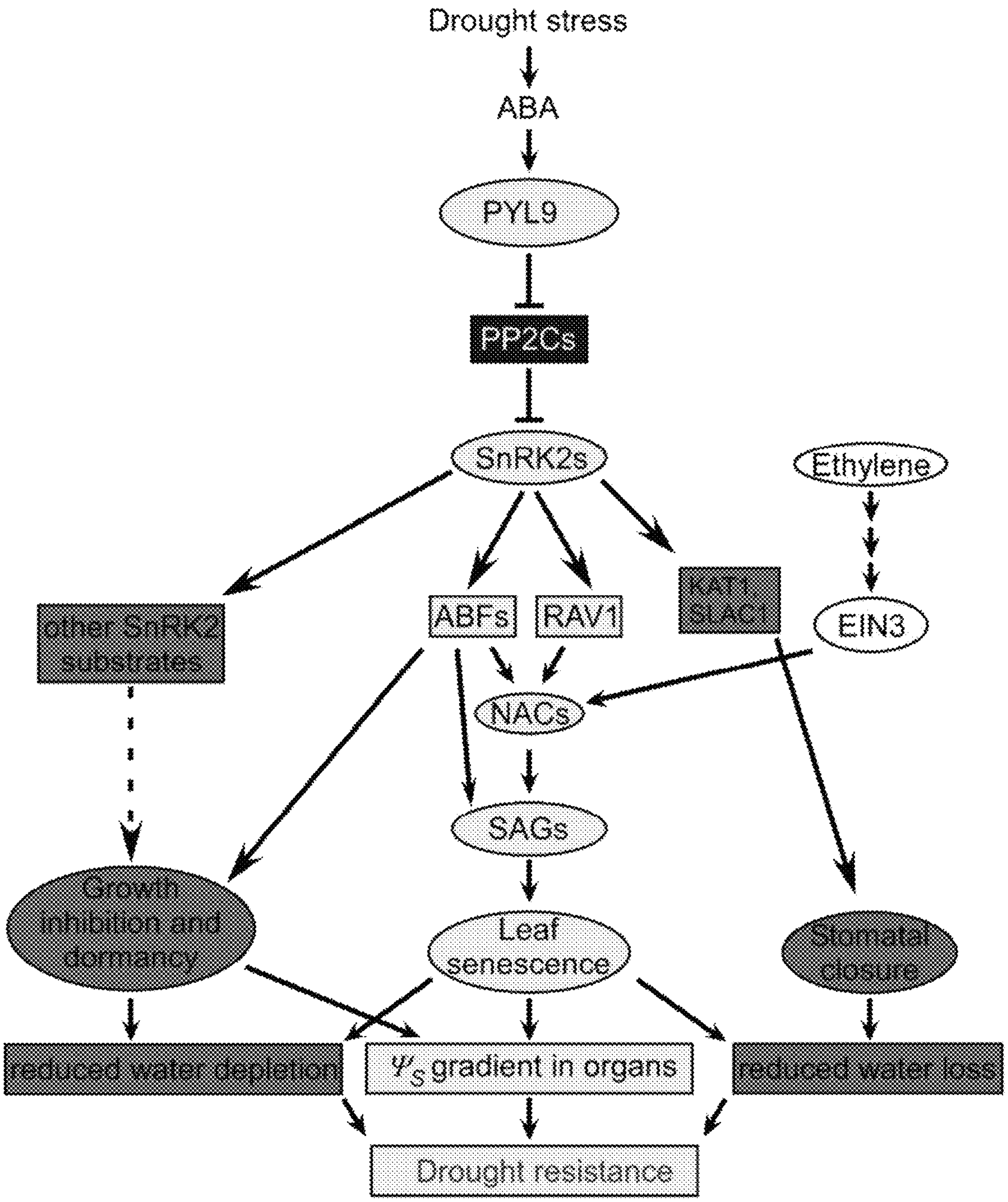
FIG. 15 shows proposed model of PYL9-enhanced drought resistance in *Arabidopsis*. Drought stress induces the elevation of ABA concentration. In response to ABA, PYL9 inhibits PP2C activities, resulting in the activation of SnRK2s. Activated SnRK2s promote stomatal closure by phosphorylating KAT1, SLAC1, and SLAH3, which is a rapid response that reduces transpirational water loss. Activated SnRK2s promote leaf senescence by phosphorylating RAV1 and ABFs, which in turn, up-regulates the expression of NAC transcription factors ORE1, ORS1, and AtNAP, elevating the expression of hundreds of SAGs. Other than ABA, ethylene signaling also promotes senescence by up-regulation of NAC expression through EIN3. Leaf senescence promotes carbohydrate and nitrogen remobilization from senescing leaves to sink tissues, which contributes to osmotic potential ($\Psi\pi$) reduction in sink tissues and the loss of the ability for osmotic adjustment in senescing leaves. Activated SnRK2s also promote growth inhibition and dormancy by phosphorylating ABFs and other SnRK2 substrates and reduce water depletion resulting from growth. The growth inhibition and dormancy also contribute to Ψπ-reduction in sink tissues and formation of a Ψπ-gradient in the plant, which causes water to preferentially move to sink tissues, thereby increasing drought resistance.

Leaf senescence and abscission are forms of programmed cell death. They occur slowly and are associated with efficient transfer of nutrients from the senescing leaves to the developing or storage parts of plants (34). Promotion of leaf senescence and abscission by ABA is a long-term response that allows survival of extreme drought conditions. By selection of the best transgenic survivors of extreme drought conditions, the present invention reveals that ABA mediates survival by promoting leaf senescence through the ABA receptor PYL9 and other PYLs, PP2C coreceptors, SnRK2 protein kinases, and ABFs and RAV1 transcription factors (FIG. 15). ABFs and RAV1 are positive regulators of ABA-induced leaf senescence (FIG. 4) (31) and overall survival. Phosphorylation of ABFs and RAV1 by SnRK2s is important for their functions in ABA-induced leaf senescence (FIG. 4) and increased survival (15). When phosphorylated by SnRK2s, RAV1 and ABFs increase the expression of NAC transcription factors through ABRE motifs and/or RAV1-binding motifs (FIG. 13C) (8). These NAC transcription factors promote the expression of downstream SAGs, which in turn, control leaf senescence (5-7, 34). The SAGs are involved in transcription regulation, protein modification and degradation, macromolecule degradation, transportation, antioxidation, and autophagy (35). The association of senescing leaves with provision of nutrients to sink tissues during drought suggests that drought survival and leaf senescence are linked by ABA signaling. This common connection through the core ABA pathway finally uncovers the underlying molecular mechanism of drought- and ABA-induced leaf senescence and its association with the ability to survive extreme drought. It must be remembered that many injury responses to drought may resemble senescence symptoms but are mediated by separate signaling pathways.

ABA promotes dormancy and growth inhibition through core ABA signaling (25). Seeds can live for many years in a deep dormancy, escaping extreme environmental conditions. Many plants, especially perennials, have a bud-to-bud lifecycle in addition to a seed-to-seed cycle. Bud dormancy is less extreme and more flexible than seed dormancy. Perennial plants can temporarily cease meristematic activity in response to the inconsistent or unusual timing of unfavorable environmental conditions (23). ABA accumulates in polar apical buds during short-day conditions, which may contribute to growth suppression and maintenance of dormancy (36). Of 146 BRC1-dependent bud dormancy genes that are putatively involved in shade-induced axillary bud dormancy, 78 are regulated during senescence (35, 37, 38). Strikingly, master positive regulators of senescence, such as ORE1, AtNAP, and MAX2/ORE9, are also up-regulated during bud dormancy, suggesting that bud dormancy is coordinated with leaf senescence to contribute to stress resistance. Most of these bud dormancy genes contain a CACGTGt motif (SEQ ID NO: 106) in their promoters (37), which is recognized by ABA-related basic region-leucine zipper (b-ZIP) transcription factors (39).

Water flows from tissues with higher water potential to those with lower water potential. During drought stress, the young sink tissues but not senescing leaves can steadily decrease their water potential through osmotic adjustment, which ensures that water flows to these sink tissues (FIG. 5B). Under drought conditions, senescence of sources is, however, accompanied by growth inhibition and dormancy or paradormancy (23) in sinks, which elevate the osmolyte concentration in sinks (passive osmotic adjustment). Because the water potential of the atmosphere is extremely low under drought conditions, a relatively sealed plant surface is required to limit nonstomatal water loss. Sealing of the plant surface requires the accumulation of cuticular wax (33). ABA up-regulates wax biosynthesis genes through the core ABA signaling pathway (FIGS. 14 G and H). The promotion of wax biosynthesis by ABA in buds entering dormancy may also contribute to the improved survival of pRD29A::PYL9 transgenic lines under drought conditions.

Taken together, the data in the present invention suggests that the ABA core signaling pathway plays a crucial role in survival of extreme drought by promoting stomatal closure, growth inhibition, bud dormancy, and leaf senescence. The ABA-induced dormancy-related genes and the ABA-induced senescence-related genes are largely the same genes, which are simultaneously regulated. Senescence occurs in source tissue and leads to death, whereas dormancy occurs in sink tissue and maintains life. This combination of death and life is similar to a triage strategy, and it is consistent with plant survival and therefore, species persistence during episodes of extreme environmental conditions during evolution.

The present invention generated drought-resistant pRD29A::PYL9 transgenic plants from a large-scale screening of transgenic lines and illustrated the mechanism and important role of ABA-induced leaf senescence under severe drought stress. In both *Arabidopsis* and rice in extreme drought conditions, the pRD29A::PYL9 transgenic lines exhibited reduced transpirational water loss, accelerated leaf senescence, reduced cell membrane damage, reduced oxidative damage, increased water use efficiency, and finally, increased survival rates. In addition to being more efficient than the 35S promoter for engineering drought-resistant transgenic plants, the RD29A promoter lacks undesirable phenotypes, including retarded growth under normal growth conditions. The enhanced drought survival of pRD29A::PYL9 transgenic plants can be further enhanced by the external application of ABA or its analogs. The combined use of pRD29A::PYL9 transgenic plants and applications of ABA or its analogs represents an effective way to protect crops from severe drought stress.

Materials and Methods

Plasmid Constructs.

The ORFs of the PYLs were amplified from *Arabidopsis* Col-0 WT cDNA and cloned into the binary vector pCAMBIA 99-1 under the control of the original CaMV 35S promoter (SEQ ID NO. 100) or other promoters, including the RD29A promoter (At5g52310) (SEQ ID NO. 99), GC1 promoter (At1g22690) (SEQ ID NO. 101), RBCSIA promoter (At1g67090) (SEQ ID NO. 102), and ROP11 promoter (At5g62880) (SEQ ID NO. 103) (Table 2). The primers used are provided in sequence listings, and the amplified fragments were confirmed by sequencing.

pGADT7-PP2Cs, pGADT7-MYB44, pBD-GAL4 Cam-PYLs, pHBT-PYL9, pHBT-PP2Cs, pHBT-SnRK2.6, pHBT-ABF2, ABF2$^{S26DS86DS94DT135D}$, and RD29B-LUC were the same as reported (13, 18, 19, 25). ZmUBQ::GUS was provided by J. Sheen, Department of Genetics, Harvard Medical School, Boston. To generate SAG12-LUC and ORE1L-LUC constructs, the 788-bp SAG12 and 3,984-bp ORE1L promoter fragments amplified from Col-0 genomic DNA with primers SAG12proF/R (SEQ ID NOs. 39 and 40) and ORE1LproF/R (SEQ ID NOs. 41 and 42) were cloned into the BamHI and NcoI of the RD29B-LUC vector, respectively. ABI5, EEL, AREB3, ORE1, ORS1, AtNAP, and RAV1 were cloned into pHBT95 using transfer PCR with pHBT genes primers. All plasmids were confirmed by sequencing.

To generate the ProPYL9:PYL9-HA-YFP construct, the 2,566-bp PYL9 promoter fragment amplified from Col-0 genomic DNA with the primers pPYL9F (SEQ ID NO. 37) and PYL9genoR (SEQ ID NO. 38) was cloned into the SalI and ApaI sites of the modified pSAT vector with YFP and 3HA tags at the C terminus. The coding region of PYL9 from pCAMBIA99-1-PYL9 was then subcloned between the PYL9 promoter and the HA-YFP coding sequence. The whole insertion cassette was digested with PI-Psp1 and reinserted into pRCS2-htp binary plasmids.

Plant Materials.

The pyl8-1 mutant (SAIL_1269_A02) (19), the pyl9 mutant (SALK_083621) (17), and the snrk2.2/3/6 triple mutant (10) are in the Col-0 background. The pyl8-1, pyl9, and abi5-1 mutants were obtained from the *Arabidopsis* Biological Resource Center.

The pCAMBIA 99-1-PYLs and ProPYL9:PYL9-HA-YFP plasmids were transformed into *Arabidopsis* ecotype Col-0 and rice cultivar ZH11 using *Agrobacterium tumefaciens* GV3101. All transgenic plants were screened for hygromycin resistance and verified by PCR or Northern blot assays. T2 generation plants were used for the drought-stress resistance test.

Plant Growth Conditions.

*Arabidopsis* seeds were surface-sterilized in 20% (vol/vol) bleach for 10 min and then, rinsed four times in sterile-deionized water. Sterilized seeds were grown vertically on 0.6% Phytagel (Sigma) or horizontally on 0.3% Phytagel medium containing ½ Murashige and Skoog nutrients (PhytoTech) and 1% sucrose (pH 5.7) and kept at 4-8° C. for 3 d. Seedlings were grown vertically for 3 d before transfer to medium with or without the indicated concentrations of ABA (A1049; Sigma). After the seedlings were transferred to the control medium, the plates were sealed with micropore tape (3M), and the seedlings were grown horizontally in a Percival CU36L5 Incubator at 23° C. under a 16-h light/8-h dark photoperiod.

For protoplast analysis, seedlings were grown under a relatively short photoperiod (10 h light at 23° C. and 14 h dark at 20° C.) as reported (19). For drought-stress analysis, *Arabidopsis* plants were grown in a growth room at 22° C./18° C. under a 14-h light/10-h dark photoperiod with a light intensity of 100 $\mu$mol $m^{-2}$ $s^{-1}$, and rice plants were grown at 26° C./22° C. under a 14-h light/10-h dark photoperiod and 75%/70% relative humidity with a light intensity of 600 $\mu$mol $m^{-2}$ $s^{-1}$.

Transient Expression Assay in *Arabidopsis*.

Assays for transient expression in protoplasts were performed as described (18). All steps were performed at room temperature. SAG12-LUC and ORE1L-LUC were used as the senescence-responsive reporters, and ZmUBQ-GUS was used as the internal control. After transfection, protoplasts were incubated in washing and incubation solution without ABA or with 5 $\mu$M ABA under light for 16 h.

Drought-Stress Treatments.

The T2 generation of transgenic *Arabidopsis* plants was subjected to a first-round drought-stress resistance test in soil. All seeds were imbibed at 4° C. for 2 d and planted directly in soil in 18-cm-diameter pots. Five days after seedlings emerged, each pot was thinned to eight seedlings of uniform size. Drought treatment was imposed for 20 d beginning at 10 d after seedlings emerged by withholding water; after 20 d of drought, most WT plants had died. At least three transgenic lines from each promoter-transgene combination and five pots for each line were used in this test. The positions of pots were exchanged every day to minimize the effect of environmental variability in the growth chambers. The plants were rewatered on day 31 (1 d after the 20-d drought treatment) and assessed for survival 2 d later. The second round of screening was carried out in the same manner using only those transgenic lines that were found to be relatively drought-resistant in the first round of screening.

For testing the drought resistance of transgenic rice lines, rice plants at the four-leaf stage were subjected to drought treatment for 14 d and then rewatered as needed for 14 d. To minimize environmental variability, the pots were rotated daily. The survival rate of stressed plants was recorded at 14 d after rewatering began.

Soil Water Content Analysis.

Soil water content percentage during drought treatment in *Arabidopsis* was measured as described (27). We used 591-mL pots (48-7214; 04.00 SQ TL TW; Myers Industries) with 130 g (~62 g oven dry weight) Fafard Super-Fine Germinating Mix Soil (Sungro Horticultures) per pot. After being saturated with water, the total weight of the wet soil was ~440 g per pot. Pots were covered with plastic film to reduce water loss from soil surface. Three-week-old plants (four plants per pot) were subjected to drought stress by withholding water. Plants were sprayed with 2 mL 10 μM ABA plus 0.2% Tween-20 per pot after water was withheld for 12 d. Soil water content percentage was computed as total weight minus dry soil weight divided by water weight before drought according to the work (27). For drought treatment on rice, we measured the relative water content using the Soil Temperature/Moisture Meter L99-TWS-1 (Shanghai Fotel Precise Instrument Co., Ltd) following the work (40). Before drought treatment, the mixed vermiculite and sandy soil (Zhongfang Horticulture Co.) for rice was saturated with water, and the relative soil water content before drought was set as 100%. Rice plants at the four-leaf stage were subjected to drought by withholding water for 14 d, and the relative soil water content after the drought treatment was ~20%.

Measurement of Photosynthesis Parameters and Water Loss.

Photosynthesis parameters were measured as reported (18). At least four independent plants were used for each transgenic line. The experiment was repeated twice with similar results. The fresh weight of the aerial part of each plant was recorded before rewatering, and dry weight was measured after 2 d at 80° C. Water was withheld from 2-wk-old plants for 20 d, and the aboveground materials were collected and weighed before and after drying. For determination of water loss, whole rosettes of 18-d-old plants were cut from the base and weighed at indicated time points.

Measurement of Electrolyte Leakage.

For the determination of electrolyte leakage, about 0.1 g plant leaves were placed in a flask containing 10 mL deionized water and shaken on a gyratory shaker at room temperature for 6 h at about 150 rpm. After the initial conductivity (Ci) was measured with a conductivity meter (Leici-DDS-307A), the samples were boiled for 20 min to kill the leaf tissues and completely release the electrolytes into the solution. After the samples had cooled to room temperature, the conductivity of the killed tissues (Cmax) was measured. The relative electrolyte leakage was calculated as (Ci/Cmax)×100%.

Determination of Hydrogen Peroxide Level and Activities of Antioxidant Enzymes.

For hydrogen peroxide ($H_2O_2$) content measurement, water was withheld from 2-wk-old plants for 14 d, and the leaves were collected. For antioxidant enzyme activities, water was withheld from 3-wk-old plants for 10 d.

For $H_2O_2$ content quantification, 1 mL plant extract in 50 mM sodium phosphate buffer (pH 7.8) was mixed with 1 mL 0.1% (wt/vol) titanium sulfate [in 20% (vol/vol) $H_2SO_4$] for 10 min. After centrifugation at 15,294×g for 10 min, the absorbance of the supernatant was measured at 410 nm using a standard curve generated with known concentrations of $H_2O_2$ as a control. The concentration of proteins was quantified using the Bradford method. Catalase (EC 1.11.1.6), superoxide dismutase (EC 1.15.1.1), and peroxidase (EC 1.11.1.7) activities were analyzed as described previously (41).

Measurement of Chlorophyll Content.

Four-week-old *Arabidopsis* plants in soil were sprayed with 20 μM ABA plus 0.2% Tween-20. Rice plants in soil were sprayed with 100 μM ABA plus 0.2% Tween-20. After the fresh weight of samples was determined, samples were quick-frozen, ground in liquid nitrogen, and then, homogenized in extraction buffer containing ethanol, acetone, and $H_2O$ in a ratio of 5:5:1. The mixture was incubated at 37° C. for 4 h and centrifuged at 16,000×g for 5 min. The absorbance of the clear supernatant was measured at wavelengths of 645 nM (D645) and 663 nM (D663) using a plate reader (Wallac VICTOR2 Plate Reader) with filters at 642 and 665 nm, respectively. The concentrations of chlorophyll pigments were calculated as follows: concentration (milligrams per liter)=20.2×D645+8.02×D663.

Tandem Affinity Purification.

Ten-day-old seedlings of the transgenic *Arabidopsis* plants expressing ProPYL9:PYL9-HA-YFP (FIG. 12A) were used for tandem affinity purification. Seedlings (3-4 g fresh weight) were treated for 1 h with ½ Murashige and Skoog medium containing 100 μM ABA or 30 min with ½ Murashige and Skoog medium containing 0.8 M mannitol; for the control, seedlings were treated with ½ Murashige and Skoog medium for 1 h. After treatment, samples were quickly frozen, ground in liquid $N_2$, homogenized in an equal volume of 2× immunoprecipitation (IP) buffer (100 mM Tris·HCl, pH 7.5, 300 mM NaCl, 2 mM EDTA, 0.2% Nonidet P-40, 2× protease mixture; Roche), and then, centrifuged at 30,000×g for 30 min at 4° C. The supernatant was passed through a 0.2-μM filter and centrifuged again at 30,000×g for 30 min at 4° C. After that, the supernatant was incubated with 40 μL 50% (vol/vol) slurry of monoclonal anti-HA agarose with antibody produced in mouse (A2095; Sigma), which was prebalanced with 1×IP buffer. The mixture was inverted for 1 h at 4° C. on a shaker. The agarose was then washed four times with 1×IP buffer, three times with high NaCl buffer (50 mM Tris·HCl, pH 7.5, 500 mM NaCl, 1 mM EDTA), and finally, three times with 1×IP buffer. The protein that had bound to the anti-HA agarose was eluted by HA peptide (ab13835; Abcam) with a concentration of 0.5 μg/L in 200 μL 1×IP buffer overnight at 4° C. The supernatant was then incubated with 20 μL 50% (vol/vol) slurry of GFP-Trap Agarose (gta-20; Chromotek), which was prebalanced with 1×IP buffer. The mixture was inverted for 1 h at 4° C. on a shaker. The GFP-Trap Agarose was washed four times with 1×IP buffer and then, five times with 1×PBS buffer. Finally, the PYL9-associated proteins on the GFP-Trap Agarose were identified by MS analyses (Table 1).

Northern Blot and Real-Time PCR Assay.

Northern blot and real-time PCR were performed as reported (18). For Northern blot analysis, the probe was labeled with the PCR-DIG Probe Synthesis Kit (Roche). RD29A-F (SEQ ID NO. 83) and PYL9-R (SEQ ID NO. 84) were used for the PCR. For real-time PCR, reactions were performed with iQ SYBR Green Supermix (BioRad). The primers used include SEQ ID NOs. 71 to 80. Quantitative RT-PCR was conducted on mature leaves of 4-wk-old *Arabidopsis* plants that were growing in soil and sprayed with 20 μM ABA.

Rice plants in soil were sprayed with 100 μM ABA plus 0.2% Tween-20. Quantitative RT-PCR was conducted on third oldest leaves of rice plants that were growing in soil and sprayed with 100 μM ABA.

Y2H Assays.

Y2H assays were performed as described (18). pBD-GAL4-PYLs were the same as reported (13). PYL9 and PYL8 fused to the GAL4-DNA-binding domain were used as baits. PP2Cs and MYB44 fused to the GAL4-activating domain were used as prey.

Sequence Comparison.

ABF2 homologs were obtained from The *Arabidopsis* Information Resource (www.arabidopsis.org). Protein sequences were aligned using ClustalX 2.0.5 with the default settings (Table 1) and viewed using GeneDoc software found on the internet at nrbsc.org.gfs.genedoc.

Osmotic Potential Measurements.

Plant samples were collected in a plastic centrifuge tube filter (without membrane; Corning Costar Spin-X) and then, quick-frozen in liquid nitrogen. After thawing, the sap was collected by centrifuging at 16,000×g for 4 min to remove insoluble material. A 10-μL volume of cell sap was measured using a vapor pressure osmometer (Model 5200; Wescor). Solute concentration was converted to osmotic potential ($\Psi\pi$) using the van't Hoff law: $\Psi\pi=-RTc$, where c is the molar solute concentration (osmolality; moles kilogram-1), R is the gas constant (0.08314 L Bar mol−1 K−1), and T is the temperature in Kelvin.

REFERENCES

The contents of the followings references are incorporated herein for all purposes.

1. Rivero R M, et al., (2007) Delayed leaf senescence induces extreme drought tolerance in a flowering plant. *Proc Natl Acad Sci USA,* 104(49): 19631-19636.
2. Lim P O, Kim H J, Nam H G, (2007) Leaf senescence. *Annu Rev Plant Biol,* 58:115-136.
3. Munné-Bosch S, Alegre L., (2004) Die and let live: Leaf senescence contributes to plant survival under drought stress. *Funct Plant Biol,* 31(3):203-216.
4. Gan S, Amasino R M, (1995) Inhibition of leaf senescence by autoregulated production of cytokinin. *Science,* 270 (5244):1986-1988.
5. Kim J H, et al., (2009) Trifurcate feed-forward regulation of age-dependent cell death involving miR164 in *Arabidopsis. Science,* 323(5917):1053-1057.
6. Balazadeh S, et al., (2011) ORS1, an H2O2-responsive NAC transcription factor, controls senescence in *Arabidopsis thaliana. Mol Plant,* 4(2):346-360.
7. Guo Y, Gan S, (2006) AtNAP, a NAC family transcription factor, has an important role in leaf senescence. *Plant J,* 46(4):601-612.
8. Sakuraba Y, et al., (2014) Phytochrome-interacting transcription factors PIF4 and PIF5 induce leaf senescence in *Arabidopsis. Nat Commun,* 5:4636.
9. Liang C, et al., (2014) OsNAP connects abscisic acid and leaf senescence by fine-tuning abscisic acid biosynthesis and directly targeting senescence-associated genes in rice. *Proc Natl Acad Sci USA,* 111(27):10013-10018.
10. Fujii H, Zhu J K, (2009) *Arabidopsis* mutant deficient in 3 abscisic acid-activated protein kinases reveals critical roles in growth, reproduction, and stress. *Proc Natl Acad Sci USA,* 106(20):8380-8385
11. Riov J, Dagan E, Goren R, Yang S F, (1990) Characterization of abscisic Acid-induced ethylene production in citrus leaf and tomato fruit tissues. *Plant Physiol,* 92(1): 48-53.
12. Weaver L M, Gan S, Quirino B, Amasino R M, (1998) A comparison of the expression patterns of several senescence-associated genes in response to stress and hormone treatment. *Plant Mol Biol,* 37(3):455-469.
13. Park S Y, et al., (2009) Abscisic acid inhibits type 2C protein phosphatases via the PYR/PYL family of START proteins. *Science,* 324(5930):1068-1071.
14. Ma Y, et al., (2009) Regulators of PP2C phosphatase activity function as abscisic acid sensors. *Science,* 324 (5930):1064-1068.
15. Furihata T, et al., (2006) Abscisic acid-dependent multisite phosphorylation regulates the activity of a transcription activator AREB1. *Proc Natl Acad Sci USA,* 103(6): 1988-1993.
16. Hao Q, et al., (2011) The molecular basis of ABA-independent inhibition of PP2Cs by a subclass of PYL proteins. *Mol Cell,* 42(5):662-672.
17. Antoni R, et al., (2013) PYRABACTIN RESISTANCE1-LIKE8 plays an important role for the regulation of abscisic acid signaling in root. *Plant Physiol,* 161(2):931-941.
18. Zhao Y, et al., (2013) The unique mode of action of a divergent member of the ABA-receptor protein family in ABA and stress signaling. *Cell Res,* 23(12):1380-1395.
19. Zhao Y, et al., (2014) The ABA receptor PYL8 promotes lateral root growth by enhancing MYB77-dependent transcription of auxin-responsive genes. *Sci Signal,* 7(328): ra53.
20. Yang Y, Costa A, Leonhardt N, Siegel R S, Schroeder J I, (2008) Isolation of a strong *Arabidopsis* guard cell promoter and its potential as a research tool. *Plant Methods,* 4(1):6.
21. Li Z, Kang J, Sui N, Liu D, (2012) ROP11 GTPase is a negative regulator of multiple ABA responses in *Arabidopsis. J Integr Plant Biol,* 54(3): 169-179.
22. Chattopadhyay S, Ang L H, Puente P, Deng X W, Wei N, (1998) *Arabidopsis* bZIP protein HY5 directly interacts with light-responsive promoters in mediating light control of gene expression. *Plant Cell,* 10(5):673-683.
23. Volaire F, Norton M, (2006) Summer dormancy in perennial temperate grasses. *Ann Bot,* (Lond) 98(5):927-933.
24. Bhaskara G B, Nguyen T T, Verslues P E, (2012) Unique drought resistance functions of the highly ABA-induced clade A protein phosphatase 2Cs. *Plant Physiol,* 160(1): 379-395.
25. Fujii H, et al., (2009) In vitro reconstitution of an abscisic acid signalling pathway. *Nature,* 462(7273):660-664.
26. Cao M, et al., (2013) An ABA-mimicking ligand that reduces water loss and promotes drought resistance in plants. *Cell Res,* 23(8):1043-1054.
27. Okamoto M, et al., (2013) Activation of dimeric ABA receptors elicits guard cell closure, ABA-regulated gene expression, and drought tolerance. *Proc Natl Acad Sci USA,* 110(29): 12132-12137.
28. Olsen A N, Ernst H A, Leggio L L, Skriver K, (2005) DNA-binding specificity and molecular functions of NAC transcription factors. *Plant Sci* 169(4):785-797.
29. Kim J H, Chung K M, Woo H R, (2011) Three positive regulators of leaf senescence in *Arabidopsis*, ORE1, ORE3 and ORE9, play roles in crosstalk among multiple hormone-mediated senescence pathways. *Genes Genomics,* 33(4):373-381.
30. Feng C Z, et al., (2014) *Arabidopsis* RAV1 transcription factor, phosphorylated by SnRK2 kinases, regulates the expression of ABI3, ABI4, and ABI5 during seed germination and early seedling development. *Plant J,* 80(4): 654-668.

31. Woo H R, et al., (2010) The RAV1 transcription factor positively regulates leaf senescence in *Arabidopsis*. *J Exp Bot*, 61(14):3947-3957.

32. Chen L Q, et al., (2012) Sucrose efflux mediated by SWEET proteins as a key step for phloem transport. *Science*, 335(6065):207-211.

33. Samuels L, Kunst L, Jetter R, (2008) Sealing plant surfaces: Cuticular wax formation by epidermal cells. *Annu Rev Plant Biol*, 59:683-707.

34. Uauy C, Distelfeld A, Fahima T, Blechl A, Dubcovsky J, (2006) A NAC Gene regulating senescence improves grain protein, zinc, and iron content in wheat. *Science*, 314(5803):1298-1301.

35. Buchanan-Wollaston V, et al., (2005) Comparative transcriptome analysis reveals significant differences in gene expression and signalling pathways between developmental and dark/starvation-induced senescence in *Arabidopsis*. *Plant J*, 42(4): 567-585.

36. Ruttink T, et al., (2007) A molecular timetable for apical bud formation and dormancy induction in poplar. *Plant Cell*, 19(8):2370-2390.

37. González-Grandio E, Poza-Carrión C, Sorzano C O, Cubas P, (2013) BRANCHED1 promotes axillary bud dormancy in response to shade in *Arabidopsis*. *Plant Cell*, 25(3):834-850.

38. van der Graaff E, et al., (2006) Transcription analysis of *Arabidopsis* membrane transporters and hormone pathways during developmental and induced leaf senescence. *Plant Physiol*, 141(2):776-792.

39. Shen Q, Ho T H, (1995) Functional dissection of an abscisic acid (ABA)-inducible gene reveals two independent ABA-responsive complexes each containing a G-box and a novel cis-acting element. *Plant Cell*, 7(3):295-307.

40. Jin R, et al., (2015) Physiological changes of purslane (*Portulaca oleracea* L.) after progressive drought stress and rehydration. *Sci Hortic*, (Amsterdam) 194:215-221.

41. Shi H, Ye T, Zhu J-K, Chan Z, (2014) Constitutive production of nitric oxide leads to enhanced drought stress resistance and extensive transcriptional reprogramming in *Arabidopsis*. *J Exp Bot*, 65(15):4119-4131.

That which is claimed is:

1. A transgenic plant having increased drought tolerance and leaf senescence transformed with polynucleotide sequence encoding SEQ ID NO: 104, which is a PYL9 protein, and operably linked to a polynucleotide sequence of a stress inducible rd29A promoter, wherein the transgenic plant exhibits increased expression of the PYL9 protein and interacts with abscisic acid (ABA) thereby activating enhanced drought resistance and senescence relative to a non-transformed plant.

2. The transgenic plant according to claim 1, wherein the transgenic plant is a monocotyledonous plant selected from the group consisting of wheat, maize, rye, rice, corn, oat, barley, turfgrass, sorghum, millet and sugarcane or a dicotyledonous plant selected from the group consisting of tobacco, tomato, potato, soybean, cotton, canola, sunflower and alfalfa.

3. A method of producing a transgenic plant having an increased tolerance to an environmental drought stress, said method comprising the steps of:

(a) transforming plant cells with an DNA expression cassette comprising a DNA nucleotide sequence encoding an PYL9 protein having an amino acid sequence of SEQ ID NO. 104, and wherein the DNA nucleotide sequence encoding the PYL9 protein is operably linked to a nucleotide sequence encoding a stress inducible rd29A promoter;

(b) regenerating transgenic plants from said transformed plant cells; and (c) selecting a transformed plant from said transgenic plants which exhibits increase in tolerance to an environmental stress as compared to an untransformed plant of the same species, and wherein said increase in environmental stress tolerance is due to the increased expression of the PYL9 protein in the selected transformed plant, wherein the increased expression of the PYL9 polypeptide interacts with abscisic acid (ABA) thereby activating enhanced drought resistance and senescence relative to the control plant.

4. The method according to claim 3, wherein the DNA nucleotide sequence encoding the PYL9 polypeptide is SEQ ID NO. 89.

5. The method according to claim 3, wherein the transformed plant produces transform seeds, and wherein the transformed seeds comprise the expression cassette and exhibit increase in tolerance to the environmental stress as compared to untransformed seeds of the same species.

6. A method of producing a transgenic plant with increased drought tolerance and leaf senescence as compared to a control or wild type plant, the method comprises the steps of;

(i) providing a recombinant DNA construct comprising a DNA polynucleotide sequence encoding a PYL9 polypeptide having an amino acid sequence of SEQ ID NO. 104, and wherein the DNA polynucleotide sequence encoding a PYL9 polypeptide is operably linked to a polynucleotide sequence of a stress inducible rd29A promoter, and (ii) introducing the recombinant DNA construct into a plant to produce a pRD29A::PYL9 transgenic plant, wherein the pRD29A::PYL9 transgenic plant produces an overexpression of the PYL9 polypeptide to interact with abscisic acid (ABA) thereby exhibiting increased drought tolerance and leaf senescence relative to the control or wild-type plant.

7. The method according to claim 6, wherein the transgenic plant is a monocotyledonous plant selected from the group consisting of wheat, maize, rye, rice, corn, oat, barley, turfgrass, sorghum, millet and sugarcane or a dicotyledonous plant selected from the group consisting of tobacco, tomato, potato, soybean, cotton, canola, sunflower and alfalfa.

8. The method according to claim 6, wherein the method provides for a seed of a transgenic plant, wherein the seed comprises the expression cassette pRD29A::PYL9.

9. The method according to claim 6, wherein the DNA nucleotide sequence encoding the PYL9 protein is SEQ ID NO. 89.

* * * * *